(12) United States Patent
Dohmen et al.

(10) Patent No.: US 12,064,484 B2
(45) Date of Patent: Aug. 20, 2024

(54) COMPOSITIONS FOR INTRODUCING RNA INTO CELLS

(71) Applicant: ETHRIS GMBH, Planegg (DE)

(72) Inventors: Christian Dohmen, Munich (DE); Christian Plank, Seefeld (DE); Carsten Rudolph, Krailing (DE); Christian Koch, Munich (DE)

(73) Assignee: ethris GmbH, Planegg (DE)

(*) Notice: Subject to any disclaimer, the term of this patent is extended or adjusted under 35 U.S.C. 154(b) by 0 days.

(21) Appl. No.: 14/901,467

(22) PCT Filed: Jun. 27, 2014

(86) PCT No.: PCT/EP2014/063756
§ 371 (c)(1),
(2) Date: Dec. 28, 2015

(87) PCT Pub. No.: WO2014/207231
PCT Pub. Date: Dec. 31, 2014

(65) Prior Publication Data
US 2017/0021036 A1    Jan. 26, 2017

(30) Foreign Application Priority Data

Jun. 28, 2013 (EP) .................... 13174390
Aug. 22, 2013 (EP) .................... 13181380

(51) Int. Cl.
| | |
|---|---|
| A61K 47/00 | (2006.01) |
| A61K 9/19 | (2006.01) |
| A61K 31/7088 | (2006.01) |
| A61K 31/713 | (2006.01) |
| A61K 47/26 | (2006.01) |
| A61K 47/58 | (2017.01) |
| A61K 47/59 | (2017.01) |
| A61K 48/00 | (2006.01) |
| C08F 8/32 | (2006.01) |
| C08G 73/02 | (2006.01) |
| C12N 15/87 | (2006.01) |

(52) U.S. Cl.
CPC ............ *A61K 48/0041* (2013.01); *A61K 9/19* (2013.01); *A61K 31/713* (2013.01); *A61K 47/26* (2013.01); *A61K 47/58* (2017.08); *A61K 47/59* (2017.08); *C08F 8/32* (2013.01); *C08G 73/0206* (2013.01); *C08G 73/0213* (2013.01); *C12N 15/87* (2013.01)

(58) Field of Classification Search
None
See application file for complete search history.

(56) References Cited

U.S. PATENT DOCUMENTS

| | | | |
|---|---|---|---|
| 8,450,298 B2 * | 5/2013 | Mahon ............ | A61P 25/18 514/80 |
| 2012/0021042 A1 * | 1/2012 | Panzner ........... | A61K 9/127 424/450 |
| 2012/0301512 A1 | 11/2012 | Xu et al. | |

FOREIGN PATENT DOCUMENTS

| | | |
|---|---|---|
| JP | 2004528101 A | 9/2004 |
| WO | WO 2000/009086 | 2/2000 |
| WO | WO 2000/27795 | 5/2000 |
| WO | WO 2006/066001 | 6/2006 |
| WO | WO 2010/053572 | 5/2010 |
| WO | WO 2010/065660 | 6/2010 |
| WO | WO 2011/154331 | 12/2011 |
| WO | WO 13/090648 * | 6/2013 |
| WO | WO 2014/028487 | 2/2014 |
| WO | WO 2014/066811 | 5/2014 |

OTHER PUBLICATIONS

Ou et al., Biomaterials, 2009, 30: 5804-5814.*
Ankinc et al., Nat. Biotechnol., 2008, 56: 1-20.*
Rejman et al., J. Control. Rel., 2010, 147: 285-391.*
Wang et al., Bioconjugate Chem., 2007, 18: 2169-2177.*
Uchida, Plos One, Feb. 2013, 8: 1-8.*
Tranchant et al., J. Gene Med., 2004, 6: S24-S35.*
Akinc et al., Nat. Biotechnol., 2008, 26: 561-569.*
Sunshine, Joel, et al.: "Small-Molecule End-Groups of Linear Polymer Determine Cell-type Gene-Delivery Efficacy", Advanced Materials, vol. 21, No. 48 (2009), pp. 4947-4951 (XP55095832).
Bhupathiraju et al.: "Synthesis and cellular studies of polyamine conjugates of a mercaptomethyl-carboranylporphyrin", Bioorganic & Medicinal Chemistry, vol. 21, No. 2 (2013), pp. 485-495 (XP055095834).
Aissaoui, Abderrahim et al.: "Efficient topical delivery of plasmid DANN to lung in vivo mediated by putative triggered, PEGylated pDNA nanoparticles", Journal of Controlled Release, vol. 154, No. 3 (2011), pp. 275-284 (XP028285878).
Kolli, Soumia, et al.: "pH-Triggered Nanoparticle Mediated Delivery of siRNA to Liver Cells in Vitro and in Vivo", Bioconugate Chemistry; vol. 24, No. 3 (2013) pp. 314-332 (XP055095835).
Azzam et al.: "Dextran-spermine conjugate: an efficient vector for gene delivery"; Macromolecular Symposia, vol. 195, No. 1 (2003), pp. 247-261 (XP003013580).
Extended European search report for EP Application No. EP 13 18 1380.0, dated Jan. 21, 2014.

(Continued)

*Primary Examiner* — Ileana Popa
(74) *Attorney, Agent, or Firm* — Morse, Barnes-Brown & Pendleton, P.C.; Lisa M. Warren, Esq.; Erin E. Bryan, Esq.

(57) ABSTRACT

The present invention relates to oligomers, polymers and lipidoids comprising characteristic oligo(alkylene amine) moieties which are useful as vehicles for transfecting a cell with RNA. The present invention furthermore relates to a composition comprising at least a nucleic acid and an oligomer or polymer or a lipidoid comprising such oligo(alkylene amine) moieties and to a method of transfecting a cell using said composition. Furthermore, the present invention relates to pharmaceutical compositions and uses.

23 Claims, 26 Drawing Sheets

(56) References Cited

OTHER PUBLICATIONS

Extended European search report for EP Application No. EP 13 17 4390.8, dated Jan. 24, 2014.
International Search Report for Application No. PCT/EP2014/063756 dated Nov. 5, 2014.
Bettinger, et al., 2001, Nucleic Acids Res, 29: 3882-91.
Uzgan, et al., "PEGylation Improves Nanoparticle Formation and Transfection Efficiency of Messenger RNA," 2011, Pharm Res, 28: 2223-32.
Love, Kevin T., et al. "Lipid-like materials for low-dose, in vivo gene silencing." *Proceedings of the National Academy of Sciences* 107.5 (2010): 1864-1869.
Non-Final Office Action Issued in U.S. Appl. No. 15/525,701, dated Feb. 17, 2021.
Jarzębińska, Anita, et al. "A single methylene group in oligoalkylamine-based cationic polymers and lipids promotes enhanced mRNA delivery." *Angewandte Chemie International Edition* 55.33 (2016): 9591-9595.
Final Office Action Issued in U.S. Appl. No. 15/525,701, dated Sep. 22, 2021.
Hosseinkhani, et al., "Impregnation of Plasmid DNA into Three-Dimensional Scaffolds and Medium Perfusion Enhance in Vitro DNA Expression of Mesenchymal Stem Cells," *Tissue Engineering*, 11(9/10):1459-1475 (2005).
Non-Final Office Action from U.S. Appl. No. 15/525,701, date mailed: Mar. 9, 2023.
Non-Final Office Action in U.S. Appl. No. 15/525,701 dated Dec. 13, 2023.
Non-Final Office Aciton in U.S. Appl. No. 15/525,701, date mailed: May 23, 2024.

\* cited by examiner

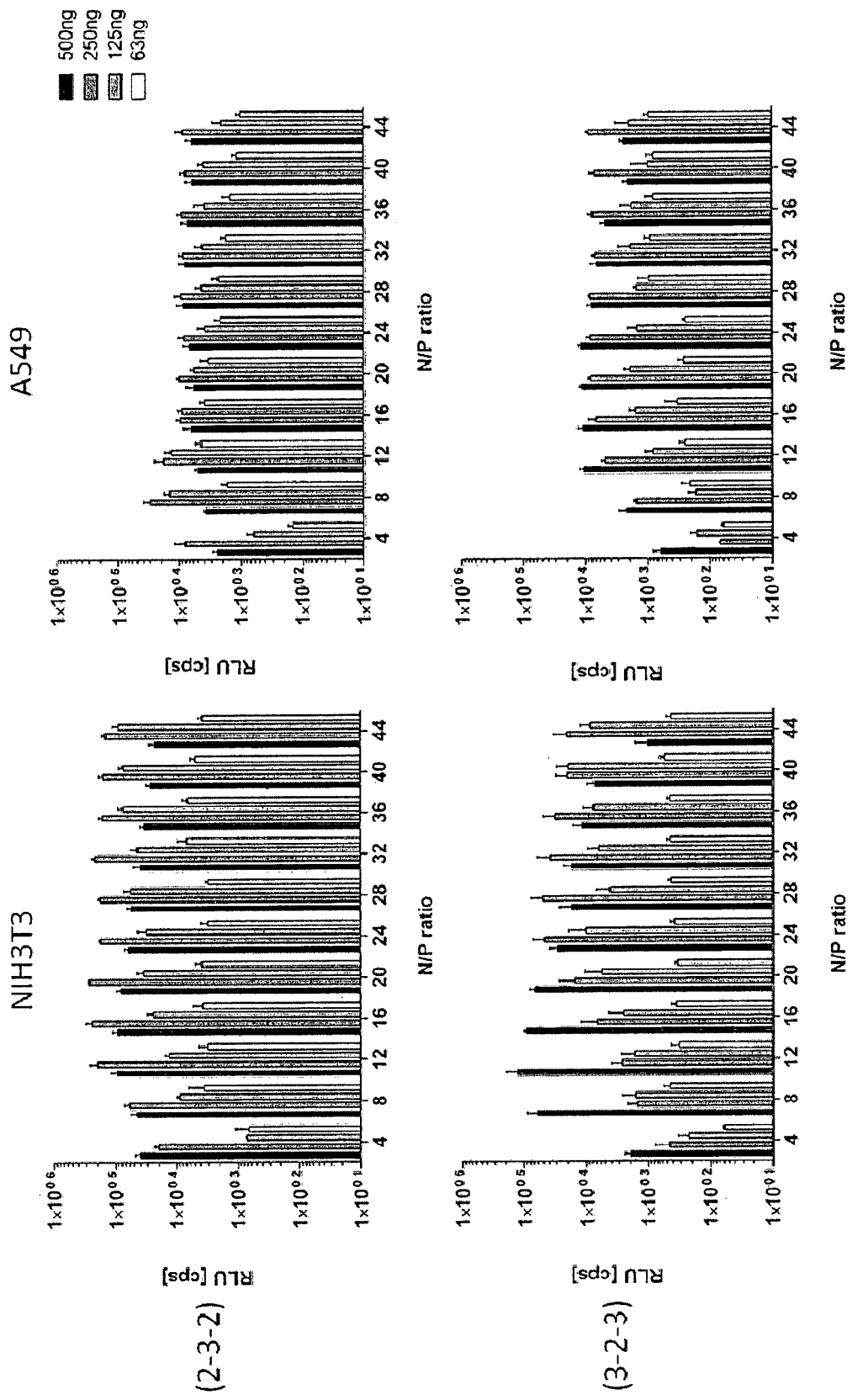
Figure 1 (Part 1/3)

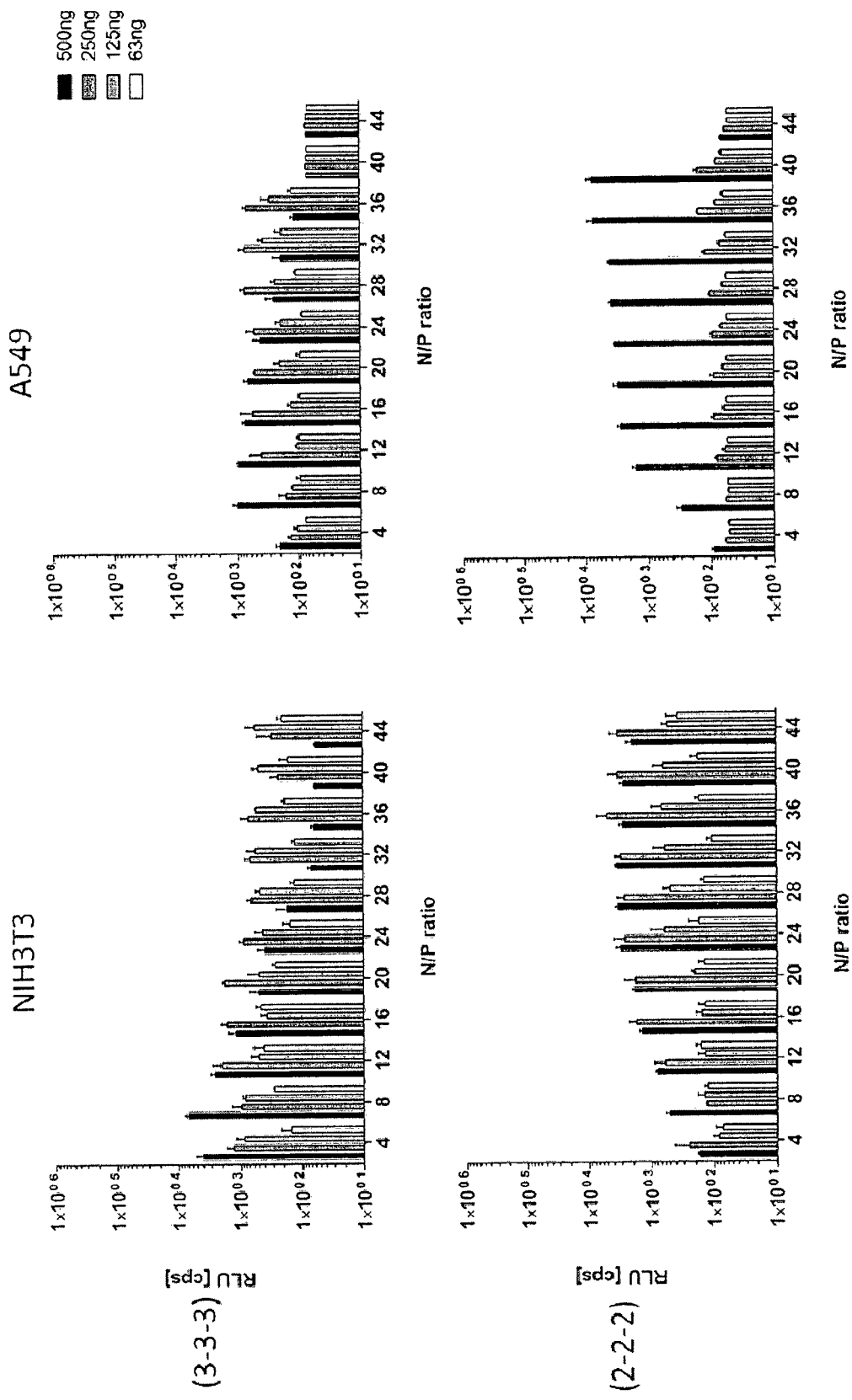
Figure 1 (Part 2/3)

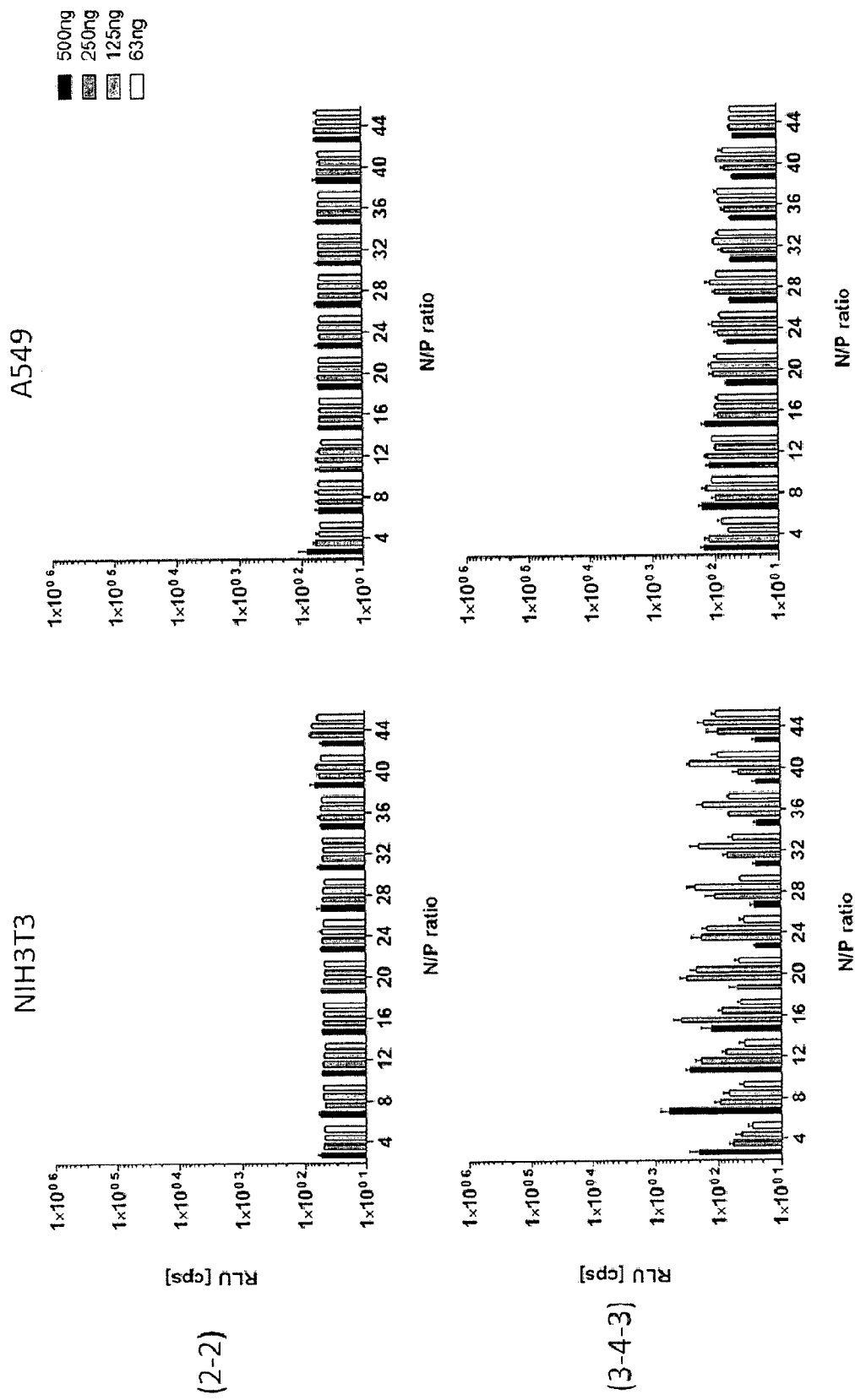
Figure 1 (Part 3/3)

A.
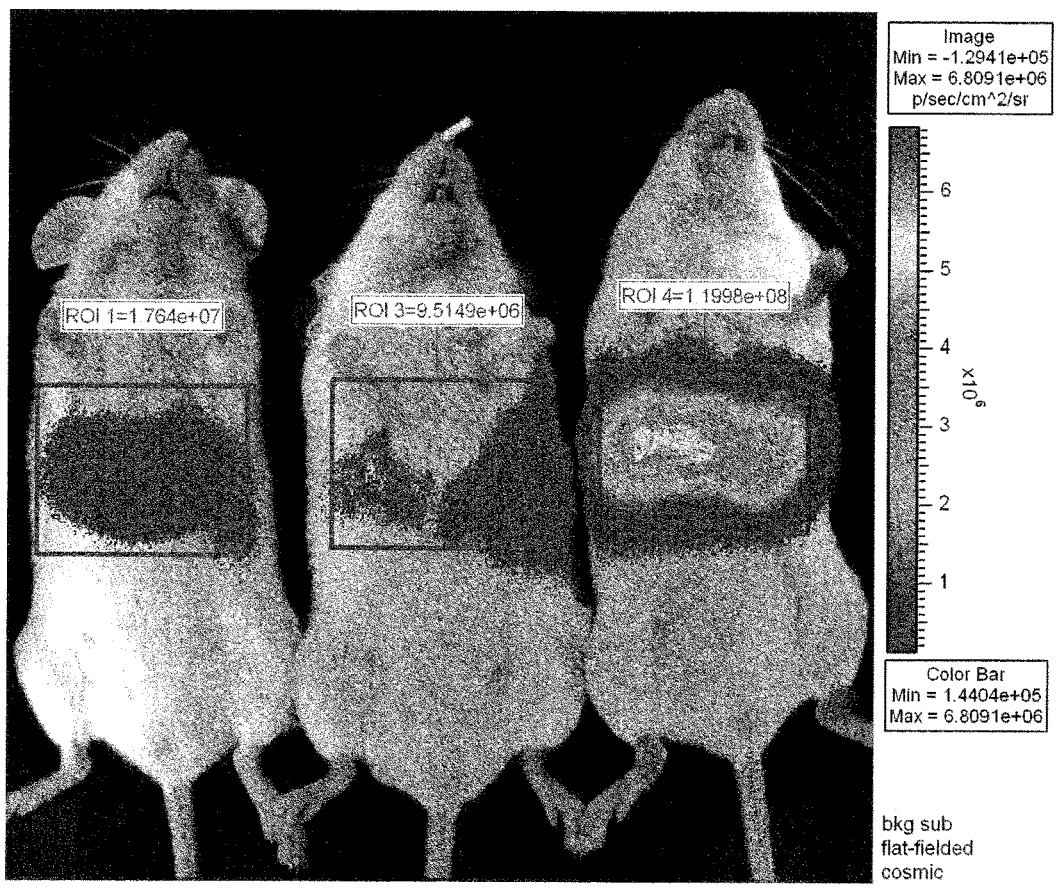
B.
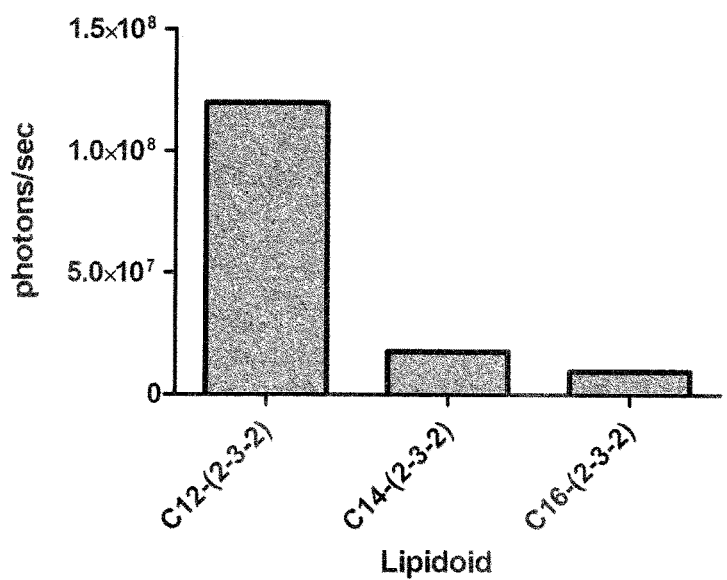
Figure 17

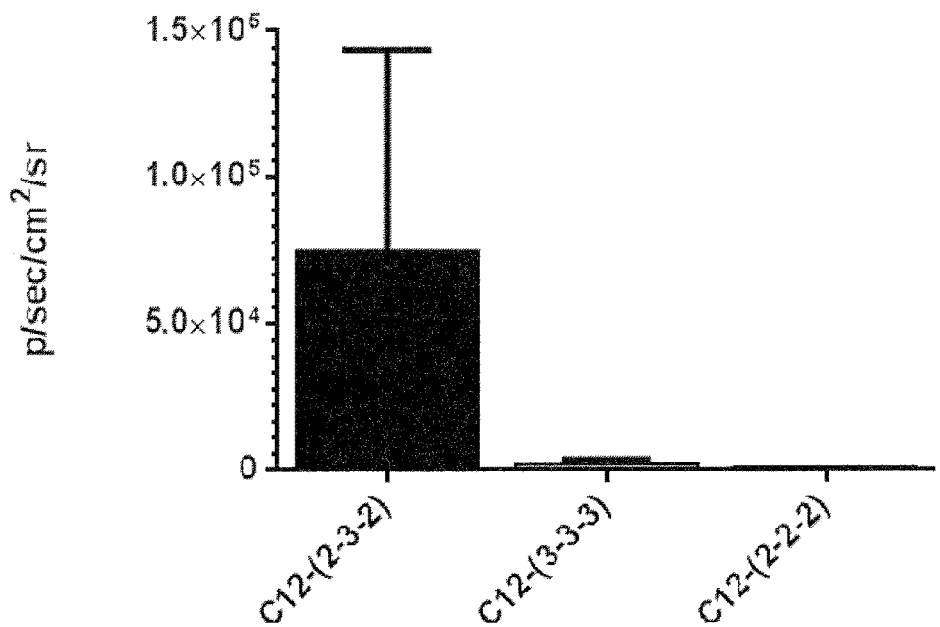
Figure 26
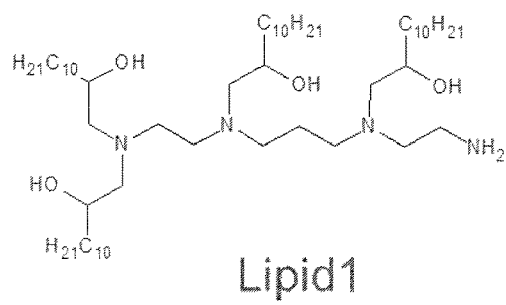
Lipid1
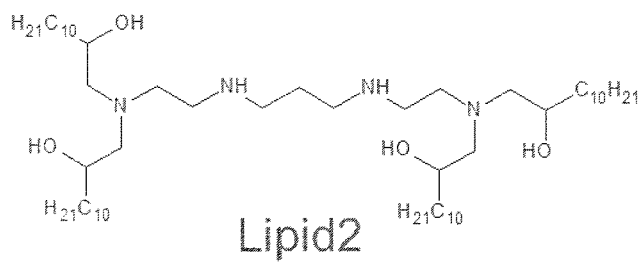
Lipid2
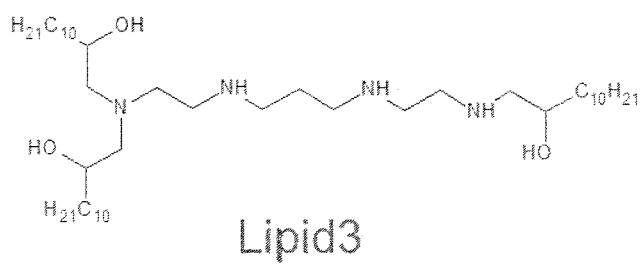
Lipid3
Figure 27 A

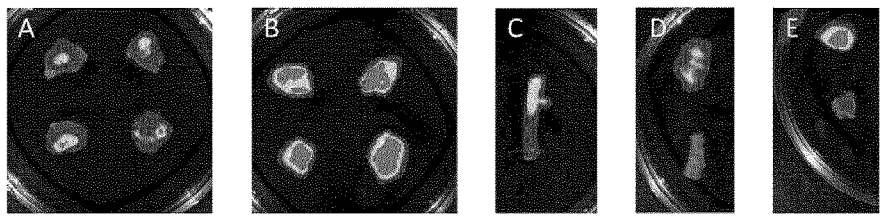
Figure 29
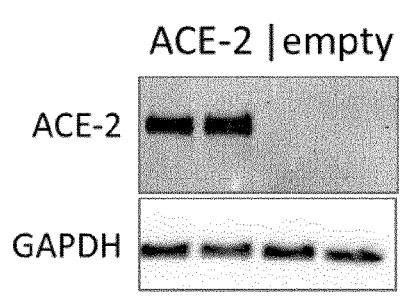
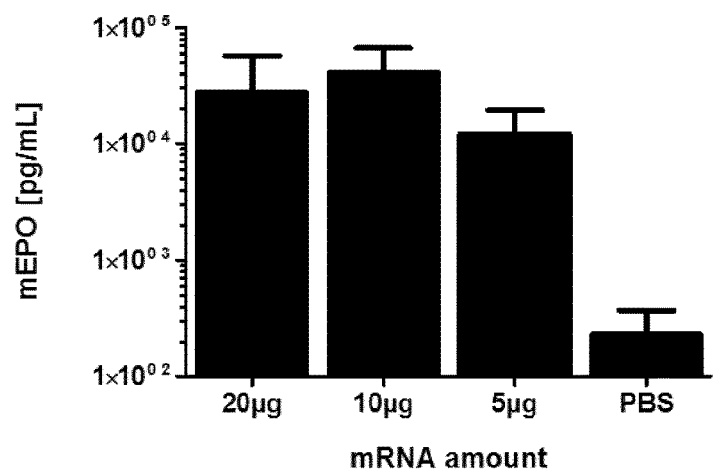
Figure 30
Figure 31

COMPOSITIONS FOR INTRODUCING RNA INTO CELLS

CROSS-REFERENCE TO RELATED APPLICATIONS

This application is a United States National Stage Application under 35 U.S.C. § 371 of International Application No. PCT/EP2014/063756 (pending), filed Jun. 27, 2014, which claims the benefit of European Application No. 13174390.8 filed Jun. 28, 2013 and European Application No. 13181380.0 filed Aug. 22, 2013. The content of each of the aforementioned patent applications is hereby incorporated by reference in its entirety. International Application No. PCT/EP2014/063756 was published under PCT Article 21(2) in English.

The present invention relates to oligomers, polymers and lipidoids comprising characteristic oligo(alkylene amine) moieties which are useful as vehicles for transfecting a cell with an RNA. The present invention furthermore relates to a composition comprising at least an RNA and an oligomer or polymer or a lipidoid comprising such oligo(alkylene amine) moieties and to a method of transfecting a cell using said composition. Furthermore, the present invention relates to pharmaceutical compositions, uses and a kit.

The feasibility of nucleic acid therapies is ultimately dependent on the availability of efficient methods for delivering nucleic acids into cells.

In nucleic acid delivery in general, the use of naked nucleic acids is suitable and sufficient in some instances to transfect cells (Wolff et al. 1990, Science, 247, 1465-1468). However, in most envisaged practical applications it is advantageous or even necessary to formulate the nucleic acid with at least a second agent that protects the nucleic acid from degradation during delivery and/or facilitates distribution to and in a target tissue and/or facilitates cellular uptake and enables suitable intracellular processing. Such formulations for nucleic acid delivery are referred to as vectors in the scientific literature. A huge variety of compounds for the vectorization of nucleic acids, so-called transfection reagents, have been described previously. These compounds are usually either polycations or compositions comprising cationic lipids or lipid-like compounds such as lipidoids (U.S. Pat. No. 8,450,298). Complexes of nucleic acids with polycations are referred to as polyplexes, those with cationic lipids are referred to as lipoplexes (Felgner et al. 1997, Hum Gene Ther, 8, 511-512). Complexes comprising both a polycation and lipids have been described as well (Li and Huang in "Nonviral Vectors for Gene Therapy", Academic Press 1999, Chapter 13, 295-303). Transfection reagents are used to bind and compact nucleic acids to result in primary complexes in the nanometer size range. In salt-containing media these complexes tend to aggregate, also known as salt-induced aggregation, which can be advantageous for transfection in cell culture or localized administration in vivo (Ogris et al. 1998, Gene Ther, 5, 1425-1433; Ogris et al. 2001, AAPS PharmSci, 3, E21). Aggregation can be avoided and complexes of nucleic acids with transfection reagents can be stabilized by surface shielding with polymers such as poly(ethylene glycol). Shielding is also used to avoid opsonization of and complement activation by nucleic acid complexes with transfection reagents (Finsinger et al. 2000, Gene Ther, 7, 1183-1192). The compaction of nucleic acids by transfection reagents not only protects them against degradation by nucleases but also makes them suitable for cellular uptake by endocytosis. Numerous linear and branched polycations are suitable to bind and compact nucleic acids including but not limited to poly(ethylenimine), poly(amidoamine) dendrimers, poly(2-(dimethylamino)ethyl methacrylate) (pDMAEMA) or cationic derivatives of poly(N-(2-hydroxypropyl)methacrylamide) (pHPMA), poly(beta-amino ester)s (Akinc et al. 2003, Bioconj Chem 14(5):979-88), natural and synthetic cationic poly(amino acids) or peptides such as poly(lysines), histones, HMG proteins or cationic carbohydrates such as chitosans. Besides polymers containing primary-, secondary- and/or tertiary amines mentioned above structures containing guanidyl moieties are an important class of molecules for the purpose of nucleic acid complexation and delivery. Guanidyl modified polymers like arginine based structures (Yamanouchi et al. 2008, Biomaterials 29(22): 3269-77), PAMAM modified with arginine (Son et al. 2013, Bull. Korean Chem. Soc. Vol 34 No. 3) or guadinylated-PEI (Lee et al. 2008, Bull. Korean Chem. Soc. 2008, Vol. 29, No. 3) have highlighted the efficiency of such systems. Especially in case of RNA interaction, the molecular characteristics of the guanidyl moiety exhibits unique binding properties (Calnan et al. 19991, Science 252(5009), 1167-1171). For the generation of such structures methods as reviewed by Katritzky and Rogovoy (Katritzky & Rogovoy 2005, ARKIVOC (iv) 49-87) can be used. Often, polyplexes are further modified to contain a cell targeting or an intracellular targeting moiety and/or a membrane-destabilizing component such as an inactivated virus (Curiel et al. 1991, Proc Natl Acad Sci USA, 88, 8850-8854), a viral capsid or a viral protein or peptide (Fender et al. 1997, Nat Biotechnol, 15, 52-56, Zhang et al. 1999, Gene Ther, 6, 171-181) or a membrane-disruptive synthetic peptide (Wagner et al. 1992, Proc Natl Acad Sci USA, 89, 7934-7938, Plank et al. 1994, J Biol Chem, 269, 12918-12924).

Upon endocytotic uptake, complexes are sequestered into intracellular vesicles such as endosomes and lysosomes where they are exposed to the cellular degradation machinery. Thus, it has been recognized that the escape from intracellular vesicles is essential for efficient functional nucleic acid delivery, a requirement that also applies for functional viral infection (Wagner et al. 1992, Proc Natl Acad Sci USA, 89, 7934-7938, Plank et al. 1994, J Biol Chem, 269, 12918-12924). The mechanisms that nature has evolved for viral infectivity have been mimicked to achieve efficient nucleic acid delivery by synthetic vectors. To this end, amphiphilic membrane-destabilizing peptides such as the INF, GALA and KALA peptides or melittin and melittin derivatives (Boeckle et al. 2006, J Control Release, 112, 240-248) have been used with great success to complement polycationic transfection reagents with endosomal escape functionality (Plank et al. 1998, Adv Drug Deliv Rev, 34, 21-35). In lipoplexes, such functionality is inherent by the ability of their lipid moieties to fuse with cellular membranes (Xu and Szoka 1996, Biochemistry, 35, 5616-5623, Zelphati and Szoka 1996, Proc Natl Acad Sci USA, 93, 11493-11498). Since the pivotal paper by Boussif et al. (Boussif et al. 1995, Proc Natl Acad Sci USA, 92, 7297-7301) it is known that the endosomal escape functionality of polyplexes can be realized by physico-chemical means. When poly(ethylenimine) (PEI) is used as a polycation to form polyplexes, its buffering capacity at acidic pH is sufficient to trigger endosomal escape. It is known that the lumen of endosomes is acidified by a proton pump residing in endosomal membranes (Lafourcade et al. 2008, PLoS One, 3, e2758). This acidification is the trigger for endosomal escape of some viruses such as influenza or adenovirus. The so-called proton sponge theory, supported by experimental evidence, describes the putative mechanistic action of polymers comprising chemical structural features of PEI: A substantial fraction of the aminogroups of PEI are un-protonated at neutral (physiological) pH (Ziebarth and Wang 2010, Biomacromolecules, 11, 29-38). By virtue of the protonated and thus positively charged aminogroups, PEI-like polymers can bind and compact nucleic acids. The unprotonated amines can become protonated at acidic pH, and thus have buffering capacity within endosomes. The endosomal acidification by the proton pump comes with accumulation of chloride ions (Sonawane et al. 2003, J Biol Chem, 278, 44826-44831). In the presence of a buffering molecule such as PEI in the endosomal lumen, the proton pump will shuttle way more protons into the endosomal lumen, along with chloride accumulation, as it would in its absence until the natural acidic endosomal pH is reached. The disproportionate accumulation of ions within the endosomes is thought to lead to an osmotic destabilization of the vesicles, leading ultimately to vesicle rupture and the release of the nucleic acid complex into the cytoplasm.

On the basis of the proton sponge theory, numerous researchers have picked up the structural features of PEI in creating novel polymer libraries comprising amines with buffering capacity at acidic pH. In U.S. Pat. Nos. 7,780,957 and 7,829,657 Kataoka et al. describe polymers based on a poly(glutamic acid) or poly(aspartic acid) backbone where the carboxylic acid side chains are derivatized with amine side chains protonatable at acidic pH. However, the rich structural space of oligo(alkylene amines) containing alternating, non-identical alkylene amine units to serve as transfection-enhancing moieties in polycations has not been explored. In particular, it has not been investigated previously for mRNA transfection.

In contrast, much of the scientific work of Kataoka et al. has focused on poly{N—[N'-(2-aminoethyl)-2-aminoethyl] aspartamide}. In a publication by Uchida et al. (2011, J Am Chem Soc, 133, 15524-15532) the same group has examined a series of N-substituted polyaspartamides possessing repeating aminoethylene units in the side chains of the general formula —($CH_2$—$CH_2$—$NH$)$_m$—H. Interestingly, when the authors examined the efficiency of the polymer family in transfection of plasmid DNA, "a distinctive odd-even effect of the repeating aminoethylene units in the polymer side chain on the efficiencies of endosomal escape and transfection to several cell lines was observed. The polyplexes from the polymers with an even number of repeating aminoethylene units (PA-Es) achieved an order of magnitude higher transfection efficiency, without marked cytotoxicity, than those of the polymers with an odd number of repeating aminoethylene units (PA-Os). This odd-even effect agreed well with the buffering capacity of these polymers as well as their capability to disrupt membrane integrity selectively at endosomal pH, leading to highly effective endosomal escape of the PA-E polyplexes. Furthermore, the formation of a polyvalent charged array with precise spacing between protonated amino groups in the polymer side chain was shown to be essential for effective disruption of the endosomal membrane, thus facilitating transport of the polyplex into the cytoplasm" (Abstract from Uchida et al. 2011, J Am Chem Soc, 133, 15524-15532). Interestingly, when the same group of researchers compared poly(aspartamide) derivatives bearing 1,2-diaminoethane side chains, [PAsp(DET)] versus analogues bearing 1,3-diaminopropane side chains, [PAsp(DPT)], they observed that PAsp(DPT) polyplexes showed a significant drop in the transfection efficacy of plasmid DNA at high N/P ratios due to the progressively increased cytotoxicity with N/P ratio, even though the physicochemical differences to [PAsp (DET)] in particle size and ζ-potential were negligible (Miyata et al. 2008, J Am Chem Soc, 130, 16287-16294). Hence, based on the odd-even rule one would expect that polymers comprising 3 protonatable amino groups and propylene spacer groups would be inferior to PAsp(DET) and that 1,3-diaminopropane-comprising side chains are associated with toxicity problems. Nothing is known about structure-activity relationships of such polymers for mRNA transfection.

Geall and colleagues have described cholesterol-polyamine carbamates with the polyamine moiety having the general formula:

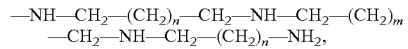

—NH—$CH_2$—($CH_2$)$_n$—$CH_2$—NH—$CH_2$—($CH_2$)$_m$—$CH_2$—NH—$CH_2$—($CH_2$)$_n$—$NH_2$, where m=0, 1 or 2 and where n=0 or 1 (Geall et al. 1999, FEBS Lett, 459, 337-342). They have examined the $pK_a$ values of these substances and their characteristics in condensation of calf thymus DNA. They found that the regiochemical distribution of positive charges along cholesterol polyamine carbamates plays significant roles in modulating DNA binding affinity and lipofection efficiency. They found that among the examined cholesterol-polyamine carbamates, spermine constituting the polyamine moiety, —HN—$CH_2$—$CH_2$—$CH_2$—NH—$CH_2$—$CH_2$—$CH_2$—$CH_2$—NH—$CH_2$—$CH_2$—$CH_2$—$NH_2$ (propyl/butyl/propyl) yielded by far the highest reporter gene expression upon transfection of beta galactosidase-encoding plasmid DNA in cell culture, while for example —HN—$CH_2$—$CH_2$—NH—$CH_2$—$CH_2$—$CH_2$—$NH_2$—$CH_2$—$CH_2$—$NH_2$ (ethyl/propyl/ethyl) was three- to tenfold less efficient. Hence, in view of the teachings of Kataoka et al. (odd-even rule) and the findings of Geall et al. the one skilled in the art would dismiss the latter structure in the context of nucleic acid delivery.

Wang et al. have described poly(methyl methacrylate)-graft-oligoamines as efficient and low cytotoxic transfection reagents for plasmid DNA (Wang et al. 2010, Molecular BioSystems, 6, 256-263). These polymers were obtained by aminolysis of poly(methyl methacrylate) with oligoamines of the general formula $H_2N$—$CH_2$—$CH_2$—(NH—$CH_2$—$CH_2$—$CH_2$)$_m$—$NH_2$, where m=1, 2, or 3. The authors found that transfection efficiency increased with an increasing length of amines.

Ou et al. have described poly(disulphide amido amines) which are derived from terminally protected oligo amines having the structure Dde-NH—($CH_2$)$_a$—NH—($CH_2$)$_b$—NH—($CH_2$)$_a$—NH-Dde by co-polymerization with N,N'-cystaminebisacrylamide (Ou et al. 2009, Biomaterials 30, 5804-5814; WO 2010/065660). They examined the combinations a=2 and b=2, a=2 and b=3, a=3 and b=2, a=3 and b=3, a=3 and b=4 (spermine). Dde is the 2-acetyldimedone protecting group. After removal of the protecting group, the synthesis yields poly(disulphide amido amines) where the internal, originally secondary amines become tertiary amines as part of the polymer main chain and the terminal amines become part of pending ethylene or propylene amine side chains. Such polymers have buffering capacity in the pH range relevant for nucleic acid delivery and are useful for transfecting plasmid DNA into cells.

Recently, the utility of a new class of lipid-like but non-lipidic synthetic structures, so-called lipidoids, for nucleic acid delivery in vitro and in vivo has been discovered (U.S. Pat. No. 8,450,298; Love et al. 2010, PNAS 107, 1864-1869; WO2006/138380; Akinc et al. 2008, Nat Biotechnol 26, 561-569). Lipidoids are obtained by reacting amine-containing compounds with aliphatic epoxides, acrylates, acrylamides or aldehydes. The authors/inventors have provided synthetic procedures for obtaining lipidoid libraries and screening procedures for selecting useful compounds with utility in nucleic acid delivery to cells in vitro.

As is evident from the above, much research and development work has been done in the past on the delivery of other nucleic acid molecules such as plasmid DNA, oligonucleotides, siRNA or nucleic acid analogues. mRNA delivery has not been investigated in much depth. Some authors have alleged that compounds and formulations which work well for DNA or siRNA delivery would work alike for mRNA delivery. However, in contrast to plasmid DNA or siRNA, mRNA is a single-stranded molecule. Hence, based just on structural considerations one would expect different requirements for compounds and formulations for mRNA delivery versus DNA or siRNA delivery.

The previous literature cited above describes the delivery of double-stranded nucleic acids such as plasmid DNA or siRNA into cells but it is not known whether the described methods and compounds are capable of delivering single stranded nucleic acids such as mRNA into cells. Notably, it has been observed previously that mRNA transfection differs substantially from plasmid DNA transfection into cells (Bettinger et al. 2001, Nucleic Acids Res, 29, 3882-91, Uzgün et al, 2011, Pharm Res, 28, 2223-32).

In line with this, the present inventors found that, when screening more than 100 members of a polymer family disclosed in WO 2011/154331 for their suitability in RNA delivery, preferably delivery of single-stranded RNA such as mRNA, to cells, none of the compounds was useful to transfect mRNA in a manner giving rise to the expression of a gene encoded by the mRNA. In contrast, all these compounds are efficient in plasmid DNA and/or siRNA delivery. Hence, the established rules for delivery of double-stranded nucleic acids into cells do not apply a priori for single stranded mRNA. The disclosure of WO 2011/154331 comprises chemically defined oligomers being 2-60 units of oligo(alkylene amino) acid units which correspond to the general formula HOOC—Z—R—NH—[(CH$_2$)$_b$—NH]$_a$—H, where Z is a series of methylene or a variety of other groupings, R is a methylene or carboxy residue and a and b are independently integers of 1-7 or 2-7, respectively. Oligomers of this family comprise protonatable amino groups able to exert a so called proton sponge effect and have been shown to be highly active in the transfection of plasmid DNA and siRNA in vitro and in vivo. Importantly, WO 2011/154331 and associated scientific publications teach in great detail how sequence-defined oligomer/polymer libraries can be established from building blocks corresponding to the general formula HOOC—Z—R—NH—[(CH$_2$)$_b$—NH]$_a$—H.

The technical task underlying the present invention thus was to provide a composition that is suitable for delivery of RNA, preferably single stranded-RNA such as mRNA, with a high efficiency into a cell or to a tissue.

This task has been accomplished by the provision of the embodiments as characterized in the claims and illustrated in further detail in the following general description and the examples. In particular, the invention provides, in its various embodiments as defined further herein:

oligomers, polymers or lipidoids comprising oligo(alkylene amines) containing alternating, non-identical alkylene amine units which are useful for delivering an RNA, preferably a single-stranded RNA such as mRNA, into a cell or to a tissue, compositions comprising these oligomers, polymers or lipidoids comprising oligo(alkylene amines) containing alternating, non-identical alkylene amine units in combination with an RNA and in particular an mRNA which are useful for delivering the RNA, preferably a single-stranded RNA such as mRNA, into a cell or to a tissue, methods for preparing said compounds and compositions, as well as methods using said compounds and compositions for delivering an RNA, preferably a single-stranded RNA such as mRNA, into a cell, as well as medical uses and therapeutic methods which exploit the capability of the compositions in accordance with the invention to deliver an RNA, preferably a single-stranded RNA such as mRNA.

The rich structural space of oligo(alkylene amines) containing alternating, non-identical alkylene amine units in oligomeric or polymeric compounds, including linear, branched and dendritic, random or sequence-defined compounds, or in lipidoid compounds comprised in a composition useful for delivering an RNA, preferably a single-stranded RNA such as mRNA, to a cell has not been explored. Neither has the sequence space of such compounds as such been explored.

It was surprisingly found as a previously unknown general principle for oligomers, polymers, and lipidoids that an arrangement of alkylene amine units of alternating length in groups of three or more units and containing an ethyleneamine unit in compositions for transfecting a cell with an RNA, preferably a single-stranded RNA such as mRNA, was consistently more efficacious than analogous arrangements of alkylene amine units of non-alternating length. Thus, oligomers, polymers or lipidoids were provided which share a common structural entity which is illustrated in formula (I):

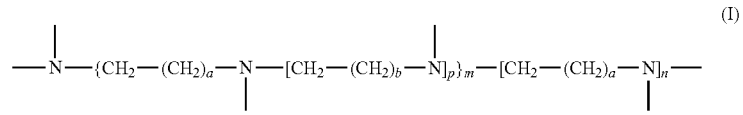

and which will be explained further below.

In particular, the invention provides, in a first aspect, a composition comprising an RNA, preferably a single-stranded RNA such as mRNA, and a component comprising an oligo(alkylene amine) which component is selected from:
a) an oligomer or polymer comprising a plurality of groups of formula (II) as a side chain and/or as a terminal group:

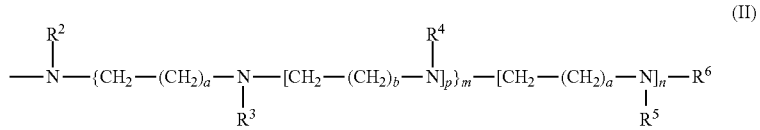

(II)

wherein the variables a, b, p, m, n and $R^2$ to $R^6$ are defined as follows, independently for each group of formula (II) in a plurality of such groups:
a is 1 and b is an integer of 2 to 4; or a is an integer of 2 to 4 and b is 1,
p is 1 or 2,
m is 1 or 2; n is 0 or 1 and m+n is ≥2; and
$R^2$ to $R^5$ are, independently of each other, selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C18 alkyl or C3-C18 alkenyl having one C—C double bond; a protecting group for an amino group; and a poly(ethylene glycol) chain;
$R^6$ is selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C18 alkyl or C3-C18 alkenyl having one C—C double bond; a protecting group for an amino group; —C(NH)—$NH_2$; a poly(ethylene glycol) chain; and a receptor ligand,
and wherein one or more of the nitrogen atoms indicated in formula (II) may be protonated to provide a cationic group of formula (II);
b) an oligomer or polymer comprising a plurality of groups of formula (III) as repeating units:

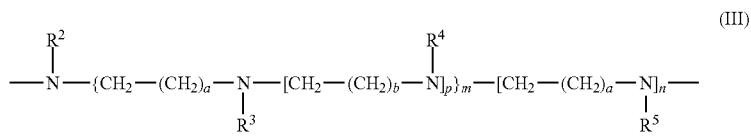

(III)

wherein the variables a, b, p, m, n and $R^2$ to $R^5$ are defined as follows, independently for each group of formula (III) in a plurality of such groups:
  a is 1 and b is an integer of 2 to 4; or a is an integer of 2 to 4 and b is 1,
  p is 1 or 2,
  m is 1 or 2; n is 0 or 1 and m+n is ≥2; and
  $R^2$ to $R^5$ are, independently of each other, selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C18 alkyl or C3-C18 alkenyl having one C—C double bond; a protecting group for an amino group; —C(NH)—$NH_2$; and a poly(ethylene glycol) chain;
and wherein one or more of the nitrogen atoms indicated in formula (III) may be protonated to provide a cationic group of formula (III); and
c) a lipidoid having the structure of formula (IV)):

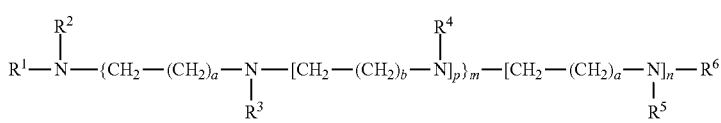

wherein the variables a, b, p, m, n and $R^1$ to $R^6$ are defined as follows:
  a is 1 and b is an integer of 2 to 4; or a is an integer of 2 to 4 and b is 1,
  p is 1 or 2,
  m is 1 or 2; n is 0 or 1 and m+n is ≥2; and
  $R^1$ to $R^6$ are independently of each other selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C18 alkyl or C3-C18 alkenyl having one C—C double bond; a protecting group for an amino group; —C(NH)—$NH_2$; a poly(ethylene glycol) chain; and a receptor ligand; provided that at least two residues among $R^1$ to $R^6$ are a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C18 alkyl or C3-C18 alkenyl having one C—C double bond;
and wherein one or more of the nitrogen atoms indicated in formula (IV) may be protonated to provide a cationic group of formula (IV).

In further aspects, the invention relates to oligomers, polymers or lipidoids as defined above as useful intermediates for the preparation of the compositions in accordance with the invention, and to pharmaceutical compositions comprising the compositions in accordance with the invention. The invention also encompasses methods for the preparation of the oligomers, polymers or lipidoids in accordance with the invention as well as the compositions and pharmaceutical compositions in accordance with the invention.

Still further aspects are directed to the use of a composition in accordance with the invention or a polymer or dendrimer or lipidoid in accordance with the invention for delivering RNA, preferably a single-stranded RNA such as mRNA, into a target cell or to tissue, and to a method for delivering RNA, preferably single-stranded RNA such as mRNA, into a cell comprising the step of bringing a composition in accordance with the invention into contact with the cell.

Oligo(Alkylene Amine) Groups

The oligo(alkylene amine) structures of formulae (II), (III) and (IV) are characterized in that they combine shorter (also referred to for illustration as "S") ethylene amine units (i.e. a or b is 1) with longer (also referred to for illustration as "L") alkylene amine units (i.e. the other one of a or b is an integer of 2 to 4) in an alternating manner. Unexpectedly, this arrangement of the protonatable units has been found to provide advantages in terms of the suitability of the resulting group to provide a vehicle for delivering RNA, preferably single-stranded RNA such as mRNA, into a cell.

As pointed out above, oligomers or polymers which can be used in the compositions in accordance with one preferred embodiment of the invention comprise a plurality of oligo(alkylene amine) groups of formula (II) as a side chain and/or as a terminal group:

—$NR^2${$CH_2$—$(CH_2)_a$—$NR^3$—[$CH_2$—$(CH_2)_b$—$NR^4]_p$}$_m$—[$CH_2$—$(CH_2)_a$—$NR^5]_n$—$R^6$  (II), wherein the variables a, b, p, m, n and $R^2$ to $R^6$ are defined as follows, independently for each group of formula (II) in a plurality of such groups:
  a is 1 and b is an integer of 2 to 4; or a is an integer of 2 to 4 and b is 1,
  p is 1 or 2,
  m is 1 or 2; n is 0 or 1 and m+n is ≥2; and
  $R^2$ to $R^5$ are, independently of each other, selected from hydrogen; a group —$CH_2$—CH(OH)—$R^7$, —CH(R')—$CH_2$—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C18 alkyl or C3-C18 alkenyl having one C—C double bond; a protecting group for an amino group; —C(NH)—$NH_2$; and a poly(ethylene glycol) chain;
  $R^6$ is selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C16 alkyl or C3-C16 alkenyl having one C—C double bond; a protecting group for an amino group; —C(NH)—$NH_2$; a poly(ethylene glycol) chain; and a receptor ligand.
  Preferably, $R^2$ to $R^5$ are hydrogen and $R^6$ is selected from hydrogen, a protecting group for an amino group; —C(NH)—$NH_2$ and a poly(ethylene glycol) chain. More preferably, $R^2$ to $R^6$ are hydrogen. Preferably, $R^7$ is selected from C8-C18 alkyl or C8-C18 alkenyl having one C—C double bond, and more preferably from C8-C12 alkyl or C8-C12 alkenyl having one C—C double bond and most preferably from C10-C12 alkyl or C10-C12 alkenyl having one C—C double bond.

One or more of the nitrogen atoms indicated in formula (II) or its preferred embodiments may be protonated to provide a cationic group of formula (II).

A plurality of groups of formula (II) means that two or more of the groups of formula (II) or its preferred embodiments are contained in the oligomers or polymers in accordance with the invention, preferably three or more. In the polymers containing a plurality of groups of formula (II), it is preferred that 10 or more groups of formula (II) are present. It will be understood that the groups of formula (II) or its preferred embodiments can have the same structure within a polymer or oligomer, or can have two or more different structures within the scope of formula (II).

In accordance with another preferred embodiment, the oligomers or polymers which can be used in the compositions in accordance with the invention comprise a plurality of oligo (alkylene amine) groups of formula (III) as repeating units:

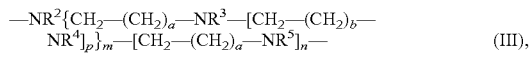

wherein the variables a, b, p, m, n and $R^2$ to $R^5$ are defined as follows, independently for each group of formula (III) in a plurality of such groups:
  a is 1 and b is an integer of 2 to 4; or a is an integer of 2 to 4 and b is 1,
  p is 1 or 2,
  m is 1 or 2; n is 0 or 1 and m+n is ≥2; and
  $R^2$ to $R^5$ are, independently of each other selected from hydrogen; a group —CH$_2$—CH(OH)—R$^7$, —CH(R')—CH$_2$—OH, —CH$_2$—CH$_2$—(C=O)—O—R$^7$, —CH$_2$—CH$_2$—(C=O)—NH—R$^7$ or —CH$_2$—R$^7$ wherein $R^7$ is selected from C3-C18 alkyl or C3-C18 alkenyl having one C—C double bond; a protecting group for an amino group; —C(NH)—NH$_2$; a poly(ethylene glycol) chain; an endosomal escape effector and a receptor ligand. Preferably, $R^2$ to $R^5$ are hydrogen. Preferably, $R^7$ is selected from C8-C18 alkyl or C8-C18 alkenyl having one C—C double bond, and more preferably from C8-C12 alkyl or C8-C12 alkenyl having one C—C double bond and most preferably from C10-C12 alkyl or C10-C12 alkenyl having one C—C double bond.

One or more of the nitrogen atoms indicated in formula (III) or its preferred embodiments may be protonated to provide a cationic group of formula (III).

Optionally, the oligomers or polymers which comprise a plurality of groups of formula (III) or its preferred embodiments as repeating units can comprise, in addition, one or more oligo(alkylene amine) group(s) of formula (II) as a side chain and/or as a terminal group.

A plurality of groups of formula (III) as repeating unit means that two or more of the groups of formula (III) or its preferred embodiments are contained in the oligomers or polymers in accordance with the invention, preferably three or more. Generally, substances comprising 2 to 9 repeating units are referred to herein as oligomers, those comprising 10 and more repeating units as polymers. Thus, in the polymers containing a plurality of groups of formula (III) as repeating units, 10 or more groups of formula (III) are preferably present. It will be understood that the groups of formula (III) or its preferred embodiments can have the same structure within a polymer or oligomer, or can have two or more different structures within the scope of formula (III). Advantageously, and in accordance with a preferred embodiment, the oligomers or polymers containing a plurality of groups of formula (III) as repeating units can be provided in the form of a library of sequence defined polymers which are prepared from different groups of formula (III) in a controlled, stepwise polymerization.

In line with formulae (II) and (III) above, an alkylene amine unit may be repeated once in an alternating chain such that oligo(alkylene amine) moieties of the type —S-L-L-S— or -L-S—S-L- may result, wherein S represents a shorter ethylene amine unit, and L represents a longer alkylene amine unit. However, preferred groups of formula (II) and (III) are those wherein no repetition occurs, i.e. wherein p is 1, such that the shorter or longer units do not appear in pairs. In other words, the group of formula (II) is preferably an oligo(alkylene amine) group of formula (IIa) and the group of formula (III) is preferably an oligo(alkylene amine) group of (IIIa):

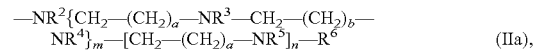

wherein a, b, m, n, and $R^2$ to $R^6$ are defined as in formula (II), including preferred embodiments, and wherein one or more of the nitrogen atoms indicated in formula (IIa) may be protonated to provide a cationic oligomer or polymer structure;

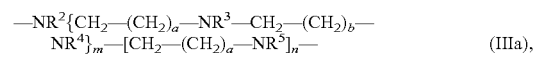

wherein a, b, m, n, and $R^2$ to $R^5$ are defined as in formula (III), including preferred embodiments, and wherein one or more of the nitrogen atoms indicated in formula (IIIa) may be protonated to provide a cationic oligomer or polymer structure.

Moreover, it is generally preferred for the oligo(alkylene amine) group of formulae (II) and (III) that n is 1, and more preferred that m is 1 and n is 1. Thus, it is particularly preferred that the group of formula (II) is an oligo(alkylene amine) group of formula (IIb), and that the group of formula (III) is an oligo(alkylene amine) group of formula (IIIb):

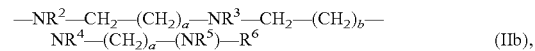

wherein a, b, and $R^2$ to $R^6$ are defined as in formula (II), including preferred embodiments, and wherein one or more of the nitrogen atoms indicated in formula (IIb) may be protonated to provide a cationic oligomer or polymer structure;

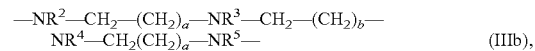

wherein a, b, and $R^2$ to $R^5$ are defined as in formula (III), including preferred embodiments, and wherein one or more of the nitrogen atoms indicated in formula (IIIb) may be protonated to provide a cationic oligomer or polymer structure.

As regards the length of the alkylene amine units in the oligo(alkylene amine) groups of formula (II), (IIa), (IIb) and (III), (IIIa), (IIIb), it will be understood that one of the alternating units needs to be an ethylene amine unit (i.e. either a or b must be 1). The other alternating unit can be a propylene amine unit, a butylene amine unit or a pentylene amine unit (i.e. the other one of a or b is an integer of 2 to 4. Preferably, the other one of a or b is 2 or 3, and most preferably, a is 1 and b is 2, or a is 2 and b is 1. Hence, even more preferred as group (II) is an oligo(alkylene amine) group of formula (IIc), and even more preferred as a group (III) is an oligo(alkylene amine) group of formula (IIIc):

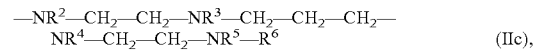

wherein $R^2$ to $R^6$ are as defined in formula (II) and preferred embodiments thereof, and are most preferably hydrogen, and wherein one or more of the nitrogen atoms indicated in formula (IIc) may be protonated to provide a cationic oligomer or polymer structure;

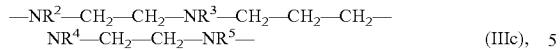

wherein $R^2$ to $R^5$ are as defined in formula (III) and preferred embodiments thereof, and are most preferably hydrogen, and wherein one or more of the nitrogen atoms indicated in formula (IIIc) may be protonated to provide a cationic oligomer or polymer structure.

As far as any of the groups $R^2$ to $R^6$ in formula (II), (IIa), (IIb) and (IIc) or the groups $R^2$ to $R^5$ in formula (III), (IIIa), (IIIb) and (IIIc) are a protecting group for an amino group such as described for example in WO2006/138380, preferred embodiments thereof are t-butoxycarbonyl (Boc), 9-fluorenylmethoxycarbonyl (Fmoc), or carbobenzyloxy (Cbz).

As far as any of the groups $R^1$ to $R^6$ in formula (II), (IIa), (IIb) and (IIc) or the groups $R^2$ to $R^5$ in formula (III), (IIIa), (IIIb) and (IIIc) are a receptor ligand, useful examples are given in Philipp and Wagner in "Gene and Cell Therapy—Therapeutic Mechanisms and Strategy", 3$^{rd}$ Edition, Chapter 15, CRC Press, Taylor & Francis Group LLC, Boca Raton 2009. Preferred receptor ligands for lung tissue are described in Pfeifer et al. 2010, Ther. Deliv. 1(1):133-48. Preferred receptor ligands include synthetic cyclic or linear peptides such as derived from screening peptide libraries for binding to a particular cell surface structure or particular cell type, cyclic or linear RGD peptides, synthetic or natural carbohydrates such as sialic acid, galactose or mannose or synthetic ligands derived from reacting a carbohydrate for example with a peptide, antibodies specifically recognizing cell surface structures, folic acid, epidermal growth factor and peptides derived thereof, transferrin, anti-transferrin receptor antibodies, nanobodies and antibody fragments, approved drugs that bind to known cell surface molecules etc.

As far as any of the groups $R^1$ to $R^6$ in formula (II), (IIa), (IIb) and (IIc) or the groups $R^2$ to $R^5$ in formula (III), (IIIa), (IIIb) and (IIIc) are a poly(ethylene glycol) chain, the preferred molecular weight of the poly(ethylene glycol) chain is 100-20,000 g/mol, more preferably 1,000-10,000 g/mol and most preferred is 1,000-5,000 g/mol.

Most preferred as group (II) is an oligo(alkylene amine) group of formula (IId):

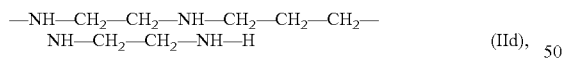

wherein one or more of the nitrogen atoms indicated in formula (IId) may be protonated to provide a cationic polymer or dendrimer structure.

Most preferred as group (III) is an oligo(alkylene amine) group of formula (IIId):

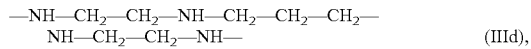

wherein one or more of the nitrogen atoms indicated in formula (IIId) may be protonated to provide a cationic polymer or dendrimer structure.

As pointed out above, lipidoids which can be used in the compositions in accordance with one preferred embodiment of the invention have the structure of formula (IV):

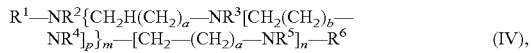

wherein the variables a, b, p, m, n and $R^1$ to $R^6$ are defined as follows:
a is 1 and b is an integer of 2 to 4; or a is an integer of 2 to 4 and b is 1,
p is 1 or 2,
m is 1 or 2; n is 0 or 1 and m+n is ≥2; and
$R^1$ to $R^6$ are independently of each other selected from hydrogen; a group —$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$ or —$CH_2$—$R^7$ wherein $R^7$ is selected from C3-C18 alkyl or C3-C18 alkenyl having one C—C double bond; a protecting group for an amino group; —C(NH)—$NH_2$; a poly (ethylene glycol) chain; and a receptor ligand; provided that at least two residues among $R^1$ to $R^6$ are a group —$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$ or —$CH_2$—$R^7$ wherein $R^7$ is selected from C3-C18 alkyl or C3-C18 alkenyl having one C—C double bond.

Preferably, $R^1$ to $R^6$ are independently selected from hydrogen; a group —$CH_2$—C(OH)H—$R^7$ or —CH($R^7$)—$CH_2$—OH, wherein $R^7$ is selected from C3-C18 alkyl or C3-C18 alkenyl having one C—C double bond; a protecting group for an amino group; and a poly(ethylene glycol) chain; provided that at least two residues among $R^1$ to $R^6$ are a group —$CH_2$—C(OH) H—$R^7$ or —CH($R^7$)—$CH_2$—OH, wherein $R^7$ is selected from C3-C18 alkyl or C3-C18 alkenyl having one C—C double bond. More preferably, $R^1$ to $R^6$ are independently selected from hydrogen; and a group —$CH_2$—CH(OH)—$R^7$ or —CH($R^7$)—$CH_2$—OH wherein $R^7$ is selected from C3-C16 alkyl or C3-C16 alkenyl having one C—C double bond; provided that at least two residues among $R^1$ to $R^6$ are a group —$CH_2$—CH(OH)—$R^7$ or —CH($R^7$)—$CH_2$—OH, wherein $R^7$ is selected from C3-C18 alkyl or C3-C18 alkenyl having one C—C double bond. Even further preferred is the constellation that $R^1$ and $R^6$ are independently selected from hydrogen; and a group —$CH_2$—CH(OH)—$R^7$ or —CH($R^7$)—$CH_2$—OH wherein $R^7$ is selected from C3-C18 alkyl or C3-C18 alkenyl having one C—C double bond; and $R^2$ to $R^5$ are all a group —$CH_2$—CH (OH)—$R^7$ or —CH($R^7$)—$CH_2$—OH wherein $R^7$ is selected from C3-C18 alkyl or C3-C18 alkenyl having one C—C double bond. Preferably, $R^7$ is selected from C8-C16 alkyl or C8-C18 alkenyl having one C—C double bond, and more preferably from C8-C12 alkyl or C8-C12 alkenyl having one C—C double bond and most preferably from C10-C12 alkyl or C10-C12 alkenyl having one C—C double bond.

One or more of the nitrogen atoms indicated in formula (IV) may be protonated to provide a cationic lipidoid of formula (IV).

In line with formula (IV) above, an alkylene amine unit may be repeated once in an alternating chain such that oligo(alkylene amine) moieties of the type —S-L-L-S— or -L-S—S-L- may result, wherein S represents a shorter ethylene amine unit, and L represents a longer alkylene amine unit. However, a preferred lipidoid of formula (IV) is one wherein no repetition occurs, i.e. wherein p is 1, such that the shorter or longer units do not appear in pairs. In other words, the lipidoid of formula (IV) is preferably a lipidoid of (IVa):

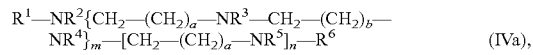

wherein a, b, m, n, and $R^1$ to $R^6$ are defined as in formula (IV), including preferred embodiments, and wherein one or more of the nitrogen atoms indicated in formula (IVa) may be protonated to provide a cationic lipidoid;

Moreover, it is generally preferred for the lipidoid of formula (IV) that n is 1, and more preferred that m is 1 and n is 1. Thus, it is particularly preferred that the lipidoid of formula (IV) is a lipidoid of formula (IVb):

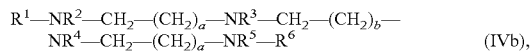

wherein a, b, and $R^1$ to $R^6$ are defined as in formula (IV), including preferred embodiments, and wherein one or more of the nitrogen atoms indicated in formula (IVb) may be protonated to provide a cationic lipidoid.

As regards the length of the alkylene amine units in the lipidoid of formula (IV), (IVa) and (IVb), it will be understood that one of the alternating units needs to be an ethylene amine unit (i.e. either a or b must be 1). The other alternating unit can be a propylene amine unit, a butylene amine unit or a pentylene amine unit (i.e. the other one of a or b is an integer of 2 to 4. Preferably, the other one of a or b is 2 or 3, and most preferably, a is 1 and b is 2, or a is 2 and b is 1. Hence, even more preferred as lipidoid of formula (IV) is a lipidoid of formula (IVc):

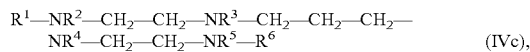

wherein $R^1$ to $R^6$ are as defined in formula (IV) and preferred embodiments thereof, and wherein one or more of the nitrogen atoms indicated in formula (IVc) may be protonated to provide a cationic lipidoid;

As far as the groups $R^1$ to $R^6$ in formula (IV), (IVa), (IVb) and (IVc) are a protecting group for an amino group such as described for example in WO2006/138380, preferred embodiments thereof are t-butoxycarbonyl (Boc), 9-fluorenylmethoxycarbonyl (Fmoc), or carbobenzyloxy (Cbz).

As far as the groups $R^1$ to $R^6$ in formula (IV), (IVa), (IVb) and (IVc) are a receptor ligand, useful examples are given in Philipp and Wagner in "Gene and Cell Therapy—Therapeutic Mechanisms and Strategy", $3^{rd}$ Edition, Chapter 15. CRC Press, Taylor & Francis Group LLC, Boca Raton 2009. Preferred receptor ligands for lung tissue are described in Pfeifer et al. 2010, Ther Deliv. 1(1):133-48. Preferred receptor ligands include synthetic cyclic or linear peptides such as derived from screening peptide libraries for binding to a particular cell surface structure or particular cell type, cyclic or linear RGD peptides, synthetic or natural carbohydrates such as sialic acid, galactose or mannose or synthetic ligands derived from reacting a carbohydrate for example with a peptide, antibodies specifically recognizing cell surface structures, folic acid, epidermal growth factor and peptides derived thereof, transferrin, anti-transferrin receptor antibodies, nanobodies and antibody fragments, approved drugs that bind to known cell surface molecules etc.

As far as the groups $R^1$ to $R^6$ in formula (IV), (IVa), (IVb) and (IVc) are a poly(ethylene glycol) chain, the preferred molecular weight of the poly(ethylene glycol) chain is 100-20,000 g/mol, more preferably 1,000-10,000 g/mol and most preferred is 1,000-5,000 g/mol.

As indicated above, one or more of the nitrogen atoms indicated in formulae (I) and the preferred embodiments thereof including formulae (IIa)-(IId), (IIIa)-(IIId) and (IVa)-(IVc) may be protonated to result in an oligomer or polymer or lipidoid in a cationic form, typically an oligocationic or polycationic form. It will be understood that primary and/or secondary and/or tertiary amino groups in the groups of formula (I) and the preferred embodiments thereof including formulae (IIa)-(IId), (IIIa)-(IIId) and (IVa)-(IVc) can act as proton acceptors, especially in water and aqueous solutions, including physiological fluids. Thus, the oligomers, polymers and lipidoids of the present invention typically have an overall positive charge in an aqueous solution at a pH of below 7.5. An aqueous solution, as referred to herein, is a solution wherein the solvent comprises 50% (vol./vol.) or more, preferably 80 or 90% or more, and most preferably 100% of water. Also, if the compositions in accordance with the invention are in contact with a physiological fluid having a pH of below 7.5, including e.g. blood and lung fluid, the groups of formulae (I) and the preferred embodiments thereof including formulae (IIa)-(IId), (IIIa)-(IId) and (IVa)-(IVc) typically contain one or more protonated amino groups. The $pK_a$ values of these compounds can be determined by acid-base titration using an automated $pK_a$ titrator. The net charge at a given pH value can then be calculated from the Henderson-Hasselbach equation. According to Geall et al. (J. Geall et al. 1998, Chem Commun, 1403-1404), it is important to recognise that any charge is shared across several of the basic centres and that it cannot be attributed to a single point. 1,9-diamino-3,7-diazanonane (propyl/ethyl/propyl)), for example, has $pK_a$s of 9.3, 7.6 and 5.7, meaning that at physiological pH substantial fractions of the aminogroups are in protonated and unprotonated state.

However, as will be understood by the skilled reader, the oligomers, polymers and lipidoids in accordance with the invention as well as the compositions in accordance with the invention may also be provided as a dry salt form which contains the oligomer, polymer or lipidoid in a cationic form.

As will be further understood, counterions (anions) for the positive charges of protonated amino groups in compositions according to the invention comprising an oligomer, polymer or lipidoid and RNA, preferably single-stranded RNA such as mRNA, are typically provided by anionic moieties contained in the RNA. If the positively charged groups are present in excess compared to the anionic moieties in the RNA, positive charges may be balanced by other anions, such as $Cl^-$ or $HCO_3^-$ typically encountered in physiological fluids.

Oligo(alkylene amine)s suitable for use in the context of the present invention can be commercially obtained from known chemical suppliers, or can be synthesized by methods known in the art (e.g. van Alphen 1936, Recueil des Travaux Chimiques des Pays-Bas, 55, 835-840). Any modification which may be necessary can be achieved by standard methods of chemical synthesis.

Oligomer/Polymer Structures

As indicated above, the groups of formulae (I) and the preferred embodiments thereof including formulae (IIa)-(IId) and (IIIa)-(IIId) may be bound to, or may provide a variety of oligomer or polymer backbone structures.

Generally, the oligomer or polymer comprising a plurality of groups of formula (II) or the preferred embodiments thereof including formulae (IIa)-(IId) can also be referred to as a polymer backbone carrying a plurality of groups of formula (II) or the preferred embodiments thereof, including formulae (IIa)-(IId), as a side chain and/or a terminal group. Polymer backbones which may carry a plurality of groups of formula (II) and the preferred embodiments thereof, including the groups of formula (IIa) to (IId), as a side chain or a terminal group include linear, branched or crosslinked polymers as well as dendritic polymers (dendrimers). The polymers include synthetic or bio-polymers. Preferred are linear or branched polymer backbone structures. This applies as well for oligomers which carry the groups of formula (II)

and the preferred embodiments thereof including the groups of formula (IIa) to (IId) as a side chain or a terminal group, the difference being that a polymer backbone typically comprises 10 or more repeating units, whereas an oligomer backbone comprises 2 to 9, preferably 3 to 9 repeating units. Generally, among the oligomers and polymers comprising a plurality of groups of formula (II) and the preferred embodiments thereof, including the groups of formula (IIa) to (IId), as a side chain or a terminal group, polymers are preferred.

The side chains or terminal groups of formula (II) or the preferred embodiments thereof including formulae (IIa)-(IId) can be conveniently grafted to a polymer or oligomer backbone using known chemical functionalities and reactions in order to provide the polymers in accordance with the invention. As will be understood by the skilled reader, the term "grafting to a polymer or oligomer" does not exclude the option that the side chains are bound to the monomers prior to the polymerization reaction. As indicated by the free valence in formula (II), the side chains or terminal groups are attached to the polymer or oligomer backbone via a covalent bond.

It will be further understood that the terms "polymer" and "oligomer" as used herein encompasses polymers and oligomers obtainable by a broad variety of reactions, such as polyaddition, and polycondensation reactions, including radical polymerisation, anionic or cationic polymerisation, as well as polymers and oligomers obtainable by stepwise coupling reactions (e.g. step growth processes).

Thus, polymers or oligomers suitable as polymer or oligomer backbones to carry a plurality of group of formula (II), or its preferred embodiments including formulae (IIa)-(IId), as a side chain or a terminal group include polymers or oligomers such as polyamides, polyesters, polymers with a carbon chain backbone, and polysaccharides. Exemplary polymer or oligomer backbones are provided by poly(amino acids) comprising a plurality of glutamic or aspartic acid units, such as poly(glutamic acid) and poly(aspartic acid), proteins, polyalkynes, polyamines, polyacrylic acid, polymethacrylic acid, polymaleic acid, polysulfonate, polystyrene sulfonate, polyphosphate, pentosan polysulfate, poly (vinyl phosphoric acid), poly(butadiene-co-maleic acid), poly(ethyl acrylate-co-acrylic acid), poly(ethylene-co-acrylic acid), poly(ethylene-co-maleic anhydride), poly(methyl methacrylate-co-methacrylic acid), poly(methyl methacrylate-co-methacrylic acid), poly(styrenesulfonic acid-co-maleic acid), poly(vinyl chloride-co-vinyl acetate-co-maleic acid) carbohydrates such as heparin, heparan sulphate, poly (glucuronic acid), poly(galacturonic acid), hyaluronic acid, poly(uronic acids) in general, or carboxy-terminated dendrimers. Among them, poly(amino acids) comprising a plurality of glutamic or aspartic acid units, such as poly (glutamic acid) and poly(aspartic acid) and poly(meth) acrylic acid are preferred. Most preferred for the purpose of the present invention are polyacrylic acid and polymethacrylic acid.

Preferably, the polymer backbones have a degree of polymerization (in terms of the average number of polymerized units, determined e.g. via gel permeation chromatography (GPC)) of 10 to 10,000, preferably 50 to 5,000.

The polymers in accordance with the invention may be provided by homopolymers or copolymers. Copolymers may contain polymerized units with different structures, such that the polymer backbone is a copolymer. Alternatively, copolymers may be obtained on the basis of a homopolymer as a polymer backbone, wherein not all of the polymerized units carry a group of formula (II), or its preferred embodiments, including formulae (IIa)-(IId). It will be understood that there is also the option of combining these two alternatives by grafting side chains to a certain percentage of the units in a copolymer backbone. Copolymers may be in the form of random, gradient or block copolymers.

If the polymers in accordance with the invention are homopolymers, all polymerized units carry a group of formula (II), or its preferred embodiments, including formulae (IIa)-(IId). If the polymers in accordance with the invention are copolymers, it is preferred that 5 to 100% of all polymerized units carry a group of formula (II), or its preferred embodiments, including formulae (IIa)-(IId), more preferably 25 to 100%, and in particular 50 to 100%. The percentages are given in terms of the number of units carrying a group of formula (II), relative to all polymerized units.

The copolymers above may contain, in addition to the group of formula (II), or its preferred embodiments, including formulae (IIa)-(IId) also other amine containing side chains or terminal groups. However, it is preferred that no side chains or terminal groups of the formula —NH—$(CH_2)_x$—$(NH(CH_2)_2)_y$—$NH_2$, wherein x denotes an integer of 1 to 5 and y denotes an integer of 1 to 5, are contained in the polymers in accordance with the invention.

Preferred polyamides carrying a side chain of formula (II), or its preferred embodiments, including formulae (IIa)-(IId), contain repeating units of the formula (V):

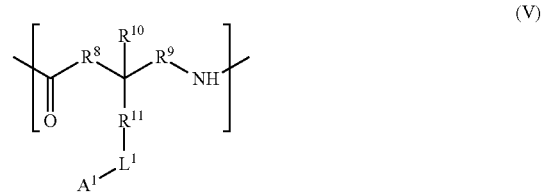

(V)

wherein the variables have the following meanings:
$R^8$ and $R^9$ are independently selected from a bond and C1-C6 alkanediyl;
$R^{10}$ is selected from H and C1-C6 alkyl;
$R^{11}$ is selected from a bond and C1-C6 alkanediyl,
$L^1$ is a divalent linking group, and
$A^1$ represents an oligo(alkylene amine) group of formula (II).

Preferably, $R^8$ and $R^9$ are independently selected from a bond and C1-C5 alkanediyl, and are more preferably a bond. Preferably, $R^{10}$ is selected from H and methyl and is most preferably H.

$R^{11}$ is preferably C1-C6 alkanediyl.

The linking group $L^1$ has, in a preferred embodiment, the structure —$Z^1$—R'—$Z^2$—, wherein $Z^1$ is selected from a bond, —NH—(C=O)—, —NH—C(S)—NH—, —NH—(C=O)—NH—, —NH—S(O)$_2$—, —NH—CH$_2$—C(OH)—, —NH—(C=O)—O—, —NH—C(NH)—, —CH=N—NH—(C=O)—, —S—S—, -thioether bond-, —S—CH$_2$—(C=O)—, —S—, —S—CH$_2$—CH—NH$_2$—, and -aryl thioether bond-; R' is selected from a bond, C1-C6 alkanediyl and —(CH$_2$—CH$_2$—O)$_n$—H with n=1-3; and $Z^2$ is selected from a bond, —(C=O)—, —NH—C(S)—, —NH—(C=O)—, —S(O)$_2$—, —O—P(O)$_2$—, —CH(OH)—CH$_2$, —O—(C=O)— and —C(NH)—. Preferably, $Z^1$ is selected from a bond, —NH—(C=O)—, —NH—(C=O)—NH—, —NH—(C=O)—O—, —NH—C(NH)—; R' is selected from a bond and C1-C6 alkanediyl and $Z^2$ is selected from a bond, —(C=O)—, —NH—

(C=O)—, and —O—(C=O)—; with the proviso that one of $Z^1$ and $Z^2$ is other than a bond. It is most preferred for $L^1$ that $Z^1$ and R' are a bond and $Z^2$ is —(C=O)—, or that $Z^1$ is —NH—(C=O)—, R' is C1-C6 alkanediyl, and $Z^2$ is —(C=O)—.

$A^1$ is preferably one of the preferred embodiments defined herein for the oligo(alkylene amine) group of formula (II), in particular one of the groups of formula (IIa)-(IId).

In the preferred polyamides containing the repeating unit of formula (V), it is preferred that 5 to 100% of all polymerized units are units of formula (V), more preferably 25 to 100%, and in particular 50 to 100%. The percentages are given in terms of the number of units of formula (V), relative to all polymerized units. Within the definitions and preferred definitions given for the variables of formula (V), the repeating units of formula (V) may be the same or different in the preferred polymer in accordance with the invention.

Particularly preferred as polyamide polymers for use in the present invention are the polymers of formula (Va) and (Vb).

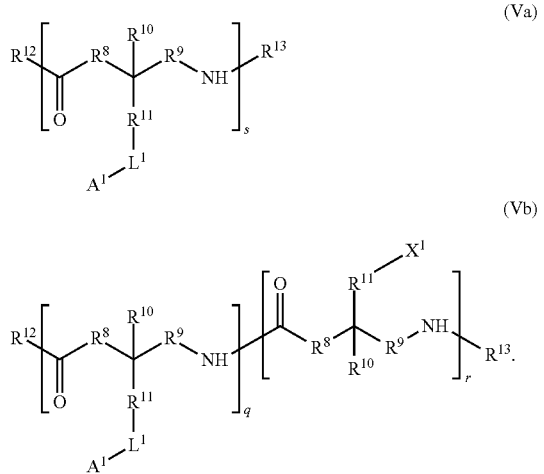

In these formulae, $R^8$, $R^9$, $R^{10}$, $R^{11}$, $L^1$ and $A^1$ are defined as for formula (V), including preferred embodiments thereof. $R^{12}$ is selected from OH or C1-C6 alkoxy, —$NH_2$, a poly(ethylene glycol) chain, or a receptor ligand. $R^{13}$ is H, a protecting group for an amino group, a poly(ethylene glycol) chain, or a receptor ligand $X^1$ is selected from H, —$NH_2$, —COOH and —COOR", with R" being C1-C6 alkyl, a poly(ethylene glycol) chain, or a receptor ligand. In formula (Va), s (indicating the average number of polymerized units, determined e.g. via gel permeation chromatography (GPC)) is 10 to 10,000, preferably 50 to 5,000. In formula (Vb), the units in brackets are repeating units which can be arranged in the polymer in any order, including in particular a random, alternating or blockwise arrangement. The sum of q+r (indicating the average number of polymerized units, determined e.g. via gel permeation chromatography (GPC)) is 10 to 10,000, preferably 50 to 5,000, and the ratio of q/(q+r) ranges from 0.05 to 1, preferably 0.25 to 1, and more preferably from 0.5 to 1.

Exemplary preferred poly(amino acids), which can be conveniently modified by side chains of formula (II) or the preferred embodiments thereof including formulae (IIa)-(IId) are poly(glutamic acid), poly(aspartic acid), polylysine, polyornithine or poly(amino acids) containing glutamic acid, aspartic acid, ornithine and/or lysine units. More preferred is poly(glutamic acid).

Preferred polymers with a carbon chain backbone carrying a side chain of formula (II) or the preferred embodiments thereof, including formulae (IIa)-(IId) contain repeating units of the formula (VI):

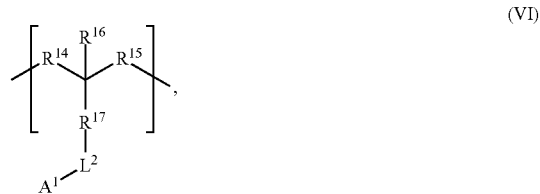

wherein the variables have the following meanings:
$R^{14}$ and $R^{15}$ are independently selected from a bond and C1-C6 alkanediyl;
$R^{16}$ is selected from H and C1-C6 alkyl;
$R^{17}$ is selected from a bond and C1-C6 alkanediyl,
$L^2$ is a divalent linking group, and
$A^1$ represents an oligo(alkylene amine) group of formula (II).

Preferably, $R^{14}$ is a bond and $R^{15}$ is a bond or —$CH_2$—. More preferably, $R^{14}$ is a bond and $R^{15}$ is —$CH_2$—. Preferably, $R^{16}$ is selected from H and methyl. $R^{17}$ is preferably a bond or —$CH_2$—.

The linking group $L^2$ has, in a preferred embodiment, the structure —$Z^3$—R'—$Z^4$—, wherein $Z^3$ is selected from a bond, —NH—(C=O)—, —NH—C(S)—NH—, —NH—(C=O)—NH—, —NH—S(O)$_2$—, —NH—$CH_2$—C(OH)—, —NH—(C=O)—O—, —NH—C(NH)—, —S—S—, —CH=N—NH—(C=O)—, -thioether bond-, —S—$CH_2$—(C=O)—, —S—, —S—$CH_2$—CH—$NH_2$—, and -aryl thioether bond-; R' is selected from a bond, C1-C6 alkanediyl and —($CH_2$—$CH_2$—O)$_n$—H with n=1-3; and $Z^4$ is selected from a bond, —(C=O)—, —NH—C(S)—, —NH—(C=O)—, —S(O)$_2$—, —O—P(O)$_2$—, —CH(OH)—$CH_2$, —O—(C=O)— and —C(NH)—. Preferably, $Z^3$ is selected from a bond, —NH—(C=O)—, —NH—(C=O)—NH—, —NH—(C=O)—O—, —NH—C(NH)—; R' is selected from a bond and C1-C6 alkanediyl and $Z^4$ is selected from a bond, —(C=O)—, —NH—(C=O)—, and —O—(C=O)—; with the proviso that one of $Z^3$ and $Z^4$ is other than a bond. It is most preferred for $L^2$ that $Z^3$ and R' are a bond and $Z^4$ is —(C=O)—.

$A^1$ is preferably one of the preferred embodiments defined herein for the oligo(alkylene amine) group of formula (II), in particular one of the groups of formula (IIa)-(IId).

In the preferred polyamides containing the repeating unit of formula (VI), it is preferred that 5 to 100% of all polymerized units are units of formula (VI), more preferably 25 to 100%, and in particular 50 to 100%. The percentages are given in terms of the number of units of formula (VI), relative to all polymerized units. Within the definitions and preferred definitions given for the variables of formula (VI), the repeating units of formula (VI) may be the same or different in the preferred polymer in accordance with the invention.

Particularly preferred as polymers with a carbon chain backbone carrying the side chains of formula (II), or its preferred embodiments, including formulae (IIa)-(IId), are the polymers of formula (VIa) and (VIb).

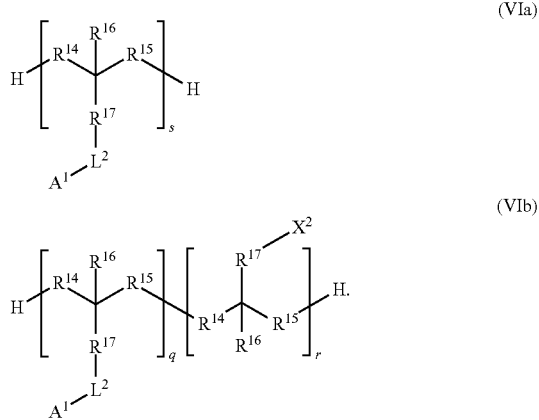

(VIa)

(VIb)

In these formulae, $R^{14}$, $R^{15}$, $R^{16}$, $R^{17}$, $L^2$ and $A^1$ are defined as for formula (VI), including preferred embodiments thereof. $X^2$ is selected —COOH and —COOR", with R" being C1-C6 alkyl, a poly(ethylene glycol) chain, or a receptor ligand. In formula (Via), s (indicating the average number of polymerized units, determined e.g. via gel permeation chromatography (GPC)) is 10 to 10,000, preferably 50 to 5,000. In formula (VIb), the units in brackets are repeating units which can be arranged in the polymer in any order, including in particular a random, alternating or blockwise arrangement. The sum of q+r (indicating the average number of polymerized units, determined e.g. via gel permeation chromatography (GPC)) is 10 to 10,000, preferably 50 to 5,000, and the ratio of q/(q+r) ranges from 0.05 to 1, preferably 0.25 to 1, and more preferably from 0.5 to 1.

Exemplary preferred polymers with a carbon chain backbone, which can be conveniently modified by side chains of formula (II) or the preferred embodiments thereof including formulae (IIa)-(IId) are polyacrylic acid, polymethacrylic acid or polymaleic acid, and more preferred are polyacrylic acid and polymethacrylic acid.

Preferred polysaccharides carrying a side chain of formula (II) or the preferred embodiments thereof, including formulae (IIa)-(IIId), contain repeating units of the formula (VII):

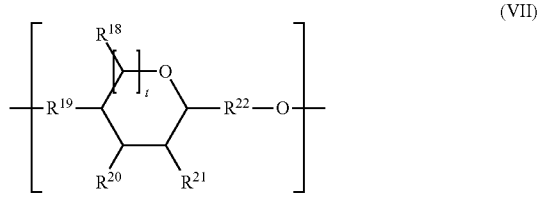

(VII)

wherein the variables have the following meanings:
$R^{19}$ and $R^{22}$ are independently selected from a bond and —(CH)$_2$—; t is 0 or 1;
and one of $R^{18}$, $R^{20}$ and $R^{21}$ represents -$L^3$-$A^1$, wherein $L^3$ is a divalent linking group and A represents an oligo (alkylene amine) group of formula (II), and the other ones are independently selected from —H, —OH, and —(CH$_2$)$_n$—OH, wherein n=1 or 2.
Preferably, $R^{19}$ and $R^{22}$ are a bond. Preferably, one of $R^{18}$, $R^{20}$ and $R^{21}$ represents -$L^3$-$A^1$, wherein $L^3$ is a divalent linking group and $A^1$ represents an oligo(alkylene amine) group of formula (II), and the other ones are —OH.

The linking group $L^3$ has, in a preferred embodiment, the structure —$Z^5$—R'—$Z^6$—, wherein $Z^5$ is selected from a bond, —NH—(C=O)—, —NH—C(S)—NH—, —NH—(C=O)—NH—, —NH—S(O)$_2$—, —NH—CH$_2$—C(OH)—, —NH—(C=O)—O—, —NH—C(NH)—, —S—S, —CH=N—NH—(C=O)—, -thioether bond-, —S—CH$_2$—(C=O)—, —S—, —S—CH$_2$—CH—NH$_2$—, and -aryl thioether bond-; R' is selected from a bond, C1-C6 alkanediyl and —(CH$_2$—CH$_2$—O)$_n$—H with n=1-3; and $Z^6$ is selected from a bond, —(C=O)—, —NH—C(S)—, —NH—(C=O)—, —S(O)$_2$—, —O—P(O)$_2$—, —CH(OH)—CH$_2$, —O—(C=O)— and —C(NH)—; with the proviso that one of $Z^5$ and $Z^6$ is other than a bond. Preferably, $Z^5$ is selected from a bond, —NH—(C=O)—, —NH—(C=O)—NH—, —NH—(C=O)—O—, —NH—C(NH)—; R' is selected from a bond and C1-C6 alkanediyl and $Z^6$ is selected from a bond, —(C=O)—, —NH—(C=O)—, and —O—(C=O)—; with the proviso that one of $Z^5$ and $Z^6$ is other than a bond. It is most preferred for $L^3$ that $Z^5$ and R' are a bond and $Z^6$ is —(C=O)—.

$A^1$ is preferably one of the preferred embodiments defined herein for the oligo(alkylene amine) group of formula (II), in particular a group of formula (IIa)-(IId).

In the preferred polysaccharides containing the repeating unit of formula (VII), it is preferred that 5 to 100% of all polymerized units are units of formula (VII), more preferably 25 to 100%, and in particular 50 to 100%. The percentages are given in terms of the number of units of formula (VII), relative to all polymerized units. Within the definitions and preferred definitions given for the variables of formula (VII), the repeating units of formula (VII) may be the same or different in the preferred polymer in accordance with the invention.

Particularly preferred as polysaccharides carrying a side chain of formula (II) or the preferred embodiments thereof, including formulae (IIa)-(IId) are the polymers of formula (VIIa).

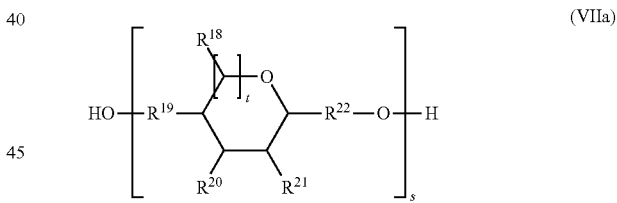

(VIIa)

In this formula, $R^{18}$, $R^{19}$, $R^{20}$, $R^{21}$, $R^{22}$ and t are defined as for formula (VII), including preferred embodiments thereof. s (indicating the average number of polymerized units, determined e.g. via gel permeation chromatography (GPC)) is 10 to 10,000, preferably 50 to 5,000.

Exemplary polymers with a polysaccharide backbone, which can be conveniently modified by the side chains of formula (II) or the preferred embodiments thereof including formulae (IIa)-(IId) are starch, amylose, amylopectin, glycogen, cellulose, dextran, dextrin, cyclodextrin, chitin, chitosan, inulin, Pullulan, Scleroglucan, curdlan, callose, laminarin, chrysolaminarin, xylan, arabinoxylan, mannan, fucoidan and galactomannan, proteoglycans, polyglucuronan, polyglucuronan, cellouronic acid, chitouronic acid, polyuronic acids, pectins, glycosaminoglycans, heparin, heparin sulfate, chondroitin sulfates, dermatan sulfate, hyaluronic acid agar, sodium alginate, alginic acid, Gum Arabic, carrageenan, fucoidan, fucogalactan, chitobiose octaacetate, chitotriose undecaacetate, maltooligosaccharides. Preferred are chitosans, hydroxyethyl starch, dextrans, dextrin, cyclodextrins (α-cyclodextrin, β-cyclodextrin, γ-cyclodextrin, and δ-cyclodextrin).

Various dendrimer structures which can be modified to contain a plurality of terminal groups of formula (II) or the preferred embodiments thereof including formulae (IIa)-(IId) in their branched structures are known in the art, and are described e.g. polyamidoamines (PAMAM) (Tomalia et al. 1990, Angew. Chem. Int. Edn. Engl. 29, 138-175) or fractured PAMAM (Tang et al, 1996, Bioconjug. Chem. 7, 703-714), polyamines (Hawker et al. 1990, J. Am. Chem. Soc. 112, 7638-7647), polyamides (polypeptides) (Sadler et al. 2002, J. Biotechnol. 90, 195-229), poly(aryl ethers) (Hawker et al. 1990, J. Am. Chem. Soc. 112, 7638-7647), polyesters (Ihre et al. 1996, J. Am. Chem. Soc. 118, 6388-6395, Grinstaff et al. 2002, Chemistry 8, 2838-2846), carbohydrates (Turnbull et al. 2002, J. Biotechnol. 90, 231-255), DNA (Nilsen et al. 1997, J. Theor. Biol. 187, 273-284, Li et al., 2004, Nat. Mater. 3, 38-42), lipids (Ewert et al. 2006, Bioconjug Chem. 17, 877-88), poly(ether imine) (Thankappan et al. 2011, Bioconjug Chem. 22, 115-9.) triazine (Lim et al. 2012, Adv Drug Deliv Rev. 15, 826-35) and polyglycerols (Fischer et al. 2010, Bioconjug Chem. 21, 1744-52).

It will be understood that oligomers comprising a plurality of groups of formula (II) or preferred embodiments thereof, including formulae (IIa)-(IId) as terminal groups also encompass oligomers wherein a plurality of such groups are covalently attached as terminal groups to a polyfunctional core structure which provides suitable functional groups for the attachment of a plurality of groups of formula (II) or preferred embodiments thereof, including formulae (IIa)-(IId). These polyfunctional core structures include in particular divalent, trivalent or higher valent carboxylic acids or polyamines. If necessary, the functional groups of the polyfunctional core structures may be activated or reacted with a linking group in order to allow the attachment of groups of a group of formula (II) or a preferred embodiment thereof, including formula (IIa)-(IId) Exemplary branched core structures which can be modified to carry a plurality of such groups are illustrated by formulae (VIIIa-g) below:

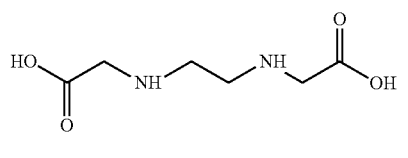
(VIIIa)

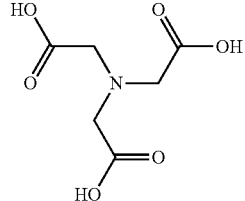
(VIIIb)

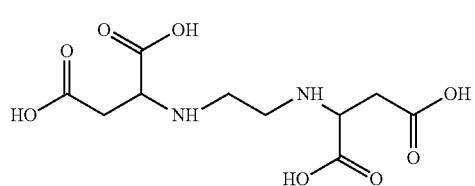
(VIIIc)

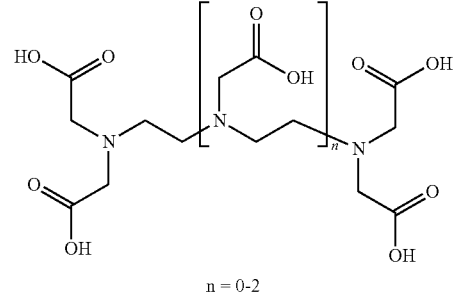
(VIIId)

n = 0-2

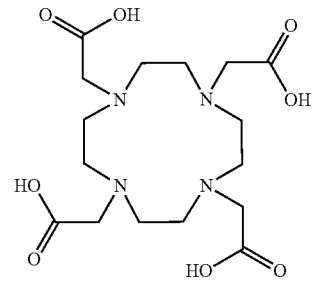
(VIIIe)

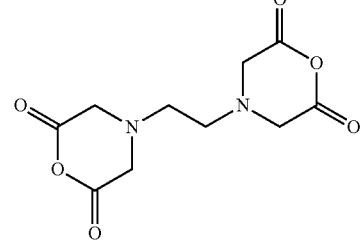
(VIIIf)

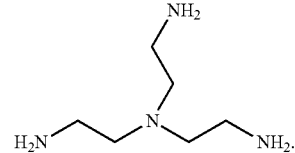
(VIIIg)

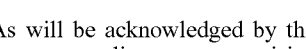

As will be acknowledged by the one skilled in the art, polymers or oligomers comprising the group (II) or its preferred embodiments, including formulae (IIa)-(IId) as a side chain and/or a terminal group can be easily obtained by a variety of synthetic routes via coupling oligo(alkylene amines) to polymer backbones which comprise or have been modified to comprise functional groups amenable to coupling chemistry. Such functional groups include —COOH, —CO—, —CHO, —SO$_3$H, —PO$_4$H, —NH—, —NH$_2$, —OH, or —SH. As will be understood, it may also be possible to modify suitable monomers with the groups of formula (II) prior to their polymerisation to provide the polymers or oligomers in accordance with the invention which contain a side chain and/or terminal group of formula (II). However, the modification of a polymer is generally preferred.

For example, parent polymers (i.e. the polymers providing the polymer backbone in the polymers in accordance with the invention) comprising carboxylic acid groups are amenable to direct coupling, where necessary by activation e.g. using carbodiimide and subsequent amide bond formation with an oligo(alkylene amine) of formula (pre-II) below, wherein the variables a, b, p, m, n and $R^2$ to $R^6$ are defined as for formula (II) to provide the side chains and/or terminal groups of formula (II).

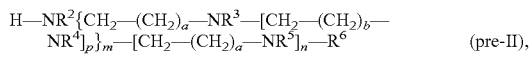

$$\text{H—NR}^2\{\text{CH}_2\text{—(CH}_2)_a\text{—NR}^3\text{—[CH}_2\text{—(CH}_2)_b\text{—} \\ \text{NR}^4]_p\}_m\text{—[CH}_2\text{—(CH}_2)_a\text{—NR}^5]_n\text{—R}^6 \quad \text{(pre-II)},$$

If necessary, the compound of formula (pre-II) may be protected at one or all of its terminal and/or internal secondary amino groups using a conventional protecting group for an amino group such as described for example in WO2006/138380, preferably t-butoxycarbonyl (Boc), 9-fluorenylmethoxycarbonyl (Fmoc), or carbobenzyloxy (Cbz).

Such reactions are preferably conducted in presence of an excess of reactive amino groups of the oligo(alkylene amine) of formula (pre-II) over the carboxylic acid groups of the parent polymer if cross-linking reactions are not desired. Dependent on the nature of the parent polymer, the coupling reaction can be conducted in aqueous or organic solvents. Suitable coupling conditions are well known in the art of peptide and bioconjugate chemistry (Greg T. Hermanson, Bioconjugate Techniques, 2$^{nd}$ Edition, Academic Press 2008). As noted above, suitable polymer backbones include, but are not limited to poly(amino acids) comprising a plurality of glutamic or aspartic acid units, such as poly(glutamic acid) and poly(aspartic acid), proteins, polyalkynes, polyamines, polyacrylic acid, polymethacrylic acid, polymaleic acid, polysulfonate, polystyrene sulfonate, polyphosphate, pentosan polysulfate, poly(vinyl phosphoric acid), poly(butadiene-co-maleic acid), poly(ethyl acrylate-co-acrylic acid), poly(ethylene-co-acrylic acid), poly(ethylene-co-maleic anhydride), poly(methyl methacrylate-co-methacrylic acid), poly(methyl methacrylate-co-methacrylic acid), poly(styrenesulfonic acid-co-maleic acid), poly(vinyl chloride-co-vinyl acetate-co-maleic acid) carbohydrates such as heparin, heparan sulphate, poly(glucuronic acid), poly(galacturonic acid), hyaluronic acid, poly(uronic acids) in general, or carboxy-terminated dendrimers.

For other embodiments of the present invention, the polymer comprising side chains and/or terminal groups of formula (II) can be obtained by reductive amination of a parent polymer. Carbohydrates or sugars can be oxidized to aldehydes, followed by reaction with an oligo(alkylene amine) leading to an imine which can be reduced for example with sodium cyano borohydride to result in an amine.

For yet a further embodiment of the present invention, an oligo(alkylene amine) can be derivatized in a first step to result in a carboxy-terminated oligo(alkylene amine) e.g. of formula (pre-II') which is amenable to coupling to hydroxyl and amino groups in a parent polymer:

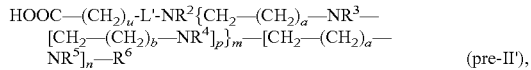

$$\text{HOOC—(CH}_2)_u\text{-L'-NR}^2\{\text{CH}_2\text{—(CH}_2)_a\text{—NR}^3\text{—} \\ [\text{CH}_2\text{—(CH}_2)_b\text{—NR}^4]_p\}_m\text{—[CH}_2\text{—(CH}_2)_a\text{—} \\ \text{NR}^5]_n\text{—R}^6 \quad \text{(pre-II')},$$

wherein u is an integer of 1 to 6, L' is a bond or —(CH)$_2$—, and the other variables are defined as for formula (II). If necessary, any terminal and/or internal secondary amino group(s) in the compound of formula (pre-II) or (pre-III') may be protected using a conventional protecting group for an amino group such as described for example in WO2006/138380, preferably t-butoxycarbonyl (Boc), 9-fluorenylmethoxycarbonyl (Fmoc), or carbobenzyloxy (Cbz).

For this purpose, the oligo(alkylene amine) can be reacted with a dicarboxylic acid anhydride, a dicarboxylic acid or an aldehyde resulting in structure (pre-II'). Even though the structure (pre-III') can be obtained without providing the amines in oligo(alkylene amine) (pre-II) with orthogonal protecting groups, it can be preferable to do so. Structure (pre-II') allows the modification of e.g. poly(lysine), poly(ornithine) or poly(vinylamine) by direct coupling, resulting in amide bond formation. Upon completion of the coupling reaction, any protecting groups can be removed via conventional methods. The resulting polymer can then be purified e.g. by dialysis or ion exchange or size exclusion or reverse phase or hydrophobic interaction chromatography.

Intermediate and final products can be purified by precipitation, dialysis or size exclusion chromatography after the amine protecting groups have been removed, and before the final coupling step in the case of dendrimers.

Polymers or oligomers containing a plurality of repeating units of formula (III) or preferred embodiments thereof, including formulae (IIIa)-(IId) can be linear, branched, or crosslinked polymers, or dendritic polymers (dendrimers). Preferably, the polymers or oligomers containing a plurality of repeating units of formula (III) or preferred embodiments thereof, including formulae (IIIa)-(IIId) contain at least 25%, more preferably at least 40% of such repeating units, in terms of the number of units of formula (III) relative to the total number of repeating units in the polymer or oligomer. It is especially preferred that 50% or more of all repeating units in the polymers or oligomers containing a plurality of repeating units of formula (III) or preferred embodiments thereof, including formulae (IIIa)-(IIId), are such units. The remaining repeating units being provided by molecules which allow the coupling of the repeating units of formula (III) or preferred embodiments thereof, including formulae (IIIa)-(IIId), in particular units derived from divalent, trivalent or higher valent carboxylic acids.

Polymers or oligomers containing a plurality of repeating units of formula (III) or preferred embodiments thereof, including formulae (IIIa)-(IIId) may be conveniently obtained using a compound of formula (pre-II):

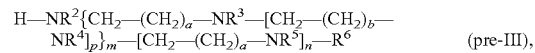

$$\text{H—NR}^2\{\text{CH}_2\text{—(CH}_2)_a\text{—NR}^3\text{—[CH}_2\text{—(CH}_2)_b\text{—} \\ \text{NR}^4]_p\}_m\text{—[CH}_2\text{—(CH}_2)_a\text{—NR}^5]_n\text{—R}^6 \quad \text{(pre-III)},$$

where "pre" indicates formula (pre-III) being a precursor of formula (III) and wherein the variables a, b, p, m, n and R$^2$ to R$^5$ are defined as for formula (III), and R$^6$ is defined as for formula (II), including preferred embodiments thereof, or preferably using a compound of formulae (pre-IIIa)-(pre-IIId), wherein the variables are defined as in formula (IIIa), (IIIb) (IIIc) or (IIId), respectively:

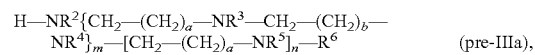

$$\text{H—NR}^2\{\text{CH}_2\text{—(CH}_2)_a\text{—NR}^3\text{—CH}_2\text{—(CH}_2)_b\text{—} \\ \text{NR}^4]_m\text{—[CH}_2\text{—(CH}_2)_a\text{—NR}^5]_n\text{—R}^6 \quad \text{(pre-IIIa)},$$

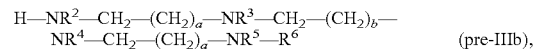

$$\text{H—NR}^2\text{—CH}_2\text{—(CH}_2)_a\text{—NR}^3\text{—CH}_2\text{—(CH}_2)_b\text{—} \\ \text{NR}^4\text{—CH}_2\text{—(CH}_2)_a\text{—NR}^5\text{—R}^6 \quad \text{(pre-IIIb)},$$

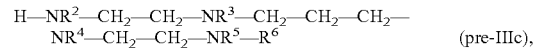

$$\text{H—NR}^2\text{—CH}_2\text{—CH}_2\text{—NR}^3\text{—CH}_2\text{—CH}_2\text{—CH}_2\text{—} \\ \text{NR}^4\text{—CH}_2\text{—CH}_2\text{—NR}^5\text{—R}^6 \quad \text{(pre-IIIc)},$$

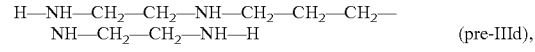

$$\text{H—NH—CH}_2\text{—CH}_2\text{—NH—CH}_2\text{—CH}_2\text{—CH}_2\text{—} \\ \text{NH—CH}_2\text{—CH}_2\text{—NH—H} \quad \text{(pre-IIId)},$$

These compounds carrying terminal amine groups can be linked to form linear, branched, crosslinked or dendritic polymers using conventional coupling reactions. Suitable compounds which can be used as reactants in such coupling reactions include divalent, trivalent or higher valent carboxylic acids. Exemplary compounds which are commercially available and which can be reacted with the linker compounds of formula (pre-III), (pre-IIIa), (pre-IIIb), (pre-IIIc) and (pre-IIId), respectively, are illustrated by formulae (VIIIa-g) below:

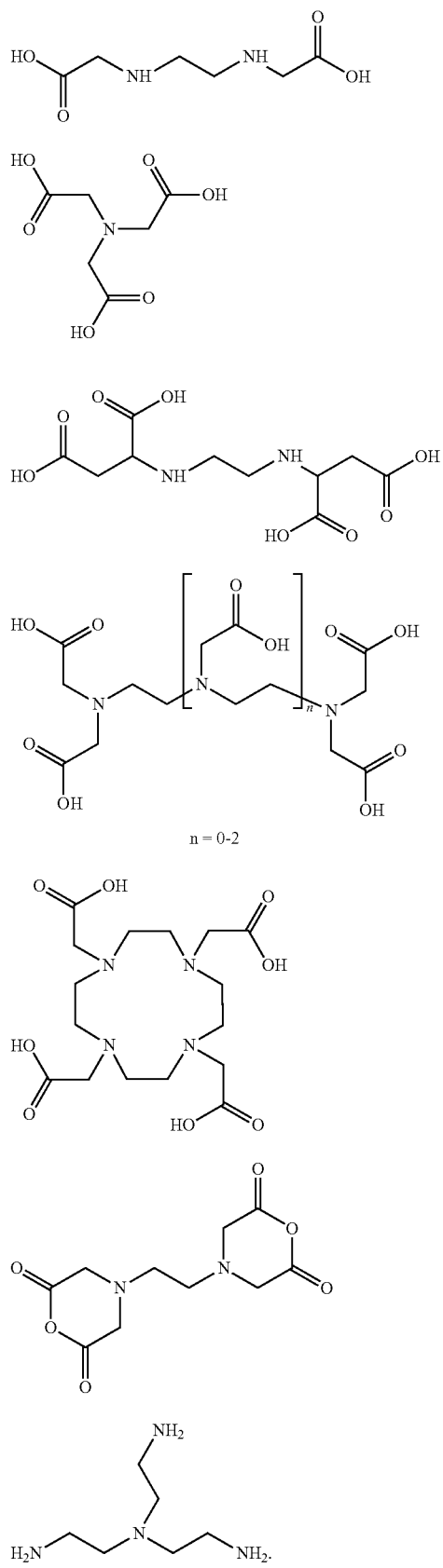

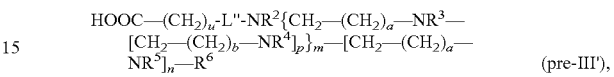

While the direct reaction of polyvalent carboxylic acids with diamines can be conveniently accomplished, it will be understood that linker compounds are not limited to those providing carboxylic acid groups (or activated forms thereof). For example, the compound of formula (VIIIg) can be reacted with a compound of formula (pre-III) after a di-amide of the compound of formula (pre-III) has been formed with a dicarboxylic acid, such as succinic acid.

Also, an oligo(alkylene amine) can be derivatized in a first step to result in a carboxy-terminated oligo(alkylene amine) of formula (pre-III'), e.g. as described above for the preparation of compounds of formula (pre-III):

$$HOOC-(CH_2)_u-L''-NR^2\{CH_2-(CH_2)_a-NR^3-[CH_2-(CH_2)_b-NR^4]_p\}_m-[CH_2-(CH_2)_a-NR^5]_n-R^6 \quad \text{(pre-III')},$$

wherein u is an integer of 1 to 6, L" is a bond or $-(CH)_2-$, and the other variables are defined as for formula (III), and $R^6$ is defined as for formula (II). If necessary, any internal secondary amino group(s) in the compound of formula (pre-III') may be protected using a conventional protecting group for an amino group such as described for example in WO2006/138380, preferably t-butoxycarbonyl (Boc), 9-fluorenylmethoxycarbonyl (Fmoc), or carbobenzyloxy (Cbz). If the remaining terminal amino group $-NR^5R^6$ is present in an unprotected form/in a form which allows the amide formation with a carboxylic acid group, compounds of formula (pre-III') can be polymerized or oligomerized to provide an oligomer or polymer which comprises a plurality of oligo(alkylene amine) groups of formula (III), or preferred embodiments including formulae (IIIa)-(IIId) as repeating units. Such polymers can be linear or branched.

For example, structure (pre-III') can be used to form branched structures either by random polymerization or in a defined way. The co-polymerization can be activated in situ in a mixture of oligo(alkylene amine), optionally with protected internal amino groups and poly-carboxylic acid (VIIIa-VIIIg) in aqueous or organic solvent by carbodiimide activation.

Dendrimers containing a plurality of groups of formula (III) or its preferred embodiments, including formulae (IIIa)-(IIId) as repeating units may also be prepared, e.g. using polyvalent coupling molecules. A dendrimer is a polymeric molecule composed of multiple perfectly branched monomers that emanate radially from a central core, reminiscent of a tree, whence dendrimers derive their name (Greek, dendra). When the core of a dendrimer is removed, a number of identical fragments called dendrons remain, the number of dendrons depending on the multiplicity of the central core (2, 3, 4 or more). A dendron can be divided into three different regions: the core, the interior (or branches) and the periphery (or end or terminal groups). The number of branch points encountered upon moving outward from the core of the dendron to its periphery defines its generation (G-1, G-2, G-3); dendrimers of higher generations are larger, more branched and have more end groups at their periphery than dendrimers of lower generations.

The synthesis can be either divergent, which results in an exponential-like growth, or convergent, in which case dendrons are grown separately and attached to the core in the final step. Dendrimers are prepared in a stepwise fashion, similar to the methods used for solid-phase polypeptide and oligonucleotide syntheses, and therefore the products are theoretically monodisperse in size, as opposed to traditional polymer syntheses where chain growth is statistical and polydisperse products are obtained. A monodisperse product is extremely desirable not only for synthetic reproducibility, but also for reducing experimental and therapeutic variability. In practice, a monodisperse product can be easily obtained for low-generation dendrimers (up to G-3), but sometimes at higher generations the inability to purify perfect dendrimers from dendrimers with minor defects that are structurally very similar results in a deviation from absolute monodispersity, albeit typically a slight one.

Preferred dendrimers as polymers in accordance with the present invention which comprise a plurality of oligo(alkylene groups) of formula (III) or preferred embodiments thereof, including formulae (IIIa)-(IIId), have a number of generations ranging from G1 to G10, more preferably from G2-G8 and in particular from G3-G6. The molecular weight of these dendrimers (as it can be calculated on the basis of the reactants combined in the reaction steps) preferably ranges from 1,500 to 1,000,000, more preferably from 3,000 to 230,000, in particular from 6,000 to 60,000 and most preferably from 15,000 to 30,000.

For the production of defined poly(amido amine) dendrimers (protected) structures (pre-III) and/or (pre-III') can be used for the stepwise generation of a branched core as already described in the literature (e.g. Lee et al. 2005, Nat Biotechnol 23, 1517-1526). As starter molecule either an oligo(alkyl amine) (e.g. pre-III) activated by a di-carboxylic acid, anhydride or acrylic acid or a poly-carboxylic acid (e.g. VIIIa-VIIIg) can be used. This core is used to stepwise react it with a oligo(alkyl amine) of structure (pre-III) followed by purification and activation of the terminal amino groups e.g. by acrylic acid. After purification this core can be used to add an additional layer of oligo(alkylene amine)s. Reaction conditions for obtaining dendrimers have been described in detail in the literature (see for example Lee et al., loc. cit. and the references comprised therein).

In accordance with further embodiments, oligo(alkylene amine)s terminated on both sides with a carboxy group can be protected on one side, and/or the internal amines can be protected, if necessary, and can be copolymerized with a diamine or dendritic starter structure having amine groups at the terminals, or with the oligo(alkylene amine) itself.

Intermediate and final products can be purified by precipitation, dialysis or size exclusion chromatography after the amine protecting groups have been removed, and before the final coupling step in the case of dendrimers.

In yet a further embodiment, oligo(alkylene amine)s having a terminal carboxy group (or a suitably protected or activated form thereof) and a terminal amino group (or a suitably protected form thereof), e.g. oligo(alkylene amines) of formula (pre-III') can be used for the stepwise generation of a fully defined peptidic linear or branched structure, similarly as described in WO 2011/154331 and in (Schaffert et al. 2011, Angew Chem Int Ed Engl 50(38), 8986-9). A stepwise reaction can be carried out according to the principles of peptide chemistry and can be conducted on an automated peptide synthesizer. As known to the one skilled in the art of peptide synthesis, di-amino acids such as lysine or ornithine, can be used to build up branched structures. Hence, a large variety of linear and branched homopolymers, but also of heteropolymers comprising different oligo(alkylene amine)s of formula (I) at desired positions of the polymer, can be provided. In addition, canonical amino acids can be incorporated into such defined structures at any position.

For the preparation of the lipidoids of formula (IV), and preferred embodiments thereof, including formula (IVa), (IVb) and (IVc), methods can be employed which are analogous to those described in US 2010/0331234 A1, U.S. Pat. No. 8,450,298; Love et al. 2010, PNAS 107, 1864-1869; WO2006/138380; Akinc et al. 2008, Nat Biotechnol 26, 561-569.

For example, lipidoids of formula (IV), and preferred embodiments thereof, including formulae (IVa), (IVb) and (IVc) can be derived by reacting $R^7$-epoxide or $R^7$—O—(C=O)—CH=CH$_2$ or $R^7$—NH—(C=O)—CH=CH$_2$ or $R^7$—(C=O)—H, with an oligo(alkylene amine) of formula (pre-IV)

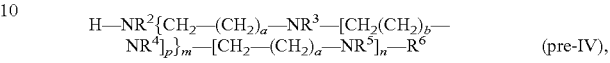  (pre-IV), wherein the variables a, b, p, m, n are defined as in formula (IV) and $R^2$ to $R^6$ are independently of each other hydrogen or a protecting group for an amino group and $R^7$ is selected from C3-C18 alkyl or C3-C18 alkenyl having one C—C double bond. Preferably, $R^7$ is C8-C16 alkyl or alkenyl, more preferably C8-C12 alkyl or alkenyl and most preferred C10-C12 alkyl or alkenyl.

Advantageously, numerous aliphatic compounds terminated on one end with an epoxide, an acrylate, an acrylamide of an aldehyde are commercially available.

Preferably, the lipidoid of formula (IV) is prepared from the oligo(alkylene amine) (pre-IV')

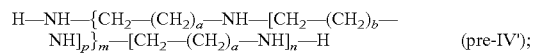  (pre-IV');

More preferably, precursors of formula (pre-IV) have four or more amino groups. Most preferably, the lipidoid of formula (IV) is prepared from the oligo(alkylene amine) (pre-IV")

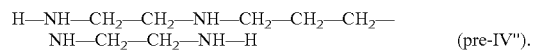  (pre-IV").

The reaction can be carried out with or without solvent at elevated temperature between 500° C. and 90° C. Suitable solvents are for example CH$_2$Cl$_2$, CH$_2$Cl$_3$, methanol, ethanol, THF, hexanes, toluence, benzene etc.

It is known to the one skilled in the art that nitrogens in an oligo(alkylene amine) of formula (pre-IV')

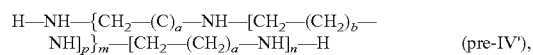  (pre-IV'), can be provided with orthogonal protecting groups such as described for example in WO2006/138380. A protecting group in this context is suitable to temporarily block one or several nitrogens in a compound of formula (pre-IV') such that a reaction can be carried out selectively at other, non-protected nitrogens within the same molecule. After the reaction, to protecting group is removed by a chemical reaction that does not affect other residues linked to nitrogen atoms within the same molecule. Orthogonal protecting groups are different protecting groups which can be removed selectively by chemical reactions affecting specifically one type of protecting group within a given molecule. For example, as described in the Examples, the primary terminal amino groups in an oligo(alkylene amine) of formula (pre-IV') can be selectively protected with the 9-fluorenyl-methoxycarbonyl (Fmoc) protecting group while the internal secondary amines can be protected with the t-butoxycarbonyl (Boc), protecting group. The Fmoc group can be removed selectively by a base, the Boc protecting group by an acid. Protected and partially protected intermediates can be separated by chromatography. Thus, by virtue of a defined positioning and/or selective removal of orthogonal protecting groups it is possible, for example, to selectively react either all or parts of the internal secondary aminogroups or all or parts of the two valences of the terminal primary amino groups an oligo(alkylene amine) of formula (pre-IV') with aliphatic chains terminated on one end with an epoxide or an acrylate or an acrylamide. By virtue of the same principle it is possible to couple more than a single species of $R^7$-epoxide or $R^7$—O—(CO)—CH═CH$_2$ or $R^7$—NH—(CO)—CH═CH$_2$ or $R^7$—(CO)—H to a given oligo(alkylene amine) of formula (pre-IV') with "species" referring to different types of residues $R^7$ in terms of alkyl or alkenyl and in terms of aliphatic chain length and to the terminal epoxide, acrylate, acrylamide or aldehyde. The degree of derivatization of the oligo(alkylene amine) of formula (pre-IV') in such reactions can be controlled by the stoichiometry of the reactants such as described in the previous state of the art. After the removal of protecting groups, the remaining valences of nitrogen atoms can be used to attach a guanidinium group (—C(NH)—NH$_2$), a poly(ethylene glycol) chain or a receptor ligand. Lipidoids of formula (IV) can be purified by precipitation, extraction or chromatography. Based on the option that lipidoids of formula (IV) can be prepared by controlled stepwise reactions with the help of protecting groups and that the degree of derivatization of the oligo (alkylene amine) of formula (pre-IV') can be controlled by the stoichiometry of the reactants, the lipidoid of the present invention can contain primary, secondary, tertiary, and/or quaternary amines, and salts thereof. In consequence, also the $pK_a$ values of the lipidoids can be tuned by rational design of the degree of derivatization such that one or more of the nitrogen atoms in formula (IV) may be protonated to provide a cationic lipidoid of formula (IV) suitable to bind and compact and protect RNA. Furthermore, the $pK_a$ values can be tuned such that one or more of the nitrogen atoms in formula (IV) may have buffering capacity at acidic pH and thus may exert a proton sponge effect upon endocytotic uptake into cells. Preferably, the $pK_a$ values of lipidoids of formula (IV) are between 3.0 and 9.0, more preferably at least one $pK_a$ value is between 5.0 and 8.0.

The maximum number of aliphatic side chains that can be coupled to an oligo(alkylene amine) of formula (pre-IV') in order to obtain a lipidoid of formula (IV) is (p+1)×m+n+3, the minimum number is 1, where p, m and n are defined as in formula (IV). Preferably, the number of aliphatic side chains is at least 2 and at most (p+1)×m+n+2 if none of the residues $R^1$ to $R^6$ is other than hydrogen or —CH$_2$—CH(OH)—$R^7$, —CH($R^7$)—CH$_2$—OH, —CH$_2$—CH$_2$—C(O)—O—$R^7$, —CH$_2$—CH$_2$—C(O)—NH—$R^7$ or —CH$_2$—$R^7$ and preferably the number of aliphatic side chains is at most (p+1)×m+n+1 if one of the residues $R^1$ to $R^6$ is a protecting group for an amino group or —C(NH)—NH$_2$ or a poly(ethylene glycol) chain or a receptor ligand.

Nucleic Acid

The composition of the present invention comprises a nucleic acid, preferably RNA, even more preferably single-stranded RNA such as mRNA.

The term "nucleic acid" encompasses all forms of naturally occurring types of nucleic acids as well as chemically and/or enzymatically synthesized nucleic acids and also encompasses nucleic acid analogues and nucleic acid derivatives such as e.g. locked nucleic acids (LNA), peptide nucleic acids (PNA), oligonucleoside thiophosphates and phosphotriesters, morpholino oligonucleotides, cationic oligonucleotides (U.S. Pat. No. 6,017,700 A, WO/2007/069092), substituted ribo-oligonucleotides or phosphorothioates. Furthermore, the term "nucleic acid" also refers to any molecule that comprises nucleotides or nucleotide analogues. There are no limitations concerning sequence or size of a nucleic acid comprised in the composition of the present invention. The nucleic acid is predominantly defined by the biological effect that is to be achieved at the biological target the composition of the present invention is delivered to. For instance, in the case of an application in gene or nucleic acid therapy, the nucleic acid or nucleic acid sequence can be defined by the gene or gene fragment that is to be expressed or by the intended substitution or repair of a defective gene or any gene target sequence or by the target sequence of a gene to be inhibited, knocked-down or down-regulated.

Preferably, the term "nucleic acid" refers to oligonucleotides or polynucleotides, including deoxyribonucleic acid (DNA) and ribonucleic acid (RNA). As regards RNA, in principle any type of RNA can be employed in the context of the present invention. In one preferred embodiment the RNA is a single-stranded RNA. The term "single-stranded RNA" means a single consecutive chain of ribonucleotides in contrast to RNA molecules in which two or more separate chains form a double-stranded molecule due to hybridization of the separate chains. The term "single-stranded RNA" does not exclude that the single-stranded molecule forms in itself double-stranded structures such as loops, secondary or tertiary structures.

The term "RNA" covers RNA which codes for an amino acid sequence as well as RNA which does not code for an amino acid sequence. It has been suggested that more than 80% of the genome contains functional DNA elements that do not code for proteins. These noncoding sequences include regulatory DNA elements (binding sites for transcription factors, regulators and coregulators etc.) and sequences that code for transcripts that are never translated into proteins. These transcripts, which are encoded by the genome and transcribed into RNA but do not get translated into proteins, are called noncoding RNAs (ncRNAs). Thus, in one embodiment the RNA is a noncoding RNA. Preferably, the noncoding RNA is a single-stranded molecule. Studies demonstrate that ncRNAs are critical players in gene regulation, maintenance of genomic integrity, cell differentiation, and development, and they are misregulated in various human diseases. There are different types of ncRNAs: short (20-50 nt), medium (50-200 nt), and long (>200 nt) ncRNAs. Short ncRNA includes microRNA (miRNA), small interfering RNA (siRNA), piwi-interacting RNA (piRNA), and transcription initiating RNA (tiRNA). Examples of medium ncRNAs are small nuclear RNAs (snRNAs), small nucleolar RNAs (snoRNAs), transfer RNAs (tRNAs), transcription start-site-associated RNAs (TSSaRNAs), promoter-associated small RNAs (PASRs), and promoter upstream transcripts (PROMPTs). Long noncoding RNAs (lncRNA) include long-intergenic noncoding RNA (lincRNA), antisense-lncRNA, intronic lncRNA, transcribed ultra-conserved RNAs (T-UCRs), and others (Bhan A, Mandal S S, ChemMedChem. 2014 Mar. 26. doi: 10.1002/cmdc.201300534). Of the above-mentioned non-coding RNAs only siRNA is double-stranded. Thus, since in a preferred embodiment the noncoding RNA is single-stranded, it is preferred that the noncoding RNA is not siRNA. In another embodiment the RNA is a coding RNA, i.e. an RNA which codes for an amino acid sequence. Such RNA molecules are also referred to as mRNA (messenger RNA) and are single-stranded RNA molecules. The nucleic acids may be made by synthetic chemical and enzymatic methodology known to one of ordinary skill in the art, or by the use of recombinant technology, or may be isolated from natural sources, or by a combination thereof. The oligo- or polynucleotides may optionally comprise unnatural nucleotides and may be single or double or triple stranded. "Nucleic acid" also refers to sense and anti-sense oligo- or polynucleotides, that is, a nucleotide sequence which is complementary to a specific nucleotide sequence in a DNA and/or RNA.

Preferably, the term nucleic acid refers to mRNA and most preferably to modified mRNA.

Messenger RNAs (mRNA) are polymers which are built up of nucleoside phosphate building blocks mainly with adenosine, cytidine, uridine and guanosine as nucleosides, which as intermediate carriers bring the genetic information from the DNA in the cell nucleus into the cytoplasm, where it is translated into proteins. They are thus suitable as alternatives for gene expression.

In the context of the present invention, mRNA should be understood to mean any polyribonucleotide molecule which, if it comes into the cell, is suitable for the expression of a protein or fragment thereof or is translatable to a protein or fragment thereof. The term "protein" here encompasses any kind of amino acid sequence, i.e. chains of two or more amino acids which are each linked via peptide bonds and also includes peptides and fusion proteins.

The mRNA contains a ribonucleotide sequence which encodes a protein or fragment thereof whose function in the cell or in the vicinity of the cell is needed or beneficial, e.g. a protein the lack or defective form of which is a trigger for a disease or an illness, the provision of which can moderate or prevent a disease or an illness, or a protein which can promote a process which is beneficial for the body, in a cell or its vicinity. The mRNA may contain the sequence for the complete protein or a functional variant thereof. Further, the ribonucleotide sequence can encode a protein which acts as a factor, inducer, regulator, stimulator or enzyme, or a functional fragment thereof, where this protein is one whose function is necessary in order to remedy a disorder, in particular a metabolic disorder or in order to initiate processes in vivo such as the formation of new blood vessels, tissues, etc. Here, functional variant is understood to mean a fragment which in the cell can undertake the function of the protein whose function in the cell is needed or the lack or defective form whereof is pathogenic. In addition, the mRNA may also have further functional regions and/or 3' or 5' noncoding regions. The 3' and/or 5' noncoding regions can be the regions naturally flanking the protein-encoding sequence or artificial sequences which contribute to the stabilization of the RNA. Those skilled in the art can determine the sequences suitable for this in each case by routine experiments.

In a preferred embodiment, the mRNA contains an m7GpppG cap, an internal ribosome entry site (IRES) and/or a polyA tail at the 3' end in particular in order to improve translation. The mRNA can have further regions promoting translation.

In a preferred embodiment the mRNA is an mRNA which contains a combination of modified and unmodified nucleotides. Preferably, it is an mRNA containing a combination of modified and unmodified nucleotides as described in WO2011/012316. The mRNA described therein is reported to show an increased stability and diminished immunogenicity. In a preferred embodiment, in such a modified mRNA 5 to 50% of the cytidine nucleotides and 5 to 50% of the uridine nucleotides are modified. The adenosine- and guanosine-containing nucleotides can be unmodified. The adenosine and guanosine nucleotides can be unmodified or partially modified, and they are preferably present in unmodified form. Preferably 10 to 35% of the cytidine and uridine nucleotides are modified and particularly preferably the content of the modified cytidine nucleotides lies in a range from 7.5 to 25% and the content of the modified uridine nucleotides in a range from 7.5 to 25%. It has been found that in fact a relatively low content, e.g. only 10% each, of modified cytidine and uridine nucleotides can achieve the desired properties. It is particularly preferred that the modified cytidine nucleotides are 5-methylcytidine residues and the modified uridine nucleotides are 2-thiouridine residues. Most preferably, the content of modified cytidine nucleotides and the content of the modified uridine nucleotides is 25%, respectively.

In another preferred embodiment, the mRNA may be combined with target binding sites, targeting sequences and/or with micro-RNA binding sites, in order to allow activity of the desired mRNA only in the relevant cells. In a further preferred embodiment, the RNA can be combined with micro-RNAs or shRNAs downstream of the 3' polyA tail.

Furthermore, the term "nucleic acid(s)" may refer to DNA or RNA or hybrids thereof or any modification thereof that is known in the state of the art (see, e.g., U.S. Pat. No. 8,278,036, WO 2013/052523, WO 2011/012316, U.S. Pat. Nos. 5,525,711, 4,711,955, 5,792,608 or EP 302175, (Lorenz et al. 2004, Bioorg Med Chem Lett, 14, 4975-4977; Soutschek et al. 2004, Nature, 432, 173-178) for examples of modifications). Such nucleic acid molecule(s) are single- or double-stranded, linear or circular, natural or synthetic, and without any size limitation. For instance, the nucleic acid molecule(s) may be genomic DNA, cDNA, mRNA, antisense RNA, ribozyme, or small interfering RNAs (siRNAs), micro RNAs, antagomirs, or short hairpin RNAs (shRNAs), tRNAs or long double-stranded RNAs or a DNA construct encoding such RNAs or chimeraplasts (Colestrauss et al. 1996, Science, 273, 1386-1389), or aptamers, clustered regularly interspaced short palindromic repeats ("CRISPR" for RNA-guided site-specific DNA cleavage) (Cong et al. 2013, Science, 339, 819-823), or RNA and DNA. Said nucleic acid molecule(s) may be in the form of plasmids, cosmids, artificial chromosomes, viral DNA or RNA, bacteriophage DNA, coding and non-coding single-stranded (mRNA) or double-stranded RNA and oligonucleotide(s), wherein any of the state of the art modifications in the sugar backbone and/or in the bases as described above and 3'- or 5'-modifications are included. In a particularly preferred embodiment the nucleic acid is RNA, more preferably mRNA or siRNA.

The nucleic acid(s) may contain a nucleotide sequence encoding a polypeptide that is to be expressed in a target cell. Methods which are well known to those skilled in the art can be used to construct recombinant nucleic acid molecules; see, for example, the techniques described in Sambrook et al., Molecular Cloning A Laboratory Manual, Cold Spring Harbor Laboratory (2001) N.Y. and Ausubel et al., Current Protocols in Molecular Biology, Green Publishing Associates and Wiley Interscience, N.Y. (1989).

In a preferred embodiment, said nucleic acid is a therapeutically or pharmaceutically active nucleic acid including all nucleic acid types and modifications listed above and those known to the one skilled in the art which may have a therapeutic or preventive effect. In general, therapeutic or preventive effects can be achieved by the interaction of the nucleic acid with cellular molecules and organelles. Such interaction alone may for example activate the innate immune system, as is the case for certain CpG oligonucleotides and sequences designed to specifically interact with toll-like and other extra- or intracellular receptors. Furthermore, the uptake or introduction of nucleic acids in cells can be intended to lead to the expression of nucleotide sequences such as genes comprised in the nucleic acid, can be intended for the downregulation, silencing or knockdown of endogenous gene expression as a consequence of the intracellular presence of an introduced exogenous nucleic acid, or can be intended for the modification of endogenous nucleic acid sequences such as repair, excision, insertion or exchange of selected bases or of whole stretches of endogenous nucleic acid sequences, or can be intended for interference with virtually any cellular process as a consequence of the intracellular presence and interaction of an introduced exogenous nucleic acid. Overexpression of introduced exogenous nucleic acids may be intended to compensate or complement endogenous gene expression, in particular in cases where an endogenous gene is defective or silent, leading to no, insufficient or a defective or a dysfunctional product of gene expression such as is the case with many metabolic and hereditary diseases like cystic fibrosis, hemophilia or muscular dystrophy to name a few. Overexpression of introduced exogenous nucleic acids may also be intended to have the product of the expression interact or interfere with any endogenous cellular process such as the regulation of gene expression, signal transduction and other cellular processes. The overexpression of introduced exogenous nucleic acids may also be intended to give rise to an immune response in context of the organism in which a transfected or transduced cell resides or is made to reside. Examples are the genetic modification of antigen-presenting cells such as dendritic cells in order to have them present an antigen for vaccination purposes. Other examples are the overexpression of cytokines in tumors in order to elicit a tumor-specific immune response. Furthermore, the overexpression of introduced exogenous nucleic acids may also be intended to generate in vivo or ex vivo transiently genetically modified cells for cellular therapies such as modified T-cells or precursor or stem or other cells for regenerative medicine.

Downregulation, silencing or knockdown of endogenous gene expression for therapeutic purposes can for example be achieved by RNA interference (RNAi), with ribozymes, antisense oligonucleotides, tRNAs, long double-stranded RNA where such downregulation can be sequence-specific or unspecific and can also lead to cell death as is the case when long double-stranded RNAs are introduced into cells. Downregulation, silencing or knockdown of endogenous or pre-existing gene expression can be useful in the treatment of acquired, hereditary or spontaneously incurring diseases including viral infections and cancer. It can also be envisaged that the introduction of nucleic acids into cells can be practiced as a preventive measure in order to prevent, for example, viral infection or neoplasias. Downregulation, silencing or knockdown of endogenous gene expression can be exerted on the transcriptional level and on the translational level. Multiple mechanisms are known to the one skilled in the art and include for example epigenetic modifications, changes in chromatin structure, selective binding of transcription factors by the introduced nucleic acid, hybridization of the introduced nucleic acid to complementary sequences in genomic DNA, mRNA or other RNA species by base pairing including unconventional base pairing mechanisms such as triple helix formation. Similarly, gene repair, base or sequence changes can be achieved at the genomic level and at the mRNA level including exon skipping. Base or sequence changes can for example be achieved by RNA-guided site-specific DNA cleavage, by cut and paste mechanisms exploiting trans-splicing, trans-splicing ribozymes, chimeraplasts, spliceosome-mediated RNA trans-splicing, or by exploiting group II or retargeted introns, or by exploiting insertional mutagenesis mediated by viruses or exploiting targeted genomic insertion using prokaryotic, eukaryotic or viral integrase systems. As nucleic acids are the carriers of the building plans of living systems and as they participate in many cellular processes in a direct and indirect manner, in theory any cellular process can be influenced by the introduction of nucleic acids into cells from outside. Notably, this introduction can be carried out directly in vivo and ex vivo in cell or organ culture followed by transplantation of thus modified organs or cells into a recipient. Complexes of the present invention with nucleic acids as active agents may be useful for all purposes described above.

Composition

As disclosed above, the composition in accordance with the invention comprises the nucleic acid and the component comprising an oligo(alkylene amine) which component is selected from:

a) an oligomer or polymer comprising a plurality of groups of formula (II) as a side chain and/or as a terminal group:

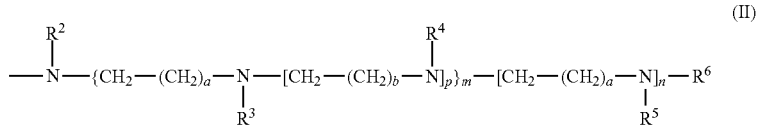

(II)

wherein the variables a, b, p, m, n and $R^2$ to $R^6$ are defined as above, including preferred embodiments, and in particular the preferred groups of formulae (IIa)-(IId); and wherein one or more of the nitrogen atoms indicated in formula (II) may be protonated to provide a cationic group of formula (II);

b) an oligomer or polymer comprising a plurality of groups of formula (III) as repeating units:

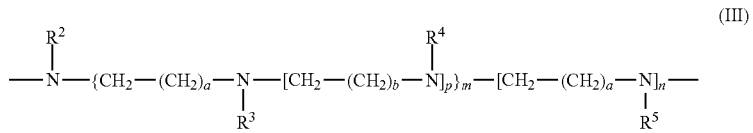

(III)

wherein the variables a, b, p, m, n and $R^2$ to $R^5$ are defined as above, including preferred embodiments, and in particular the preferred groups of formulae (IIIa)-(IIId); and wherein one or more of the nitrogen atoms indicated in formula (III) may be protonated to provide a cationic group of formula (III); or c) a lipidoid having the structure of formula (IV):

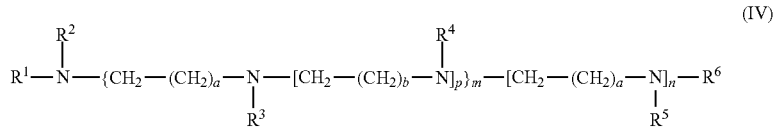

wherein the variables a, b, p, m, n and R1 to R6 are defined as above, including preferred embodiments, and in particular the preferred structure of formulae (IVa)-(IVc); and wherein one or more of the nitrogen atoms indicated in formula (IV) may be protonated to provide a cationic group of formula (IV).

The invention encompasses also a composition which consists of the RNA, preferably single-stranded RNA such as mRNA, and the component comprising an oligo(alkylene amine) selected from components a) to c) as defined herein, including the preferred embodiments thereof. However, the composition may also comprise further components, e.g. components for lipid formulation and/or components that exert an effector function during RNA, preferably single-stranded RNA such as mRNA, delivery to and into a cell.

It will be understood that the compositions in accordance with the invention generally provide an association of RNA, preferably single-stranded RNA such as mRNA, with an oligomer, polymer or lipidoid and optional further components which are associated in a finite entity, stable enough to maintain association of a significant proportion of said components until reaching a biological target or the surroundings of a biological target during an application, for example during a desired route of RNA, preferably single-stranded RNA such as mRNA, delivery.

Due to the presence of the protonatable amino groups in the oligomers, polymers or lipidoids in accordance with the invention, these oligomers, polymers or lipidoids may comprise cationic charges in the groups of formula (II) or (III) or in the structure of formula (IV), such that the oligomers, polymers or lipidoids form cations, typically oligo- or polycations containing a plurality of cationic moieties, in the presence of protons, e.g. in water or aqueous solutions, or in the presence of a proton donating acid. Thus, preferably, the composition in accordance with the invention contains or consists of a complex of RNA, preferably single-stranded RNA such as mRNA, and a cationic oligomer, polymer or lipidoid in accordance with the invention. It will be understood that a cationic oligomer, polymer or lipidoid and an anionic nucleic acid are generally associated via electrostatic interaction in such a complex. However, depending on the specific structure of the oligomer, polymer or lipidoid and the RNA, preferably single-stranded RNA such as mRNA, other attractive interactions may also participate in stabilizing the complex, including hydrogen bonds and covalent bonds.

In the compositions of the present invention, the oligomer, polymer or lipidoid and RNA, preferably single-stranded RNA such as mRNA, can be contained, e.g., in a ratio weight oligomer, polymer or lipidoid/weight nucleic acid (w/w) of 0.25/1-50/1, preferably of 0.5/1-30/1, more preferably of 1/1-20/1.

More preferably, in cases wherein the composition contains a complex of the RNA, preferably single-stranded RNA such as mRNA, and a cationic oligomer, polymer or lipidoid in accordance with the invention, relative ratios of the oligomer, polymer or lipidoid and the RNA, preferably single-stranded RNA such as mRNA, in the compositions of the invention may be selected considering the degree of mutual charge neutralization. In RNA, preferably single-stranded RNA such as mRNA, delivery with complexes of the RNA, preferably single-stranded RNA such as mRNA, with a cationic oligomer, polymer or lipidoid, in general, amounts of the cationic oligomer, polymer or lipidoid are mixed with a given quantity of RNA, preferably single-stranded RNA such as mRNA, which leads to at least a charge neutralization of the RNA negative charges, preferably to an over-compensation of the RNA's negative charges.

Suitable ratios between cationic oligomer, polymer or lipidoid and RNAs can easily be determined by gel retardation assays, fluorescence quenching methods such as the ethidium bromide displacement/quenching assay, by particle sizing and zeta potential measurements. Useful ratios between oligomer, polymer or lipidoid and RNA are usually characterized by at least partial, preferably complete retardation of the RNA comprised in the complex with the cationic oligomer, polymer or lipidoid when subjected to electrophoresis in an agarose gel, by a high degree of fluorescence quenching of dyes such as ethidium bromide, RiboGreen or YOYO when intercalated in the RNAs or by the formation of (nano)particles upon mixing oligomer, polymer or lipidoid and RNA. For chemically well-defined cations, the calculated N/P ratio is a suitable factor to choose and define the relative ratios of the oligomer, polymer or lipidoid and the RNA. The N/P ratio designates the molar ratio of the protonatable nitrogen atoms in the groups of formula (II) (or preferred embodiments thereof), in the groups of formula (III) (or preferred embodiments thereof) or in the structure of formula (IV) (or preferred embodiments thereof) of the oligomer, polymer or lipidoid of the present invention over the phosphate groups of the RNA in the composition of the present invention. The N/P ratio is an established parameter for the characterization of such complexes of RNAs with cationic vehicles, and it will be understood by the skilled reader that e.g. nitrogen atoms in amide bonds do not count as protonatable nitrogen atoms. In the case of a cationic oligomer or polymer, the N/P ratio can be conveniently calculated e.g. according to the formula $$\frac{N}{P} = \frac{w_p \times n}{M_{wp}} \div \frac{w_{na}}{M_{base}}$$

where $w_p$ is the weight of the oligomer or polymer, n is the number of protonatable aminogroups per repeating unit, $M_{wp}$ is the molecular weight of the repeating unit (including counter ions), $w_{na}$ is the weight of the RNA and $M_{base}$ is the average molecular weight of a nucleotide in the RNA which is 346 in the case of RNA. In binary polycation/RNA complexes for RNA delivery in accordance with the invention, relative amounts of the oligomer, polymer or lipidoid to the RNA should preferably be used which provide an N/P ratio resulting in a positive zeta potential of the final binary composition. For a composition comprising a lipidoid of formula (IV) and an RNA, the N/P ratio can be conveniently calculated taking into account the number of protonatable nitrogen atoms in the lipidoid and the number of moles of the lipidoid used in the composition. In the context of the present invention, for binary compositions of the present invention, N/P ratios from 1 to 100 are preferred, more preferred are N/P ratios from 3 to 60, and most preferred are N/P ratios from 4 to 44.

The composition in accordance with the invention optionally comprises further components for lipid formulation. For example, the composition comprising a lipidoid of formula (IV) or the preferred embodiments thereof, including formulae (IVa) to (IVc) comprises further lipids such as cholesterol, DOPE, DOPC or DSPC which are referred to as helper lipids in the scientific literature and/or PEGylated lipids or any other lipid useful for preparing lipoplexes. Preferred helper lipids in the context of the present invention are cholesterol, DOPE, DOPC and DSPC. In certain embodiments the composition containing a lipidoid is about 40-60% lipidoid, about 40-60% cholesterol, and about 5-20% PEG-lipid (in percent by weight, based on the total weight of the composition). In certain embodiments, the composition containing a lipidoid is about 50-60% lipidoid, about 40-50% cholesterol, and about 5-10% PEG-lipid. In certain embodiments, the composition containing a lipidoid is about 50-75% lipidoid, about 20-40% cholesterol, and about 1-10% PEG-lipid. In certain embodiments, the composition containing a lipidoid is about 60-70% lipidoid, about 25-35% cholesterol, and about 5-10% PEG-lipid. The composition may be provided by any means known in the art (e.g as described in Akinc et al, 2007, Nat Biotech, 26, 561-569; Akinc et al, 2009, Mol Ther, 17, 872-9; Love et al, 2010, PNAS, 107, 1864-9; U.S. Pat. No. 8,450,298, WO2006/138380). RNA/lipidoid complexes may form particles that are useful in the delivery of RNA, preferably single-stranded RNA such as mRNAs, into cells. Multiple lipidoid molecules may be associated with an RNA, preferably single-stranded RNA such as mRNA, molecule. For example, a complex may include 1-100 lipidoid molecules, 1-1,000 lipidoid molecules, 10-1,000 lipidoid molecules, or 100-10,000 lipidoid molecules. The complex of (m)RNA and lipidoid may form a particle. The diameter of the particles may range, e.g., from 10-1,200 nm, more preferably the diameter of the particles ranges from 10-500 nm, and most preferably from 20-150 nm.

The composition of the invention optionally comprises components that exert an effector function during RNA, preferably single-stranded RNA such as mRNA, delivery to and into a cell. Such components can be but are not limited to polyanions, lipids as described above, polycations other than the oligomers, polymers or dendrimers of the present including cationic peptides, shielding oligomer or polymers, poloxamers (also known as pluronics), poloxamines, targeting ligands, endosomolytic agents, cell penetrating and signal peptides, magnetic and non-magnetic nanoparticles, RNAse inhibitors, fluorescent dyes, radioisotopes or contrast agents for medical imaging. The term "effector function" encompasses any function that supports achieving an intended biological effect of an RNA, preferably single-stranded RNA such as mRNA, of the composition at or in a biological target or the surrounding of a biological target. For example, compositions for nucleic acid delivery have been formulated to comprise non-coding nucleic acids or non-nucleic acid polyanions as stuffer materials (Kichler et al. 2005, J Gene Med, 7, 1459-1467). Such stuffer materials are suitable for reducing the dose of a nucleic acid having an intended biological effect while maintaining the extent or degree of that effect obtained at a higher nucleic acid dose in the absence of such stuffer material. Non-nucleic acid polyanions have also been used to obtain prolonged in vivo gene expression at reduced toxicity (Uchida et al. 2011, J Control Release, 155, 296-302). The compositions of the present invention can also comprise cationic, anionic or neutral lipids such as is the case in lipopolyplexes (Li and Huang in "Nonviral Vectors for Gene Therapy", Academic Press 1999, Chapter 13, 295-303). Lipopolyplexes may be prepared advantageously from polymers corresponding to formulae (II) and (III) of the present invention with lipidoids corresponding to formula (IV) of the present invention. Furthermore, compositions of the present invention can comprise oligo- or polycations other than the oligo(amino alkylene)-comprising cationic oligomers, polymers or lipidoids of the present invention. Such additional polycations can be useful to achieve a desired degree of compaction of a nucleic acid or in the case of polycationic peptides can have a nuclear localization signal function such as described previously (Ritter et al. 2003, J Mol Med, 81, 708-717). Shielding polymers such as poly(ethylene glycol) (PEG) can as well be comprised in the compositions of the present invention and are used frequently to stabilize polyplexes and lipoplexes against aggregation and/or undesired interactions in a biological environment (opsonization), for example interactions with serum components, blood cells or extracellular matrix. Shielding can also be suitable to reduce the toxicity of nucleic acid-comprising compositions (Finsinger et al. 2000, Gene Ther, 7, 1183-1192). Shielding polymers such as PEG can be covalently coupled directly to polymers or lipidoids of the present invention. The coupling can be achieved in the polymer backbone, preferably, if feasible, to the terminal ends of a polymer backbone or a dendrimer. However, the coupling can also be achieved to the amino groups of formulae (II), (III) and (IV).

Polyvinyl derivatives such as PVP and poloxamers have been found useful to enhance transfection upon intramuscular injection (Mumper et al. 1996, Pharm Res, 13, 701-709, Lemieux et al. 2000, Gene Ther, 7, 986-991) and hence can be useful to be comprised in the compositions of the present invention.

Targeting ligands including antibodies comprised in compositions for nucleic acid delivery are useful for preferential and improved transfection of target cells (Philipp and Wagner in "Gene and Cell Therapy—Therapeutic Mechanisms and Strategy", 3rd Edition, Chapter 15. CRC Press, Taylor & Francis Group LLC, Boca Raton 2009). A targeting ligand can be any compound that confers to compositions of the present invention a target recognition and/or target binding function in a direct or indirect manner. In most general terms, a target is a distinct biological structure to which a targeting ligand can bind specifically via molecular interaction and where such binding will ultimately lead to preferential accumulation of the nucleic acid comprised in the composition in a target tissue and/or at or in a target cell. Similarly as PEG chains, targeting ligands can be coupled to the terminal ends of a polymer backbone or a dendrimer. However, the coupling can also be achieved to the groups of formulae (II), (III) and (IV).

Furthermore, endosomolytic agents such as endosomolytic peptides (Plank et al. 1998, Adv Drug Deliv Rev, 34, 21-35) or any other compound that is suited to enhance the endosomal release of an endocytosed nucleic acid are useful components of compositions of present inventions. Similarly, cell penetrating peptides (in another context also known as protein transduction domains) (Lindgren et al. 2000, Trends Pharmacol Sci, 21, 99-103) can be useful components of the composition of the present invention in order to mediate intracellular delivery of a nucleic acid. The so-called TAT peptide falls within this class and also has nuclear localization function (Rudolph et al. 2003, J Biol Chem, 278, 11411-11418).

Magnetic nanoparticles which may be comprised in compositions of the present invention are useful for physical targeting of delivery by magnetic force and for a drastic enhancement of the efficiency of nucleic acid transfer, a mechanism also known as Magnetofection (EP1297169; Plank et al. 2011, Adv Drug Deliv Rev, 63, 1300-1331). Similarly, a composition of the present invention can also be a non-magnetic or magnetic microbubble used for physical enhancement and targeting of nucleic acid delivery via ultrasound and optionally magnetic field application (Holzbach et al. 2010, J Cell Mol Med, 14, 587-599, Vlaskou et al. 2010, Adv Funct Mater, 20, 3881-3894). Quantum dots (Zintchenko et al. 2009, Mol Ther, 17, 1849-1856), radioactive tracers and contrast agents for medical imaging can be used advantageously for tracking nucleic acid delivery and to determine the biodistribution of compositions for nucleic acid delivery. Summarizing, numerous effectors for nucleic acid delivery have been described and can be useful components in compositions comprising a nucleic acid and an oligomer or polymer or dendrimer according to the invention.

It is well known to those skilled in the art that there is a great degree of flexibility with respect to the amount of substance of each component comprised in the composition according to the present invention. For example, so-called monomolecular binary polyplexes have been described for plasmid DNA where the composition consists of nanoparticles formed upon mixing of the polycation and the plasmid DNA which comprise exactly a single plasmid DNA molecule and as many polycation molecules which are required for charge neutralization or charge overcompensation (positive over negative) (DeRouchey et al. 2006, J Phys Chem B. 110(10):4548-54). For PEI-DNA complexes at N/P ratios which are often used in transfections it was found by fluorescence correlation spectroscopy that they contain on average 3.5 (+/−1) DNA plasmid molecules and 30 PEI molecules while about 86% of the PEI molecules used for preparing the complexes were in a free form (Clamme et al. 2003, Biophys J 84, 1960-1968). In the other extreme, it was found that aggregated complexes of PEI and plasmid DNA, putatively comprising a large number (tens to hundreds) of the component molecules performed better in transfection than small discrete PEI-DNA nanoparticles (Ogris et al. 1998, Gene Ther, 5, 1425-1433; Ogris et al. 2001, AAPS PharmSci, 3, E21). Hence, the composition according to the present invention can be a (nano)particle comprising a few RNA, preferably single-stranded RNA such as mRNA, molecules but may as well be a macroscopic object such as a precipitate or a dry powder comprising enormous numbers of RNA, preferably single-stranded RNA such as mRNA, molecules. Summarizing, the compositions of the current invention are characterized by the input ratios of their components before self-assembly. Typical input w/w ratios of individual components relative to the RNA, preferably single-stranded RNA such as mRNA, component are between 1 and 50. The N/P ratio is a suitable measure of the input ratio for binary polymer/dendrimer or lipidoid compositions when the oligomer or polymer/dendrimer or lipidoid is chemically well defined. If the composition of the present invention comprises further components, an assignment of an N/P ratio may be ambiguous. In this case, suitable input ratios are determined by experiment including but not limited to gel retardation assays, fluorescence quenching assays such as the ethidium bromide displacement/quenching assay, by particle sizing and zeta potential measurements and by functional assays such as transfection assays as described herein. In ternary complexes comprising an additional polyanion or shielding polymers, the net charge ratio (positive over negative) may be smaller than 1 and the zeta potential may be neutral or negative.

The composition of the invention can be produced as described below. After the self-assembly process, the composition of the present invention may be separated from any un-incorporated components and in the same step the suspension medium can be replaced by centrifugation or by ultrafiltration or size exclusion chromatography or dialysis or any related methods. The stoichiometry of the components of the composition of the present invention, purified or un-purified, can be determined by a variety of analytical methods including spectroscopic methods such as UV/VIS spectrometry or fluorescence correlation spectroscopy (DeRouchey et al. 2006, J Phys Chem B. 110(10):4548-54), by orthogonal fluorescence or radioisotope labelling of the individual components, by NMR and IR spectroscopy or chromatographic analysis and quantitation upon disassembly of the composition. Disassembly can be achieved for example by the addition of excess polyanion such as heparin as described herein or chondroitin sulphate or by the addition of sodium dodecylsulphate.

The present invention also relates to a method for producing the composition of the invention. Oligomers, polymers or lipidoids of the present invention can be produced and purified as described herein. The oligomers, polymers or lipidoids can be stored in aqueous solution or as dried powder in which case they are redissolved in aqueous medium, preferably water, before producing the composition. The pH of the solution is adjusted to neutral or slightly acidic (down to pH 4.5) with an acid, preferably with hydrochloric or citric acid, if required. In the case of RNA, preferably single-stranded RNA such as mRNA, being the nucleic acid comprised in the composition it is preferred that the pH is adjusted to about 4.5 to 5.5, preferably to about 4.9 to 5.1, more preferably to about 5.0. Nucleic acids are produced and purified according to the state of the art well known to the one skilled in the art. The nucleic acid is provided as solution in aqueous medium, preferably water. Optionally, either the oligomer, polymer or lipidoid or the nucleic acid or both are chemically linked with effector molecules such as targeting ligands, signal peptides, cell penetrating peptides, endosomolytic substances or shielding polymers. However, depending on the chemical nature of the effector molecules, they may not need to be attached by chemical bond but can rather be incorporated in the composition of the present invention by self-assembly based on non-covalent binding, i.e. electrostatic, hydrophobic or Vander-Waals interaction with any of the other components of the composition. For this purpose, it may be advantageous to adjust the ionic strength, type of counterion, pH or organic solvent content of individual component solutions.

Organic solvents can be used to prepare stock solutions of the lipidoids of formula (IV) and can be required for the co-assembly of further weakly or non-water-soluble components such as lipids or hydrophobic oligomers or polymers. Suitable organic solvents are for example water-miscible solvents such as ethanol and other alcohols, dimethylsulfoxide, dimethylformamide, N-methylpyrrolidone, or glycofurol and other solvents described in WO2013/045455. In one embodiment, lipidoid-comprising compositions of the present invention are prepared from lipidoids and further components such as helper lipids dissolved in any of these solvents, preferably ethanol, and an RNA, preferably single-stranded RNA such as mRNA, dissolved in aqueous medium, preferably buffered to acidic pH. In a first step, the components dissolved in the organic phase are mixed at the desired stoichiometric ratio and diluted to a desired end volume with the organic solvent of choice. An amount of the RNA, preferably single-stranded RNA such as mRNA, corresponding to the desired end ratio with respect to the lipidoid is diluted in the aqueous medium. Preferably, the volume of the aqueous medium is at least equal to the volume of the combined component solutions in organic solvent. Preferably, the volume of the aqueous phase comprising the RNA, preferably single-stranded RNA such as mRNA, exceeds the volume of the combined component solutions in organic solvent, most preferably, the v/v ratio of aqueous and organic phase is 4:1. In the second step, the lipidoid-comprising organic mixture is rapidly injected into the aqueous solution of the RNA, preferably single-stranded RNA such as mRNA, preferably while vortexing. Optionally, the solutions of RNA, preferably single-stranded RNA such as mRNA, and lipidoid-comprising components are heated before or after this step to up to 70° C. If required or desired, the organic solvent can now be removed by evaporation, dialysis, ultrafiltration, diafiltration or size exclusion chromatography while in the same step the dispersion medium can be exchanged to a final desired buffer composition such as PBS. Optionally, the composition can be extruded through membrane filters of desired pore size for sterilization and/or for obtaining a monodisperse formulation.

As an alternative to the mixing procedure described above, the RNA, preferably single-stranded RNA such as mRNA, and lipidoid component can be mixed with an automated device for micro-mixing such as described for example by Hirota et al. (Hirota et al. 1999, Biotechniques, 27, 286-290) or Kasper et al. (Kasper et al. 2011, Eur J Pharm Biopharm, 77, 182-185) or by microfluidic focusing such as reviewed by Xuan et al. (Xuan et al. 2010, Microfluidics and Nanofluidics, 9, 1-16).

An alternative for obtaining lipidoid-comprising compositions according to the present invention is via liposomes or micelles as an intermediate. Lipoplexes are often prepared from commercially available transfection reagents that are micelles or liposomes in aqueous suspension. The lipidoids of the present invention may be used to prepare micelles or liposomes. Many techniques for preparing micelles and liposomes are known in the art, and any method may be used with the inventive lipidoids to make micelles and liposomes. In addition, any agent including RNA, preferably single-stranded RNA such as mRNAs, small molecules, proteins, peptides, metals, organometallic compounds, etc. may be included in a micelle or liposome. In certain embodiments, liposomes (lipid or lipidoid vesicles) are formed through spontaneous assembly. In other embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these liposomes have formed, reducing the size of the particle can be modified through input of sonic energy (sonication) or mechanical energy (extrusion) (Szoka et al, 1980, Ann Rev Biophys Bioeng, 9, 467-508). The preparation of liposomes involves preparing the lipidoids for hydration, hydrating the lipidoids with agitation, and sizing the vesicles to achieve a homogenous distribution of liposomes. For this purpose, the lipidic components to be comprised in a composition of the present invention are dissolved as stock solutions in organic solvent such as chloroform. The components are then mixed at the desired stoichiometric ratio and the organic solvent is removed by rotary evaporation in a suitable vessel such as a round bottom flask, leading to a thin lipid film on the vessel wall. Preferably, the film is dried in high vacuum. Hydration of the lipidoid film/cake is accomplished by adding an aqueous medium to the container of dry lipidoid and agitating the mixture. Disruption of LMV suspensions using sonic energy typically produces small unilamellar vesicles (SUV) with diameters in the range of 15-50 nm. Lipid extrusion is a technique in which a lipid suspension is forced through a polycarbonate filter with a defined pore size to yield particles having a diameter near the pore size of the filter used. Extrusion through filters with 100 nm pores typically yields large, unilamellar vesicles (LUV) with a mean diameter of 120-140 nm. Certain lipidoids can spontaneously self-assemble around certain molecules, such as nucleic acids (e.g. DNA and mRNA), to form liposomes. In some embodiments, the application is the delivery of RNA, preferably single-stranded RNA such as mRNAs. Use of these lipidoids allows for simple assembly of liposomes without the need for additional steps or devices such as an extruder.

The composition of the present invention comprising an RNA, preferably a single-stranded RNA such as mRNA, can then be prepared by self-assembly upon mixing the solutions of the components. Self-assembly can be accomplished by hand mixing using pipetting and shaking/vortexing or using an automated device for micro-mixing such as described for example by Hirota et al. (Hirota et al. 1999, Biotechniques, 27, 286-290) or Kasper et al. (Kasper et al. 2011, Eur J Pharm Biopharm, 77, 182-185) or by microfluidic focusing such as reviewed by Xuan et al. (Xuan et al. 2010, Microfluidics and Nanofluidics, 9, 1-16). If the composition of the present invention comprises further components in addition to the RNA, preferably single-stranded RNA such as mRNA, and the oligomer, polymer or lipidoid of the present invention, sequential mixing can be required. In this case, any further component may be added after self-assembly of the oligomer, polymer or lipidoid and the RNA, preferably single-stranded RNA such as mRNA, or it may be added to either of these before mixing. The most suitable sequence of mixing steps will be dependent on the chemical nature of additional components. For example, if the additional component is negatively charged, it may be most suitable to add it to the RNA, preferably single-stranded RNA such as mRNA, component before mixing with the oligomer, polymer or lipidoid or to a pre-formed complex of the oligomer, polymer or lipidoid and the RNA, preferably single-stranded RNA such as mRNA, where the oligomer, polymer or lipidoid is present in excess in terms of the ratio of positive charges over the sum of the negative charges of the (m)RNA and the anionic additional component. Vice-versa, if the additional component is cationic it may be most suitable to add it to the oligomer, polymer or lipidoid before mixing with the (m)RNA. Or it may be used at a stoichiometry to partially neutralize the negative charges of the (m)RNA followed by mixing with the oligomer, polymer or lipidoid solution of the present invention. In the case of (m)RNA comprising complexes for magnetofection, it has been shown that salt-induced colloid aggregation is a suitable means for preparing compositions comprising an (m)RNA, a polycation or a cationic lipid and magnetic particles (EP1297169). In the special case of the (m)RNA component being a cationic oligonucleotide, a polyanion can be used to self-assemble the oligomer, polymer or lipidoid of the present invention with the (m)RNA. In this case, the oligomer, polymer or lipidoid of the present invention is mixed with the cationic oligonucleotide followed by mixing with the polyanion. It is well known to the one skilled in the art that numerous formulation options are available to obtain the composition of the present invention. The concentrations of the individual components are chosen according to the intended use of the composition of the present invention. Relevant parameters are the final concentration of the (m)RNA component and the ratio of components as described above. For (m)RNA delivery in cell culture, final (m)RNA concentrations between 1 and 100 µg/ml are generally preferred. For in vivo applications, useful final (m)RNA concentrations can be up to 5 mg/ml.

The composition of the present invention can be stored in aqueous suspension or can be dried. Hence, in one preferred embodiment, the composition of the present invention is stored in dried form, optionally freeze-dried (lyophilized) form. In a more preferred embodiment, the dried or lyophilized complex or composition also comprises a lyoprotectant. Lyoprotectants are molecules which protect (freeze-) dried material. Such molecules are typically polyhydroxy compounds such as sugars (mono-, di- and polysaccharides), polyalcohols and their derivatives. Trehalose and sucrose are known to be natural protectants for drying processes. Trehalose is produced by a variety of plants, fungi and invertebrate animals that remain in a state of suspended animation during periods of drought (also known as anhydrobiosis). Sugars such as trehalose, lactose, raffinose, sucrose, mannose, sorbitol, mannitol, xylitol, polyethyleneglycol, dextrins, urea, maltodextrins, fructans, maltooligosaccharides, manno-oligosaccharides, cycloinulohexaose, hydroxyethyl starch, dextrans, inulin, polyvinylpyrrolidone or amino acids such as tryptophan, glycin and phenylalanine are particularly suitable lyoprotectants in the scope of the present invention. Most preferably trehalose is used in this context.

Pharmaceutical Aspects

In a further aspect, the present invention relates to the use of the composition of the present invention or of the oligomer, polymer or lipidoid of the present invention for delivering an RNA, preferably a single-stranded RNA such as mRNA, to tissue or into a target cell. The term "delivering an RNA, preferably a single-stranded RNA such as mRNA, to a cell" preferably means transfer of the RNA, preferably single-stranded RNA such as mRNA, into the cell. Said use can be in vivo or in vitro.

The present invention also relates to a method for delivering an RNA, preferably a single-stranded RNA such as mRNA, to a target cell or tissue comprising the step of bringing a composition according to the invention into contact with the target cell or tissue. Such a method can be carried out in vitro or in vivo. The bringing into contact may be achieved by means and methods known to the person skilled in the art. For example, if the method is carried out in vitro, the bringing into contact can be achieved by cultivating the cells in the presence of the composition in the culture medium or by adding the composition to the cells. If the method is carried out in vivo, the bringing into contact with cells or tissues can, e.g., be achieved by the administration of the composition to an individual by routes of administration known to the person skilled in the art, in particular by any route of administration that is usually employed in the field of genetic therapy. Possible ways of formulating the composition and of administering it to an individual are also described further below.

The term "in vivo" refers to any application which is effected to the body of a living organism wherein said organism is preferably multicellular, more preferably a mammal and most preferably a human. The term "in vitro" refers to any application which is effected to parts of the body of a living organism isolated and outside said organism, e.g. cells, tissues and organs, wherein said organism is preferably multicellular, more preferably a mammal and most preferably a human.

The present invention also relates to a pharmaceutical composition comprising the composition or the oligomer, polymer or lipidoid of the invention and optionally a pharmaceutically acceptable carrier and/or diluent. The term "pharmaceutical composition" refers to a pharmaceutically acceptable form of the composition of the present invention which can be administered to a subject.

The term "pharmaceutically acceptable form" means that the composition is formulated as a pharmaceutical composition, wherein said pharmaceutical composition may further comprise a pharmaceutically acceptable carrier and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. The dosage regimen will be determined by the attending physician and clinical factors. As is well known in the medical arts, dosages for any one subject depend upon many factors, including the subject's size, body surface area, age, the particular compound to be administered, sex, time and route of administration, general health, and other drugs being administered concurrently. A typical dose of active substances can be, for example, in the range of 1 ng to several grams. Applied to (m)RNA therapy, the dosage of an (m)RNA for expression or for inhibition of expression should correspond to this range; however, doses below or above this exemplary range are envisioned, especially considering the aforementioned factors. Generally, the regimen as a regular administration of the pharmaceutical composition should be in the range of 0.1 µg to 10 mg units per kilogram of body weight per day. If the regimen is a continuous infusion, it should also be in the range of 1 µg to 10 mg units per kilogram of body weight, respectively. Progress can be monitored by periodic assessment. Dosages will vary but a preferred dosage for intravenous administration of (m)RNAs as constituents of the composition of the present invention is from approximately $10^6$ to 1019 copies of the (m)RNA molecule.

The term "administered" encompasses any method suitable for introducing the composition into the body of a subject. Administration of the suitable compositions may be effected in different ways, e.g., by intravenous, intraarterial, intraperitoneal, subcutaneous, transdermal, intrathecal, intramuscular, topical, intradermal, intranasal, pulmonary by inhalation or intrabronchial or oral or rectal administration. The compositions of the present invention may in particular be administered as a gene-activated matrix such as described by Shea et al. (Shea et al. 1999, Nat Biotechnol, 17, 551-554) and in EP1198489.

In principle, the pharmaceutical compositions of the invention may be administered locally or systemically. Administration will preferably be parenterally, e.g., intravenously, although other ways of administration are within the scope of the invention. Administration directly to the target site, e.g., by catheter to a site in a blood vessel, is also conceivable. Administration can, for example, also occur by direct injection into a target site such as a tumor. Also within the scope of the invention is administration by aerosolization or nebulization or oral administration. Preparations for parenteral administration include sterile aqueous or non-aqueous solutions, suspensions, and emulsions. Examples of non-aqueous solvents are propylene glycol, polyethylene glycol, fluorocarbons, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition may comprise further agents such as interleukins or interferons depending on the intended use of the pharmaceutical composition.

In another embodiment the present invention relates to a method of treatment comprising administering the pharmaceutical composition of the present invention to a patient in order to have the RNA, preferably single-stranded RNA such as mRNA, contained in said composition cause a preventive or therapeutic effect. Notably, the term "patient" comprises animals and humans.

By administering the pharmaceutical composition of the present invention, diseases can be treated or prevented. The term "disease" refers to any conceivable pathological condition that can be treated, prevented or vaccined against by employing an embodiment of the present invention. In a preferred embodiment of said method, said diseases may be inherited, acquired, infectious or non-infectious, age-related, cardiovascular, metabolic, intestinal, neoplastic (in particular cancer) or genetic. A disease can be based, for example, on irregularities of physiological processes, molecular processes, biochemical reactions within an organism that in turn can be based, for instance, on the genetic equipment of an organism, on behavioural, social or environmental factors such as the exposure to chemicals or radiation. In a particularly preferred embodiment, the pharmaceutical composition of the present invention is used for treatments as disclosed in the patent application WO2010EP04681.

In line with the above-described method of treatment, the present invention refers in another embodiment to the use of the composition of the present invention for the preparation of a pharmaceutical composition for the treatment of a disease that can be treated by providing said RNA, preferably single-stranded RNA such as mRNA, contained in said composition to a tissue or organ within the body of a patient affected by a disease.

For further illustration, preferred aspects of the invention are summarized in the following items, which form part of the preceding general disclosure and the preferred embodiments disclosed therein applies as well.

1. An oligomer or polymer comprising a plurality of groups of formula (II) as a side chain and/or as a terminal group:

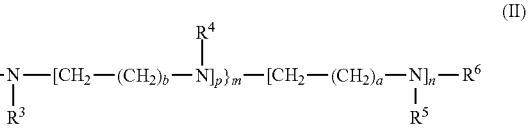

wherein the variables a, b, p, m, n and $R^2$ to $R^6$ are defined as follows, independently for each group of formula (II) in a plurality of such groups:

a is 1 and b is an integer of 2 to 4; or a is an integer of 2 to 4 and b is 1, p is 1 or 2, m is 1 or 2; n is 0 or 1 and m+n is ≥2; and $R^2$ to $R^5$ are, independently of each other, selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C18 alkyl or C3-C18 alkenyl having one C—C double bond; a protecting group for an amino group; and a poly(ethylene glycol) chain;

$R^6$ is selected from hydrogen; a group —$CH_2$—CH(OH)—$R^7$, —CH($R^7$)—CH—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C18 alkyl or C3-C18 alkenyl having one C—C double bond; a protecting group for an amino group; —C(NH)—$NH_2$; a poly(ethylene glycol) chain; and a receptor ligand, and wherein one or more of the nitrogen atoms indicated in formula (II) may be protonated to provide a cationic group of formula (II).

2. The oligomer or polymer of item 1, wherein, in formula (II), p is 1.
3. The oligomer or polymer of item 1 or 2, wherein, in formula (II), n is 1.
4. The oligomer or polymer of item 1 or 2, wherein, in formula (II), m is 1 and n is 1.
5. The oligomer or polymer of any one of items 1 to 4, wherein, in formula (II), a is 1 and b is 2 or a is 2 and b is 1.
6. The oligomer or polymer of any one of items 1 to 5, wherein, in formula (II), $R^2$ to $R^5$ are hydrogen.
7. The oligomer or polymer of any one of items 1 to 6, wherein, in formula (II), $R^6$ is hydrogen.
8. The oligomer or polymer of any one of items 1 to 5, which is a polymer.

9. The polymer of item 8, wherein the polymer backbone carrying a plurality of groups of formula (II) as a side chain and/or as a terminal group is selected from a poly(amino acid) comprising a plurality of glutamic or aspartic acid units, such as poly(glutamic acid) and poly(aspartic acid), a protein, a polyalkyne, a polyamine, polyacrylic acid, polymethacrylic acid, polymaleic acid, polysulfonate, polystyrene sulfonate, polyphosphate, pentosan polysulfate, poly(vinyl phosphoric acid), poly(butadiene-co-maleic acid), poly(ethyl acrylate-co-acrylic acid), poly(ethylene-co-acrylic acid), poly(ethylene-co-maleic anhydride), poly(methyl methacrylate-co-methacrylic acid), poly(methyl methacrylate-co-methacrylic acid), poly(styrenesulfonic acid-co-maleic acid), poly(vinyl chloride-co-vinyl acetate-co-maleic acid), a carbohydrate such as heparin, heparan sulphate, poly(glucuronic acid), poly(galacturonic acid), hyaluronic acid, poly(uronic acids) in general, or a carboxy-terminated dendrimer.

10. The polymer of item 9, which is selected from a poly(amino acid) comprising a plurality of glutamic or aspartic acid units, polyacrylic acid and polymethacrylic acid.

11. An oligomer or polymer comprising a plurality of groups of formula (III) as repeating units:

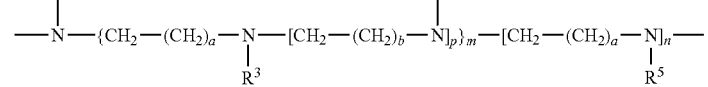

(III)

wherein the variables a, b, p, m, n and $R^2$ to $R^5$ are defined as follows, independently for each group of formula (III) in a plurality of such groups:
a is 1 and b is an integer of 2 to 4; or a is an integer of 2 to 4 and b is 1,
p is 1 or 2,
m is 1 or 2; n is 0 or 1 and m+n is ≥2; and $R^2$ to $R^5$ are, independently of each other, selected from hydrogen; a group —$CH_2$—CH(OH)—$R^7$, —CH($R^7$)—$CH_2$—OH, —$CH_2$—$CH_2$—(C=O)—O—$R^7$ or —$CH_2$—$CH_2$—(C=O)—NH—$R^7$ or —$CH_2$—$R^7$ wherein $R^7$ is selected from C3-C18 alkyl or C3-C18 alkenyl having one C—C double bond; a protecting group for an amino group; —C(NH)—$NH_2$; and a poly(ethylene glycol) chain;
and wherein one or more of the nitrogen atoms indicated in formula (III) may be protonated to provide a cationic group of formula (III).

12. The oligomer or polymer of item 11, wherein, in formula (III), p is 1.

13. The oligomer or polymer of item 11 or 12, wherein, in formula (III), n is 1.

14. The oligomer or polymer of item 11 or 12, wherein, in formula (III), m is 1 and n is 1.

15. The oligomer or polymer of any one of items 11 to 14, wherein, in formula (III), a is 1 and b is 2 or a is 2 and b is 1.

16. The oligomer or polymer of any one of items 11 to 15, wherein, in formula (III), $R^2$ to $R^5$ are hydrogen.

17. The oligomer or polymer of any one of items 11 to 16, which is a polymer.

18. The polymer of item 17, which is a dendrimer.

19. A lipidoid having the structure of formula (IV):

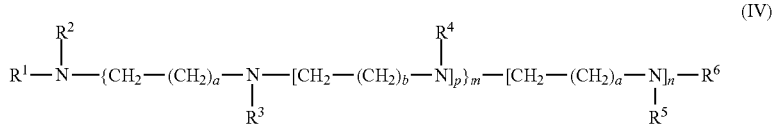

(IV)

wherein the variables a, b, p, m, n and $R^1$ to $R^6$ are defined as follows:
a is 1 and b is an integer of 2 to 4; or a is an integer of 2 to 4 and b is 1,
p is 1 or 2,
m is 1 or 2; n is 0 or 1 and m+n is ≥2; and
$R^1$ to $R^6$ are independently of each other selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C16 alkyl or C3-C6 alkenyl having one C—C double bond; a protecting group for an amino group; —C(NH)—$NH_2$; a poly(ethylene glycol) chain; and a receptor ligand; provided that at least two residues among $R^1$ to $R^6$ are a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C18 alkyl or C3-C18 alkenyl having one C—C double bond;
and wherein one or more of the nitrogen atoms indicated in formula (IV) may be protonated to provide a cationic lipidoid of formula (IV).

20. The lipidoid of item 19, wherein, in formula (IV), p is 1.

21. The lipidoid of item 19 or 20, wherein, in formula (IV), n is 1.

22. The lipidoid of item 19 or 20, wherein, in formula (IV), m is 1 and n is 1.

23. The lipidoid of any one of items 19 to 22, wherein, in formula (IV), a is 1 and b is 2 or a is 2 and b is 1.

24. The lipidoid of any one of items 19 to 22, wherein, in formula (IV), $R^1$ to $R^6$ are independently of each other selected from hydrogen and a group —$CH_2$—CH(OH)—$R^7$, or —CH($R^7$)—$CH_2$—OH, wherein $R^7$ is selected from C8-C16 alkyl or C8-C16 alkenyl having one C—C double bond; provided that at least two residues among $R^1$ to $R^6$ are a group —$CH_2$—CH(OH)—$R^7$, or —CH($R^7$)—$CH_2$—OH, wherein $R^7$ is selected from C8-C16 alkyl or C8-C16 alkenyl having one C—C double bond.
25. A composition comprising an mRNA and an oligomer or polymer of any one of items 1 to 18.
26. The composition of item 25, wherein the oligomer or polymer is a cationic oligomer or polymer.
27. The composition of item 25, comprising a complex of the mRNA and the cationic oligomer or polymer.
28. A composition comprising an mRNA and a lipidoid of any one of items 19 to 24.
29. The composition of item 28, wherein the lipidoid is a cationic lipidoid.
30. The composition of item 29, comprising a complex of the mRNA and the cationic lipidoid.
31. The composition of any of items 25 to 30, which is in lyophilized form.
32. The composition of item 31, which further comprises a lyoprotectant.
33. The composition of item 32, wherein the lyoprotectant is trehalose.
34. A pharmaceutical composition comprising a composition of any one of items 25 to 33.
35. Use of a composition of any one of items 25 to 33 for delivering an mRNA into a cell.
36. Use of an oligomer or polymer of any one of items 1 to 18 or a lipidoid of any of claims 19 to 24 for delivering an mRNA into a cell.
37. A method for delivering an mRNA to a target cell or tissue comprising the step of bringing a composition of any one of items 25 to 33 into contact with the target cell or tissue.

DESCRIPTION OF THE FIGURES

FIG. 1: Effect of type of oligo(alkylene amine) side chain modification of poly(acrylic acid) on transfection efficiency of different cell types with mRNA. Polyplexes were formed using poly(acrylic acid) (MW: 8,000 Da) with side chain modifications (2-3-2) and (3-2-3) or the control groups (3-3-3), (2-2-2), (2-2) or (3-4-3) and mRNA coding for firefly luciferase at N/P ratios between 4 and 44 on indicated cell types. After 24 h cells transfected with different amounts of RNA (500, 250, 125 or 62.5 ng) were lysed and analyzed for luciferase activity.

FIG. 17: Expression of firefly luciferase in murine liver and spleen after intravenous injection of lipidoid formulations. A. in vivo bioluminescence image: Left: mRNA encoding firefly luciferase formulated with lipidoid C14-(2-3-2) (C14-(2-3-2):DOPE:Cholesterol:DSPE-PEG2k; 8:6:5: 1) in PBS for injection; Middle: mRNA encoding firefly luciferase formulated with lipidoid C16-(2-3-2) (C16-(2-3-2):DOPE:Cholesterol:DSPE-PEG2k; 8:6:5:1) in PBS for injection; Right: mRNA encoding firefly luciferase formulated with lipidoid C12-(2-3-2) (C12-(2-3-2):DOPE:Cholesterol:DSPE-PEG2k; 8:6:5:1) in PBS for injection. B. Quantification of in vivo bioluminescence signal. Expression levels decrease with increasing alkyl chain length from C12-C16.

FIG. 26: Comparison of C12 modified oligo(alkyl amine)s (2-3-2), (3-3-3) and (2-2-2) on transfection efficiency in vivo.

FIG. 29: mRNA expression in ex vivo samples after transfection with C12-(2-3-2) containing lipidoid formulations. A: pig muscle, all samples treated; B: pig fat tissue, all samples treated; C: sheep artery; D: sheep muscle, upper sample: treated, lower sample: non-treated; E: sheep lung, upper sample: treated, lower sample: non-treated FIG. 30: Western blot analysis of cell lysates on ACE-2 protein. Left lanes: Lysate of ACE-2 mRNA treated cells; Right lanes: Lysate of cells treated with lipidoid formulations without mRNA (empty). Upper row: Staining of ACE-2; Lower row: GAPDH, loading control.

FIG. 31 Expression of murine erythropoietin in mice. Blood samples were analyzed for mEPO 6 h after intravenous administration of a C12-(2-3-2) formulation containing mEPO mRNA. Three different RNA doses (20 µg, 10 µg or 5 µg) and a control group (PBS) were analyzed.

PRODUCTION EXAMPLE I

Figure 2:
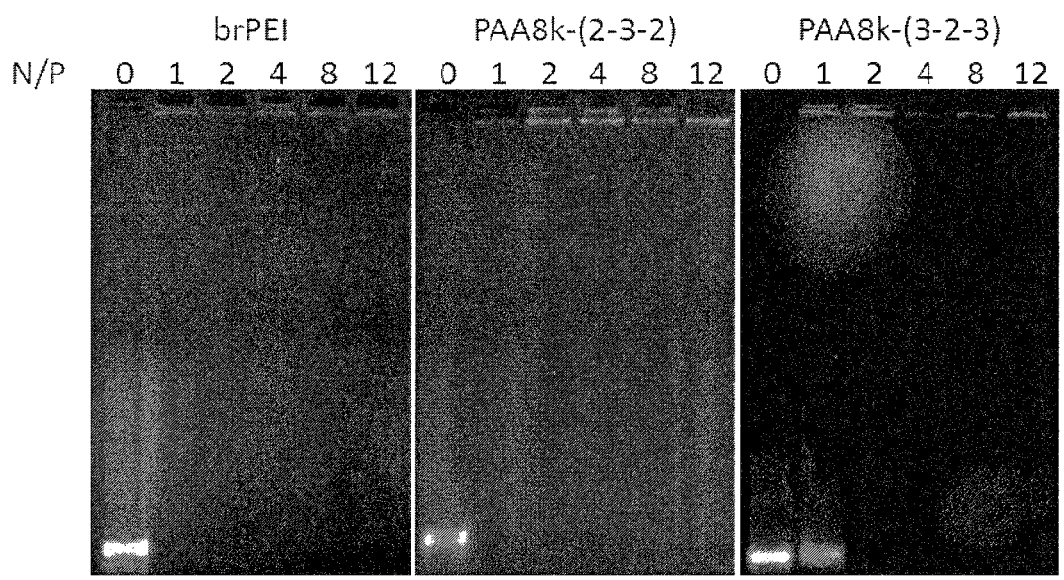
FIG. 2: Gel migration assay for the determination of the complex formation ability of (2-3-2) and (3-2-3) modified PAA8k. Polyplexes were formed as described at indicated N/P ratios. The interaction of polymer and mRNA was analyzed via migration in an agarose gel. The better the interaction the lower the needed amount of polymer for a completely hampered migration of mRNA.

Synthesis of N,N'-Bis(2-aminoethyl)-1,3-propanediamine Modified Poly(Acrylic Acid), MW 8,000 Da, PAA8k-(2-3-2)

10 mg poly(acrylic acid) sodium salt (MW: 8,000 Da, Sigma Aldrich) was diluted in 2 mL reaction buffer containing 50 mM MES, pH 6.0. 1.69 g N,N'-Bis(2-aminoethyl)-1,3-propanediamine (100 eq./carboxy group, Sigma Aldrich) was diluted in 2 mL of the same buffer. As the oligo(alkylene amine) was purchased as free base, the pH was readjusted to pH 6.0 by dropwise addition of 32% HCl. The poly(acrylic acid) and the oligo(alkylene amine) solution were mixed. To start the reaction a 10-fold molar excess of 1-Ethyl-3-(3-dimethylaminopropyl)carbodiimide (EDC, Sigma Aldrich, diluted in 2 mL reaction buffer) per carboxyl group was added. The final volume was adjusted to 10 mL. The mixture was incubated for 3 h at RT on an overhead shaker. The product was purified by dialysis. For this purpose the reaction mixture was filled into a slide-a-lyzer dialysis cassette (3-12 mL, MWCO: 3,500 Da, Thermo Fisher) and dialyzed against water for 72 h. The water was exchanged twice per day. After dialysis the purified polymer was lyophilized. Under same conditions the polymers listed in the following Table 1 were synthesized and tested:

TABLE 1

List of synthesized oligo(alkylene amine) modified polymers.

| Polymeric backbone | | Oligo(alkylene amine) | | | |
| --- | --- | --- | --- | --- | --- |
| Name | Manufacturer/Product nr. | Name | Manufacturer/Product nr. | Resulting polymer | Example |
| poly(acrylic acid) sodium salt, 8,000 Da | Sigma aldrich, 416029 | N,N'-Bis(2-aminoethyl)-1,3-propanediamine | Sigma aldrich, 333131 | PAA8k-(2-3-2) | 1, 2, 3, 4, 8, 9 |
| poly(acrylic acid) sodium salt, 8,000 Da | Sigma aldrich, 416030 | 1,2-Bis(3-aminopropyl-amino)ethane | Sigma aldrich, 23939-9 | PAA8k-(3-2-3) | 1, 2, 4, 8 |
| poly(acrylic acid) sodium salt, 8,000 Da | Sigma aldrich, 416031 | N,N'-Bis(2-aminopropyl)-1,3-propanediamine | Sigma aldrich, 404810 | PAA8k-(3-3-3) | 1, 4 |
| poly(acrylic acid) sodium salt, 8,000 Da | Sigma aldrich, 416032 | Triethylenetetramine | Sigma aldrich, 132098 | PAA8k-(2-2-2) | 1, 4 |
| poly(acrylic acid) sodium salt, 8,000 Da | Sigma aldrich, 416034 | Diethylenetriamine | Sigma aldrich, D93856 | PAA8k-(2-2) | 1 |
| poly(acrylic acid) sodium salt, 8,000 Da | Sigma aldrich, 416035 | Spermine | Sigma aldrich, 85590 | PAA8k-(3-4-3) | 1, 4 |
| poly(glutamic acid) sodium salt, 3,000-12,000 Da | Sigma aldrich, P4636 | N,N'-Bis(2-aminoethyl)-1,3-propanediamine | Sigma aldrich, 333131 | Glu9.8k-(2-3-2) | 3 |
| poly(methacrylic acid) sodium salt, 9,500 Da | Sigma aldrich, 434507 | N,N'-Bis(2-aminoethyl)-1,3-propanediamine | Sigma aldrich, 333131 | PMA9.5k-(2-3-2) | 3 |
| poly(glutamic acid) sodium salt, 50,000-100,000 Da | Sigma aldrich, P4886 | N,N'-Bis(2-aminoethyl)-1,3-propanediamine | Sigma aldrich, 333132 | Glu64k-(2-3-2) | 3 |
| poly(D-Glu, D-LyS), 20,000-50,000 DA | Sigma aldrich, P7658 | N,N'-Bis(2-aminoethyl)-1,3-propanediamine | Sigma aldrich, 333133 | GluLys-(2-3-2) | 3 |
| poly(acrylic acid) sodium salt, 1,200 Da | Sigma aldrich, 416010 | N,N'-Bis(2-aminoethyl)-1,3-propanediamine | Sigma aldrich, 333134 | PAA1.2k-(2-3-2) | 3 |
| poly(acrylic acid) sodium salt, 20,000 Da | Polysciences Inc, 18747 | N,N'-Bis(2-aminoethyl)-1,3-propanediamine | Sigma aldrich, 333135 | PAA20k-(2-3-2) | 3, 4, 5, 6, 7 |
| poly(acrylic acid) sodium salt, 35,000 Da | Polysciences Inc, 18748 | N,N'-Bis(2-aminoethyl)-1,3-propanediamine | Sigma aldrich, 333336 | PAA35k-(2-3-2) | 3 |
| poly(acrylic acid) sodium salt, 70,000 Da | Polysciences Inc, 18749 | N,N'-Bis(2-aminoethyl)-1,3-propanediamine | Sigma aldrich, 333137 | PAA70k-(2-3-2) | 3, 4 |
| poly(acrylic acid) sodium salt, 240,000 Da | Sigma aldrich, 192058 | N,N'-Bis(2-aminoethyl)-1,3-propanediamine | Sigma aldrich, 333138 | PAA240k-(2-3-2) | 3 |
| poly(acrylic acid) sodium salt, 8,000 Da | Sigma aldrich, 416031 | N,N'-Bis(2-aminoethyl)-1,3-propanediamine | Santai Labs, ADH 2970 | PAA8k-(2-4-2) | 14 |

PRODUCTION EXAMPLE II

Synthesis of an Oligo(Alkylene Amine) Building Block for the Generation of Brush Like Polymers by Solid Phase Supported Peptide Synthesis:

I. Synthesis of Tri(Boc) Protected N,N'-Bis(2-aminoethyl)-1,3-propanediamine (EPE(Boc)$_3$)

5 g N,N'-Bis(2-aminoethyl)-1,3-propanediamine (31.2 mmol) is solubilized in 100 mL dichloromethane (DCM) and cooled to 0° C. 4.43 g ethyl trifluoroacetate (31.2 mmol, 1 eq./molecule) is diluted in 100 mL DCM and added drop wise to the stirred solution over a period of 4 h. After addition the solution is stirred at RT overnight. The next day 19.46 mL triethylamine (14.2 g, 0.1404 mol, 1.5 eq./free amine) is added to the reaction mixture. 30.64 g Di-tert-butyldicarbonate (0.1404 mol, 1.5 eq./amine) is solubilized in 100 mL DCM, added drop wise to the stirred solution and incubated at RT for 24 h under constant stirring. After reaction the organic phase is concentrated to approximately 100 mL and washed 3 times with 5% NaHCO$_3$ and 3 times with water. The organic phase is dried over anhydrous Na$_2$SO$_4$, filtered and the solvent evaporated. The product is diluted in 100 mL methanol and 200 mL 3M NaOH (20 eq./molecule) and stirred overnight at RT. The methanol is evaporated and the aqueous solution washed 3 times with DCM. The organic phase is collected, dried over anhydrous Na$_2$SO$_4$, filtered and evaporated. The resulting molecule (EPE(Boc)$_3$) is analyzed by H$^1$-NMR.

II. Synthesis of Fmoc-Glutamic Acid Modified Bocylated N,N'-Bis(2-aminoethyl)-1,3-propanediamine (Fmoc-Glu(EPE(Boc)$_3$-OH)

3.5 g N-(9-Fluorenylmethoxycarbonyl)-L-glutamic-acid (Fmoc-Glu-OH, 9.47 mmol) is mixed with 100 mL acetic anhydride, heated to 100° C. in an oil bath under reflux and constant stirring until the solution becomes clear. The solution is cooled down in ice and the solvents removed via vacuum evaporation at 60° C. The product is solubilized in 100 mL tetrahydrofuran. 5.24 g EPE(Boc)$_3$ (11.37 mmol, 1.2 eq./molecule) is diluted in 100 mL tetrahydrofuran, mixed with 3.3 mL N,N-Diisopropylethylamine (18.94 mmol, 2 eq./molecule) and added to the glutamic acid containing solution. The reaction mixture is stirred for 2 h at RT. After concentration of the solution by evaporation, it is diluted in DCM and washed 3 times with trisodium-citrate buffer (0.1M, pH 5.5). After drying the organic phase over anhydrous Na$_2$SO$_4$ the sample is purified by dry-column flash chromatography on a silica column using a step wise gradient from heptane/ethyl acetate (50/50 to 0/100) and ethyl acetate/methanol (100/0 to 80/20). Fractions containing a UV signal on silica TLC are pooled, the solvent evaporated and the product analyzed by H$^1$-NMR.

PRODUCTION EXAMPLE III

Synthesis of an Oligo(Alkylene Amine) Building Block for the Generation of Linear and Branched Polymers by Solid Phase Supported Peptide Synthesis:

I. Synthesis of Di(Boc) Protected N,N'-Bis(2-aminoethyl)-1,3-propanediamine (EPE(Boc)$_2$)

5 g N,N'Bis(2-aminoethyl)-1,3-propanediamine (31.2 mmol) is solubilized in 100 mL dichloromethane (DCM) and cooled to 0° C. 8.86 g ethyl trifluoroacetate (62.4 mmol, 2 eq./molecule) is diluted in 100 mL DCM and added drop wise to the stirred solution over a period of 4 h. After addition the solution is stirred at RT overnight. The next day 13 mL triethylamine (9.47 g, 0.0936 mol, 1.5 eq./free amine) is added to the reaction mixture. 20.43 g Di-tert-butyldicarbonate (0.0936 mol, 1.5 eq./amine) is solubilized in 100 mL DCM, added drop wise to the stirred solution and incubated at RT for 24 h under constant stirring. After reaction the organic phase is concentrated to approximately 100 mL and washed 3 times with 5% NaHCO$_3$ and 3 times with water. The organic phase is dried over anhydrous Na$_2$SO$_4$, filtered and the solvent evaporated. The product is diluted in 100 mL methanol and 200 mL 3M NaOH (20 eq./molecule) and stirred overnight at RT. The methanol is evaporated and the aqueous solution washed 3 times with DCM. The organic phase is collected, dried over anhydrous Na$_2$SO$_4$, filtered and evaporated. The resulting molecule (EPE(Boc)$_2$) is analyzed by H$^1$-NMR.

II. Synthesis of Succinylated, fmoc-Protected, Bocylated N,N'Bis(2-aminoethyl)-1,3-propanediamine (Fmoc-EPE(Boc)$_2$-OH)

3.0 g (EPE(Boc)$_2$) (8.3 mmol) is resolved in 50 mL tetrahydrofuran and cooled to 0° C. 0.996 g succinic anhydride (10 mmol, 1.2 eq./molecule) is dissolved in 200 mL tetrahydrofuran and added dropwise to the stirred solution. After addition the reaction is stirred for an additional hour at RT. 4.34 mL N,N-Diisopropylethylamine (33.2 mmol, 4 eq./molecule) is added. Then 4.2 g Fmoc N-hydroxysuccinimide ester (12.45 mmol, 1.5 eq./molecule) dissolved in acetonitrile/tetrahydrofuran is added dropwise to the reaction mixture. The solution is stirred overnight. The reaction mixture is concentrated to approximately 100 ml, mixed with 100 ml dichloromethane and is washed 5 times with 0.1 M sodium citrate buffer (pH 5.2). The organic phase is dried, concentrated and the resulting product purified by dry-column flash chromatography on a silica column using a step wise gradient from n-heptane to ethyl acetate (100/0-0/100) and further to ethyl acetate in methanol (100/0-80/20). Fractions containing a UV signal on silica TLC are pooled, the solvent evaporated and the product analyzed by H$^1$-NMR.

PRODUCTION EXAMPLE IV

Synthesis of Lipidoids Based on N,N'-Bis(2-aminoethyl)-1,3-propanediamine 100 mg N,N'-Bis(2-aminoethyl)-1,3-propanediamine (0.623 mmol) was mixed with 575.07 mg 1,2-Epoxydodecane (3.12 mmol, (N-1) eq. where N is 2× amount of primary amine plus 1× amount secondary amine per oligo(alkylene amine)) and mixed for 96 h at 80° C. under constant shaking. After reaction the resulting lipidoid was diluted in 25 mM sodium acetate buffer (ph 5) at a concentration of 100 µg/mL and used for transfection.

Under same conditions the lipidoids, listed in table 2 were synthesized:

TABLE 2

List of synthesized lipidoids

| Oligo(alkyl amine) | Manufacturer/ Product nr. | Lipid | Manufacturer/ Product nr. | Resulting Lipidoid | Example |
|---|---|---|---|---|---|
| N,N'-Bis(2-aminoethyl)-1,3-propanediamine | Sigma aldrich, 333131 | 1,2-Epoxydodecane | Sigma aldrich, 260207 | C12-(2-3-2) | 10, 12 |
| N,N'-Bis(2-aminoethyl)-1,3-propanediamine | Sigma aldrich, 404810 | 1,2-Epoxydodecane | Sigma aldrich, 260207 | C12-(3-3-3) | 10 |
| Triethylenetetramine | Sigma aldrich, 132098 | 1,2-Epoxydodecane | Sigma aldrich, 260207 | C12-(2-2-2) | 10 |
| N,N'-Bis(2-aminoethyl)-1,3-propanediamine | Sigma aldrich, 333131 | 1,2-Epoxytetradecane | Sigma aldrich, 260266 | C14-(2-3-2) | 10, 12 |
| N,N'-Bis(2-aminoethyl)-1,3-propanediamine | Sigma aldrich, 404810 | 1,2-Epoxytetradecane | Sigma aldrich, 260268 | C14-(3-3-3) | 10 |
| Triethylenetetramine | Sigma aldrich, 132098 | 1,2-Epoxytetradecane | Sigma aldrich, 260269 | C14-(2-2-2) | 10 |
| N,N'-Bis(2-aminoethyl)-1,3-propanediamine | Sigma aldrich, 333131 | 1,2-Epoxyhexadecane | Sigma aldrich, 260215 | C16-(2-3-2) | 12 |

PRODUCTION EXAMPLE V

Synthesis of N,N'-Bis(2-aminoethyl)-1,3-propanediamine modified poly(allylamine); (PALAM-(2-3-2))

500 mg poly(allylamine)-solution (Sigma-Aldrich, 20% w/w, molecular weight: 17,000 Da) was diluted in 2 mL reaction buffer containing 50 mM MES, pH 6.0. 10.33 g succinic acid (50 eq. per amine, Sigma-Aldrich) was diluted in 5 mL of the same reaction buffer. The solutions were pooled and the pH readjusted to 6.0. To start the reaction 3.36 g 1-Ethyl-3-(3-dimethylaminopropyl)carbodiimide (EDC, 10 eq. per amine, Sigma Aldrich) diluted in 5 mL reaction buffer was added. The mixture was incubated for 3 h at RT on an overhead shaker. The product was purified by dialysis. For this purpose the reaction mixture was filled into a slide-a-lyzer dialysis cassette (3-12 mL, MWCO: 10,000 Da, Thermo Fisher) and dialyzed against water for 72 h. The water was exchanged twice per day. After dialysis the purified polymer was lyophilized.

5 mg of the lyophilized, succinic acid modified poly(allylamine) was diluted in 2 mL reaction buffer containing 50 mM MES, pH 6.0. 510.38 mg N,N'-Bis(2-aminoethyl)-1,3-propanediamine (100 eq./carboxyl group, Sigma Aldrich) was diluted in 2 mL of the same buffer. As the oligo(alkylene amine) was purchased as free base, the pH was readjusted to pH 6.0 by dropwise addition of 32% HCl. The poly(allylamine) and the oligo(alkylene amine) solution were mixed. To start the reaction a 10-fold molar excess of 1-Ethyl-3-(3-dimethylaminopropyl)carbodiimide (EDC, Sigma Aldrich, diluted in 4 mL reaction buffer) per carboxyl group was added. The final volume was adjusted to 10 mL. The mixture was incubated for 3 h at RT on an overhead shaker. The product was purified by dialysis. For this purpose the reaction mixture was filled into a slide-a-lyzer dialysis cassette (3-12 mL, MWCO: 3,500 Da, Thermo Fisher) and dialyzed against water for 72 h. The water was exchanged twice per day. After dialysis the purified polymer was lyophilized.

Under same conditions the polymers listed in the following Table 3 were synthesized and tested:

TABLE 3

List of synthesized oligo(alkylene amine) modified polymers based on poly(allylamine).

| Polymeric backbone | | Oligo(alkylene amine) | | | |
|---|---|---|---|---|---|
| Name | Manufacturer/ Product nr. | Name | Manufacturer/ Product nr. | Resulting polymer | Example |
| poly(allylamine) 17,000 Da | Sigma aldrich, 479136 | N,N'-Bis(2-aminoethyl)-1,3-propanediamine | EvoBlock, KEMAM-003 | PALAM-(2-3-2) | 26 |
| poly(allylamine) 17,000 Da | Sigma aldrich, 479136 | Triethylenetetramine | Sigma aldrich, 132098 | PALAM-(2-2-2) | 26 |
| poly(allylamine) 17,000 Da | Sigma aldrich, 479138 | N,N'-Bis(2-aminopropyl)-1,3-propanediamine | Sigma aldrich, 404810 | PALAM-(3-3-3) | 26 |

PRODUCTION EXAMPLE VI

Synthesis of N,N'-Bis(2-aminoethyl)-1,3-propanediamine Modified Polypropylenimine (PPI-(2-3-2))

100 mg polypropylenimine hexadecanamine dendrimer (PPI, generation 3.0, Sigma Aldrich) was dissolved in 1.5 mL reaction buffer containing 50 mM MES, pH 6.0. 11.2 g succinic acid (100 eq. per primary amine, Sigma-Aldrich) was dissolved in 30 mL of the same reaction buffer. The solutions were pooled and the pH readjusted to 6.0. To start the reaction 1.81 g 1-Ethyl-3-(3-dimethylaminopropyl)carbodiimide (EDC, 10 eq. per primary amine, Sigma Aldrich) diluted in 2 mL reaction buffer was added. The mixture was incubated overnight at RT on an overhead shaker. The product was purified by dialysis. For this purpose the reaction mixture was filled into slide-a-lyzer dialysis cassettes (3-12 mL, MWCO: 2,000 Da, Thermo Fisher) and dialyzed against water for 72 h. The water was exchanged twice per day. After dialysis the purified polymer was lyophilized.

10 mg of the lyophilized, succinic acid modified PPI was diluted in 2 mL reaction buffer containing 50 mM MES, pH 6.0. 0.776 g N,N'-Bis(2-aminoethyl)-1,3-propanediamine (100 eq./carboxyl group, Sigma Aldrich) was diluted in 2 mL of the same buffer. As the oligo(alkylene amine) was purchased as free base, the pH was readjusted to pH 6.0 by dropwise addition of 32% HCl. The polypropylenimine and the oligo(alkylene amine) solution were mixed. To start the reaction a 10-fold molar excess of 1-Ethyl-3-(3-dimethylaminopropyl)carbodiimide (EDC, Sigma Aldrich, diluted in 4 mL reaction buffer) per carboxyl group was added. The final volume was adjusted to 10 mL. The mixture was incubated for 5 h at RT on an overhead shaker. The product was purified by dialysis. For this purpose the reaction mixture was filled into a slide-a-lyzer dialysis cassette (3-12 mL, MWCO: 3,500 Da, Thermo Fisher) and dialyzed against water for 72 h. The water was exchanged twice per day. After dialysis the purified polymer was lyophilized.

Under same conditions the polymers listed in the following Table 4 were synthesized and tested:

TABLE 4

List of synthesized oligo(alkylene amine) modified polymers based on poly(allylamine).

| Polymeric backbone | | Oligo(alkylene amine) | | | |
|---|---|---|---|---|---|
| Name | Manufacturer/ Product nr. | Name | Manufacturer/ Product nr. | Resulting polymer | Example |
| Polypropylenimine hexadecaamine Dendrimer Generation 3.0 | Sigma aldrich, 469076 | N,N'-Bis(2-aminoethyl)-1,3-propanediamine | EvoBlock, KEMAM-003 | PPI-(2-3-2) | 27 |
| Polypropylenimine hexadecaamine Dendrimer Generation 3.0 | Sigma aldrich, 469076 | Triethylenetetramine | Sigma aldrich, 132098 | PPI-(2-2-2) | 27 |
| Polypropylenimine hexadecaamine Dendrimer Generation 3.0 | Sigma aldrich, 469076 | N,N'-Bis(2-aminopropyl)-1,3-propanediamine | Sigma aldrich, 404810 | PPI-(3-3-3) | 27 |

PRODUCTION EXAMPLE VII

Synthesis of Lipidoids Based on N,N'-Bis(2-aminoethyl)-1,3-propanediamine and 1-bromodecane 100 mg N,N'-Bis(2-aminoethyl)-1,3-propanediamine (0.623 µmol) was mixed with 10 mL tetrahydrofuran (THF). 815.2 µL N,N-Diisopropylethylamine (DIPEA) and 690.1 mg 1-bromodecane (3.12 µmol, (N-1) eq. where N is 2× amount of primary amines plus 1× amount of secondary amines per oligo(alkylene amine)) and mixed for 22 h at room temperature under constant shaking. The product was precipitated twice in cold n-hexane and dissolved in DCM. Solvents were removed by evaporation at 60° C. The resulting lipidoid was diluted in ethanol at a concentration of 50 mg/mL and stored at 4° C.

PRODUCTION EXAMPLE VIII

Synthesis of Lipidoids Based on N,N'-Bis(2-aminoethyl)-1,3-propanediamine and N-Dodecyl Acrylamide 100 mg N,N'-Bis(2-aminoethyl)-1,3-propanediamine (0.623 µmol) was mixed with 746.9 mg N-dodecyl acrylamide (3.12 µmol, (N-1) eq. where N is 2× amount of primary amine plus 1× amount secondary amine per oligo(alkylene amine)) and mixed for 192 h at 90° C. under constant shaking. The resulting lipidoid was diluted in ethanol at a concentration of 50 mg/mL and stored at 4° C.

PRODUCTION EXAMPLE IX

Synthesis of Lipidoids Based on N,N'-Bis(2-aminoethyl)-1,3-propanediamine and Dodecyl Acrylate 100 mg N,N'-Bis(2-aminoethyl)-1,3-propanediamine (0.623 µmol) was mixed with 750 mg dodecyl acrylate (3.12 µmol, (N-1) eq. where N is 2× amount of primary amine plus 1× amount secondary amine per oligo(alkylene amine)) and mixed for 22 h at 90° C. under constant shaking. The resulting lipidoid was diluted in ethanol at a concentration of 50 mg/mL and stored at 4° C.

PRODUCTION EXAMPLE X

Synthesis of Lipidoids Based on N,N'-Bis(2-aminoethyl)-1,3-propanediamine and 1,2-Epoxydodecane 100 mg N,N'-Bis(2-aminoethyl)-1,3-propanediamine (0.623 mmol) was mixed with 575.07 mg 1,2-Epoxydodecane (3.12 mmol, (N-1) eq. where N is 2× amount of primary amine plus 1× amount secondary amine per oligo(alkylene amine)) and mixed for 96 h at 80° C. under constant shaking. The resulting lipidoid was diluted in ethanol at a concentration of 50 mg/mL and stored at 4° C.

EXAMPLE 1

Testing of the Cationic Polymers on their Ability to Transport mRNA into Different Cell Lines.

Materials and Methods

Polyplex Formation:

For in vitro transfection polyplexes were formed in a volume of 44 µL. 22 µL of water for injection containing 1100 ng of mRNA (chemically modified mRNA comprising 25% of 5-methylcytidine and 2-thiouridine, respectively) coding for firefly luciferase was mixed with 22 µL water for injection containing the desired amount of polymer. The polymer to RNA ratio was defined as polymer nitrogen per nucleic acid phosphate group (N/P) and was tested using constant amounts of nucleic acid. After mixing the nucleic acid with the polymer the samples were incubated for 30 min at RT and used for transfection.

In Vitro Transfection of Polyplexes:

Polymers have been tested for transfection efficiency on 2 different cell lines (NIH3T3 and A549). 24 h prior to treatment 5,000 cells (NIH3T3) or 7,000 cells (A549) in 100 µL medium were seeded into a well of a 96-well plate. At day of transfection polyplexes were formed as described. To test different mRNA amounts a dilution series was performed mixing 50% of the polyplex solution with the same amount of medium (without FCS), taking this solution to perform a similar additional dilution step, etc. until a final concentration of 62.5 ng/20 µL was reached. 20 µL of every dilution step was added to the cells without medium exchange. 24 h after transfection the medium was removed. Cells were lysed by addition of 100 µl lysis buffer (25 mM Tris HCl, 0.1% TritonX 100, pH 7.8) and incubation for 20 min at RT. 80 µL of the lysate was filled into a well of a white 96-well plate and used for luciferase activity measurement in a Wallac Victor$^2$ (Perkin Elmer). For this purpose 100 µL of luciferase assay reagent (0.5 mM D-luciferin, 0.3 mM Coenzyme A, 33 mM DTT, 0.5 mM ATP, 1 mM magnesium carbonate, 2.7 mM magnesium sulfate, 0.1 mM EDTA, 20 mM tricine) was added and the chemiluminescence determined. Experiments were performed in triplicate.

Results

As shown in FIG. 1 the expression levels of luciferase vary extremely between the different modified polymers. The most efficient transfection levels on all cell types could be achieved using PAA8k-(2-3-2) or PAA8k-(3-2-3), in contrast modified polymers containing oligo(alkylene amine) side chains where one of the alkyl chains is replaced ((2-2-2) and (3-3-3)) or removed (2-2) the efficiency is drastically reduced by a factor of 10-1000. Elongation of all alkyl chains in the oligo(alkylene amine) (3-4-3) also reduces the efficiency by a factor of 100.

EXAMPLE 2

Complex Formation and mRNA Binding Ability of (2-3-2) and (3-2-3) Modified PAA8k.

Materials and Methods

Gel Migration Assay:

Polyplexes were formed as described in example 1 at N/P 1, 2, 4, 8 and 12. After incubation 5 µL sample was mixed with 5 µL 2×RNA loading dye (Fermentas) incubated for 10 min at 70° C. and loaded onto a 1% agarose gel containing ethidium bromide. Gel migration was performed in TBEbuffer at 150V for 30 min. Migrated nucleic acids were visualized by UV absorption at 260 nm.

RiboGreen Assay:

Polyplexes were formed as described in example 1 at N/P 1, 2, 4, 8 and 12. After incubation 2 μL sample were mixed with 148 μL water and 50 μL RiboGreen solution (1:200, QuantiT Ribogreen RNA Assay Kit, Invitrogen) in a white 96-well plate. The samples were incubated for 5 min at RT under exclusion of light and the fluorescence measured using a Wallac Victor$^2$ (Perkin Elmer, is, Ex.: 485 nm, Em.: 535 nm).

Results

Figure 3:
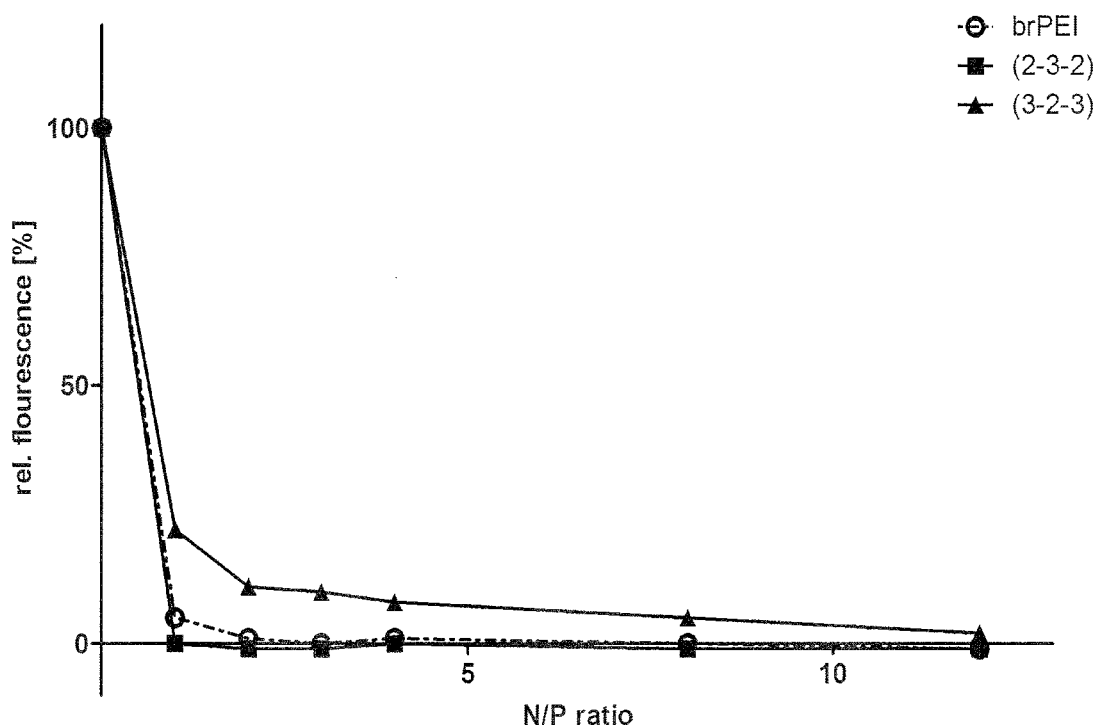
FIG. 3: RiboGreen assay for the determination of the complex formation ability of (2-3-2) and (3-2-3) modified PAA8k. Polyplexes were formed as described at indicated N/P ratios. The interaction of polymer and mRNA was analyzed via the addition of RiboGreen. This molecule interacts with nucleic acids, resulting in increased fluorescence signal at high amounts of mRNA. The better the interaction of the nucleic acid with the polymer, the lower the detected fluorescence signal. Signals are presented as relative fluorescence compared to a control containing the same amount of free mRNA.

The ability of polymers to interact with nucleic acids to form stable complexes is a critical characteristic for an efficient transport system. The interaction of the modified polymers with mRNA was analyzed via gel migration (FIG. 2) and RiboGreen assay (FIG. 3). When the polymer is able to interact with the nucleic acid, forming stable complexes, this leads to nanosized particles and charge inversion. Both effects result in hampered migration ability during agarose gel electrophoresis. As shown in FIG. 2 PAA8k modified with (2-3-2) or (3-2-3) lead to an absence/strong reduction of free mRNA compared to the control without polymer (N/P 0), indicating a strong interaction. This binding is as efficient as with the gold standard branched PEI (brPEI).

These data could be confirmed using the RiboGreen assay. In this assay an increased binding efficiency results in a reduced fluorescence signal. As shown in FIG. 3 the reduction of the fluorescence signal is for PAA8k-(2-3-2) and -(3-2-3) as strong as for brPEI. Thus, complexes with a similar stability are generated.

EXAMPLE 3

Transfection Efficiency is Independent of Polymer Backbone

Materials and Methods

Polyplex formation was performed according to example 1.

In Vitro Transfection of Polyplexes

For in vitro transfection and efficiency testing of polyplexes NIH3T3 cells were used. 24 h prior to treatment 5,000 cells in 100 μL medium containing 10% FCS were seeded into a well of a 96-well plate. At day of transfection the medium was exchanged against 100 μL medium without FCS. Polyplexes were formed as described. To test different mRNA amounts 20 μL (500 ng), 10 μL (250 ng), 5 μL (125 ng) and 2.5 μL (62.5 ng) were added to the medium. After 4 h incubation at 37° C. and 5% CO2 the medium was replaced by fresh medium containing 10% FCS. 24 h after transfection, the medium was removed. Cells were lysed and analyzed as described in example 1.

Results

Figure 4:
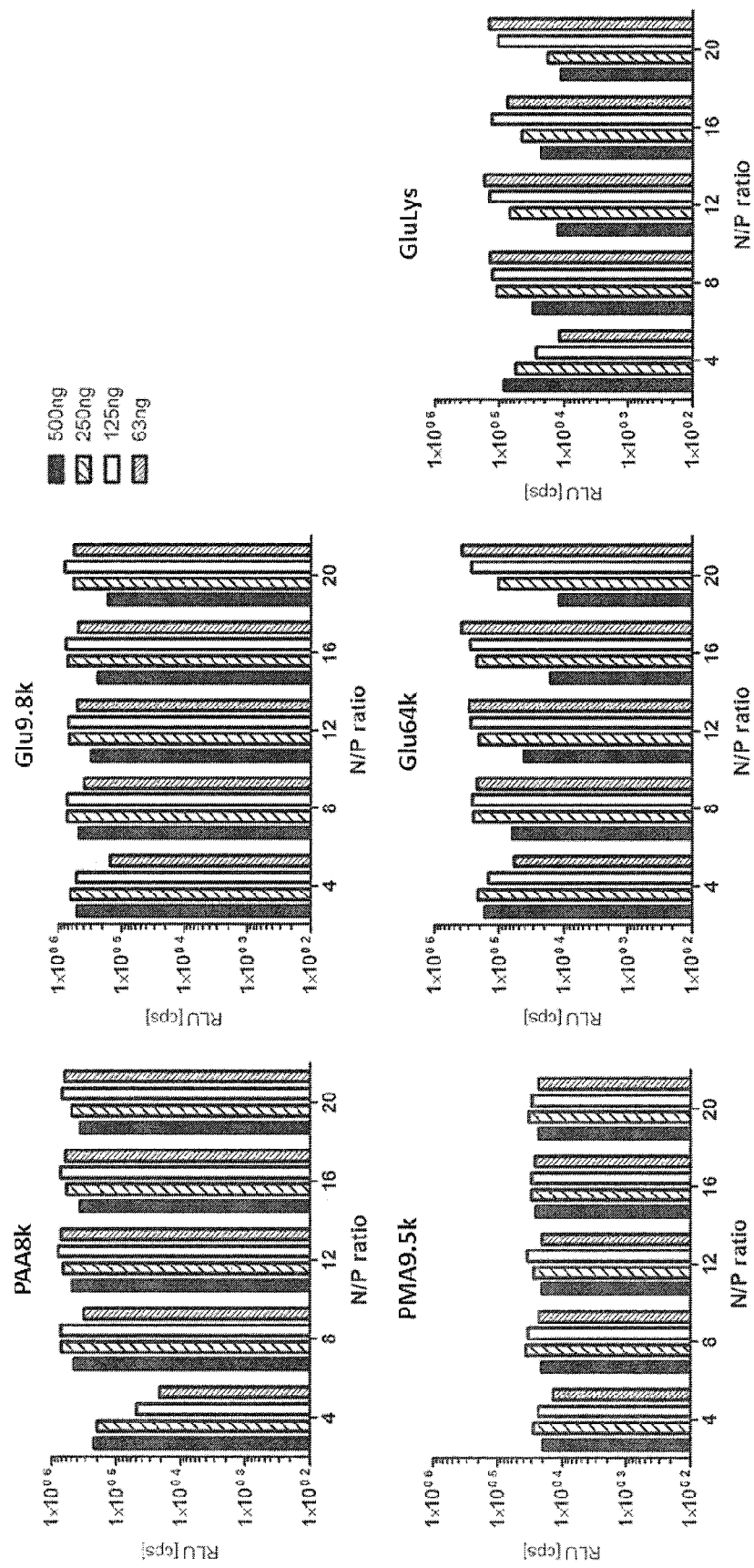
FIG. 4: Transfection efficiency of different N,N'-Bis(2-aminoethyl)-1,3-propanediamine (2-3-2) modified polymers. Polyplexes were formed using indicated N,N'-Bis(2-aminoethyl)-1,3-propanediamine modified polymers (PAA8k: poly(acrylic acid), MW 8,000 Da; Glu9.8k: poly(glutamic acid), MW 9,800 Da; PMA9.5k: poly(methacrylate), MW 9,500 Da; Glu64k: poly(glutamic acid), MW 64,000 Da; GluLys: poly(glutamic acid)-poly(lysine)-copolymer) (20,000-50,000 Da) and mRNA coding for firefly luciferase at N/P ratios between 4 and 20. After 24 h cells transfected with different amounts of mRNA (500, 250, 125 or 62.5 ng) were lysed and analyzed for luciferase activity.
Figure 5:
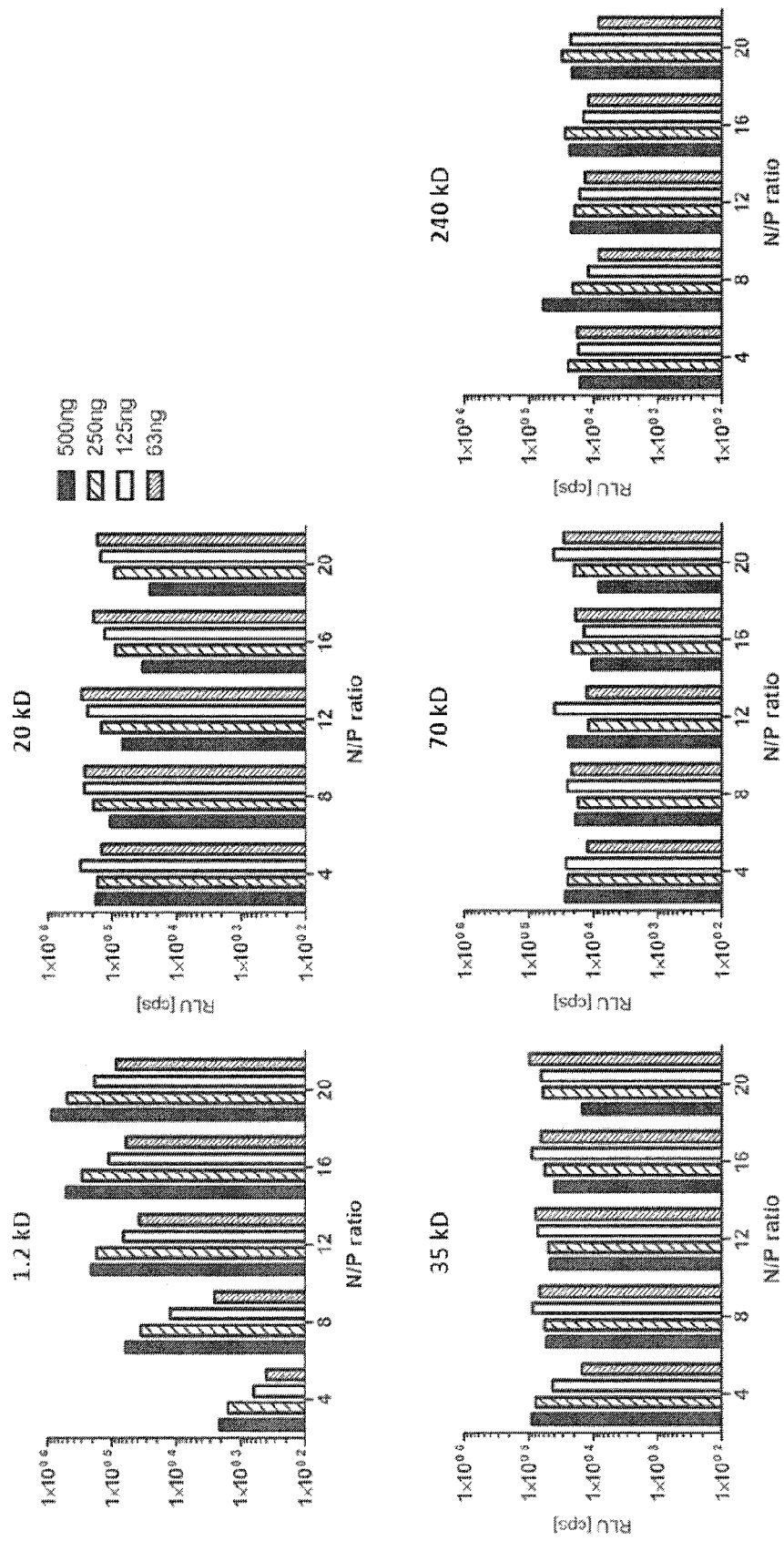
FIG. 5: Transfection efficiency of different molecular weights of N,N'-Bis(2-aminoethyl)-1,3-propanediamine (2-3-2) modified poly(acrylic acid). Polyplexes were formed using indicated molecular weights of poly(acrylic acid) modified with N,N'-Bis(2-aminoethyl)-1,3-propanediamine (2-3-2) and mRNA coding for firefly luciferase at N/P ratios between 4 and 20. After 24 h cells transfected with different amounts of mRNA (500, 250, 125 or 62.5 ng) were lysed and analyzed for luciferase activity.

To confirm that the ability to transport nucleic acids into cells using (2-3-2) modified polymers is independent of the backbone structure, different types of polymers (besides poly(acrylic acid), 8,000 Da example 1) have been modified with (2-3-2) under described conditions (table 1). Results show that different types of backbone-polymers (FIG. 4) as well as different chain length (FIG. 5) lead to significant reporter gene expression, when modified with the oligo (alkylene amine) (2-3-2).

EXAMPLE 4

Validation of Cell Toxicity of Polymers Modified with Different Types of Oligo(Alkylene Amine)s.

Materials and Methods

Transfections were performed according to example 3. The determination of living cells was performed using TACS MTT cell Proliferation Assay (Trevigen). Twenty-four hours after transfection the medium was exchanged against 100 μl fresh medium. After addition of 10 μl MTT reagent cells were incubated for 4 h at 37° C. and 5% $CO_2$. 100 μl detergent reagent was added followed by an incubation step at RT overnight. The read out was performed by absorption measurement at 570 nm using a Wallac Victor$^2$ (Perkin Elmer). Results are presented as % living cells compared to a non-treated control.

Results

Figure 6:
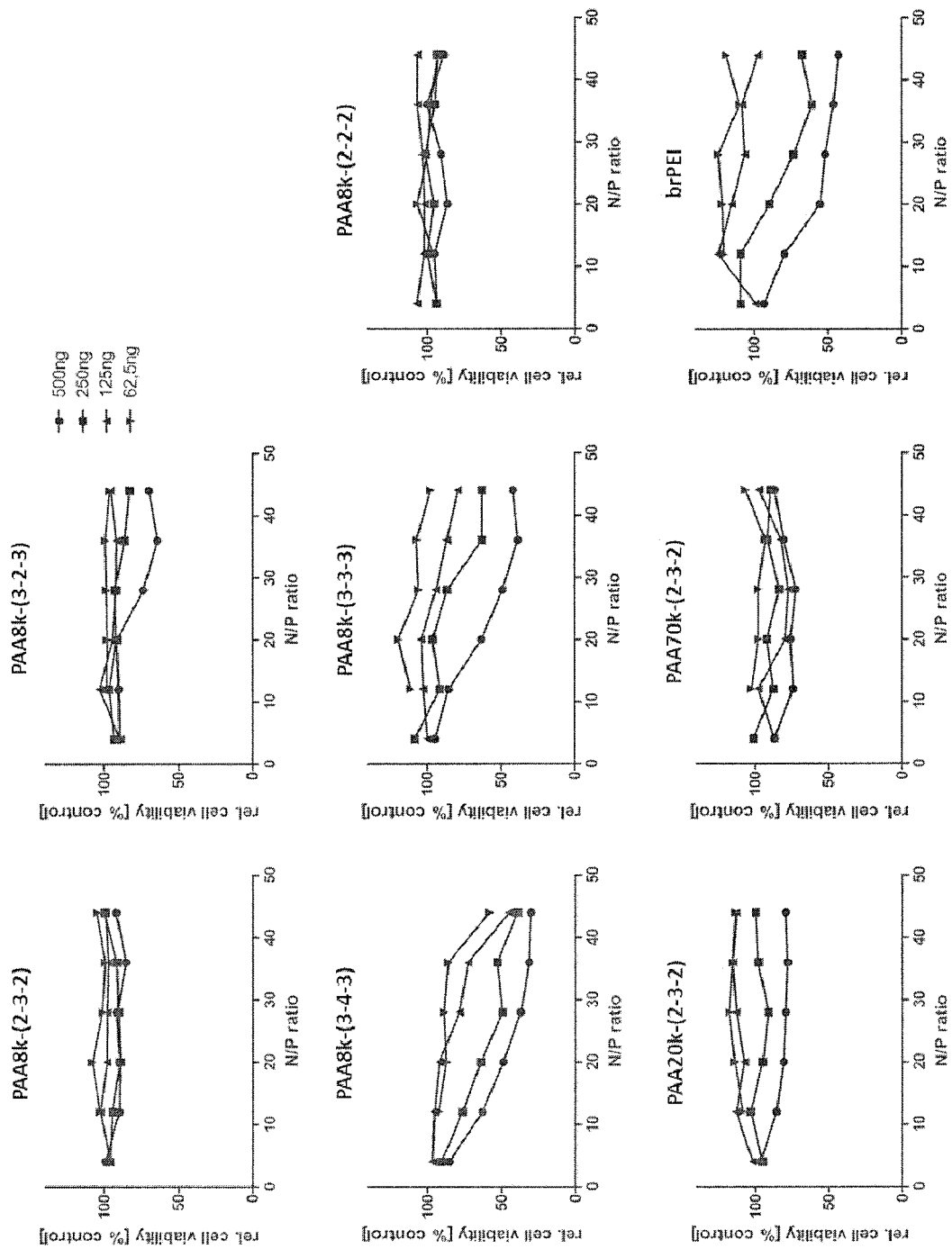
FIG. 6: Cytotoxicity of mRNA polymer formulations. Complexes comprising of pol(acrylic acid) (MW 8,000 Da, 20,000 Da and 70,000 Da) modified with indicated oligo(alkylene amine)s and mRNA coding for firefly luciferase were used for transfection at N/P ratios between 4 and 44 and different amounts of mRNA. After 24 h cell viability was determined as described. Data is shown as % survival compared to untransfected cells.

As shown in FIG. 6 the different modified polymers vary in terms of cell toxicity. While cells treated with complexes containing (2-3-2) and (3-2-3) modified poly(acrylic acid) show viability around 100% (PAA8k-(2-3-2), PAA8k-(3-2-3), PAA20k-(2-3-2), PAA70k-(2-3-2)), other alterations in the side chain type lead to strong toxicity (PAA8k-(3-4-3), PAA8k-(3-3-3)) comparable to the toxic standard (brPEI).

EXAMPLE 5

Messenger RNA Transport Efficiency in Mice

Materials and Methods

Animals:

Six to eight week-old female BALB/c mice were obtained from Janvier, Route Des Chines SecsBP5, F-53940 Le Genest St. Isle, France, and maintained under specific pathogen-free conditions. Mice were acclimatized to the environment of the animal facility for at least seven days prior to the experiments. All animal procedures were approved and controlled by the local ethics committee and carried out according to the guidelines of the German law of protection of animal life.

Polyplex Formation:

Polyplexes were formulated as follows: mRNA and PAA20k-(2-3-2) were diluted in 4.0 ml of double distilled water resulting in concentrations of 500 μg/ml mRNA and PAA20k-(2-3-2) at concentrations corresponding to N/P 10, 20, 30 or 40. The mRNA solution was pipetted to the polymer solution, mixed by pipetting up and down, to yield a final mRNA concentration of 250 μg/ml. The complexes were incubated for 20 min at ambient temperature before use.

Design of the Aerosol Device:

For the nebulization procedure in a whole body device, mice were placed in a 9.8×13.2×21.5 cm plastic box which can be sealed with a lid. At one narrow side of the box, four small holes are positioned as aerosol outflow. Through a whole at the opposite narrow side, the box is connected via a 2.1 cm diameter connecting piece to a 15.4 cm wide×41.5 cm long plastic cylinder. The bottom of the cylinder is evenly covered with 150 g of silica gel (1-3 mm, #85330; Fluka, Switzerland) for drying the aerosol which is produced by a jet nebulizer (PARI BOY® LC plus, PARI GmbH) connected to the other end of the cylinder. (Details described in Rudolph et al., J Gene Med. 2005, 7: 59-66).

Measurement of Luc Activity in Mouse Lungs Using In Vivo Bioluminescent Imaging:

Twenty-four hours post administration mice were euthanized by cervical dislocation. After opening the peritonea by midline incisions, lungs were dissected from animals and perfused with PBS. Lungs were snap-frozen in liquid nitrogen and homogenized in the frozen state. After addition of 400 µl of lysis buffer (250 mM Tris pH 7.8, 0.1% Triton X-100, Roche Complete Protease Inhibitor Cocktail Tablets) and incubation for 20 min on ice, luciferase activity in the supernatant was measured using a Lumat LB9507 tube luminometer (EG&G Berthold, Munich, Germany).

Results

Figure 7:
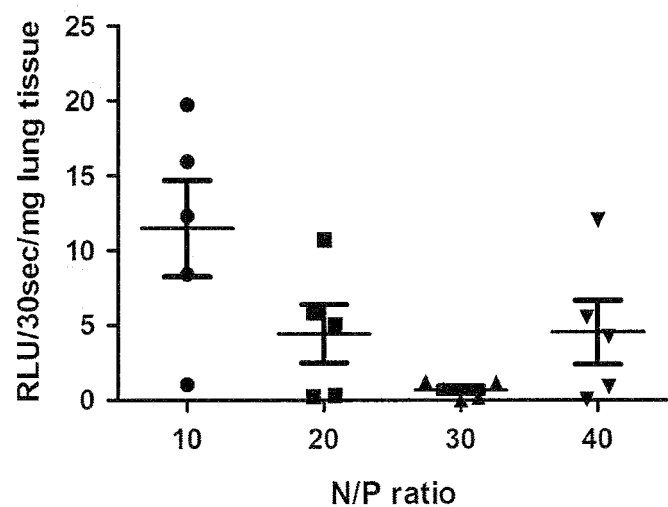
FIG. 7: Reporter protein expression levels of mice lungs. Polyplexes of PAA20k-(2-3-2) and mRNA coding for firefly luciferase were mixed at indicated N/P ratios and applied to the mice via aerosol.

The experiment shows that mRNA is effectively expressed in the lung cells of mice upon pulmonary aerosol delivery as a combination with PAA20k-(2-3-2), indicating that the polymer is able to efficiently transport the mRNA into lung cells in vivo (cf. FIG. 7).

EXAMPLE 6

Messenger RNA Transport Efficiency in Pigs

Materials and Methods

Polyplex Formation:

For in vivo transfection polyplexes were formed in a volume of 28 mL. 14 mL of water for injection containing 5.83 mg mRNA coding for firefly luciferase and 1.17 mg mRNA coding for ß-galactosidase and 14 mL of water for injection containing the desired amount of polymer were prepared and mixed via a two channel syringe pump (KDS-210-CE; KD Scientific). Two 20 mL syringes were filled using the withdrawal function of the device. The mixing was performed connecting the syringes via a T-piece (Discofix C 3SC, B. Braun) and usage of the infusion function of the mixing device. The polymer to mRNA ratio was defined as polymer nitrogen per nucleic acid phosphate group (N/P) and tested at N/P 10. After mixing the nucleic acid with the polymer the samples were incubated for 30 min at RT and 24 mL were used for nebulization. The remaining volume was used for physicochemical analysis. Particle size and zeta potential of the pure sample was determined using a Zetasizer Nano ZS (Malvern Instruments).

Experimental Procedure of Aerosol Application to Pigs:

Sedation of the pig was initiated by premedication with azaperone 2 mg/kg body weight, ketamine 15 mg/kg body weight, atropine 0.1 mg/kg body weight and followed by insertion of an intravenous line to the lateral auricular vein. The pig was anesthetized by intravenous injection of propofol 3-5 mg/kg body weight as required. Anesthesia was maintained with continuous intravenous infusion of 1% propofol as required. Ventilation parameters were matched with endexpiratory carbon dioxide and adjusted if necessary. Anesthesia, respiratory and cardiovascular parameters were monitored continuously using pulse oximetry, capnography, rectal temperature probe and reflex status. The pig received infusion of balanced electrolyte solution at 10 ml/kg/h. Duration of the anesthesia was approximately 80-120 min. The pig was killed with bolus injection of pentobarbital 100 mg/kg of body weight via the lateral ear vein after sedation after aerosol application was completed (Aeroneb mesh nebulizer). Lungs were excised and sliced approximately 1 cm thick tissue specimens were collected from various lung regions followed by incubation in cell culture medium for 24 h at 37° C. and 5% $CO_2$ in an incubator. For measurement of luciferase activity tissue specimens were incubated in a medium bath comprising D-Luciferin substrate in PBS (100 µg/ml) at 37° C. for 30 min and subjected to ex vivo luciferase bioluminescent imaging (IVIS 100, Xenogen, Alameda, USA).

Transmission Electron Microscopy of Polyplexes:

For transmission electron microscopy (TEM) one droplet of the mixture produced for aerosol application was used. The droplet of was placed onto a grid (Plano GmbH, Wetzlar). After incubation for 5 min, the droplet was removed with using a filter paper. The sample was stained with an uranyl acetate solution and analyzed via a transmission electron microscope (Jem 1011, Jeol).

Results

Figure 8:
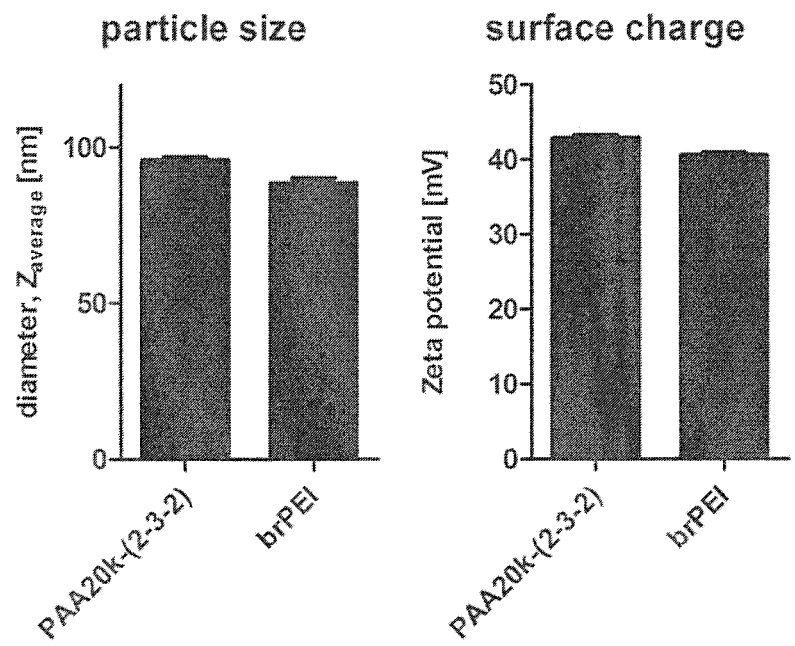
FIG. 8: Physicochemical properties of N,N'-Bis(2-aminoethyl)-1,3-propanediamine (2-3-2) modified poly(acrylic acid). Polyplexes were formed under in vivo conditions at N/P 10. Used polymer: poly(acrylic acid), MW 20,000 Da.
Figure 9:
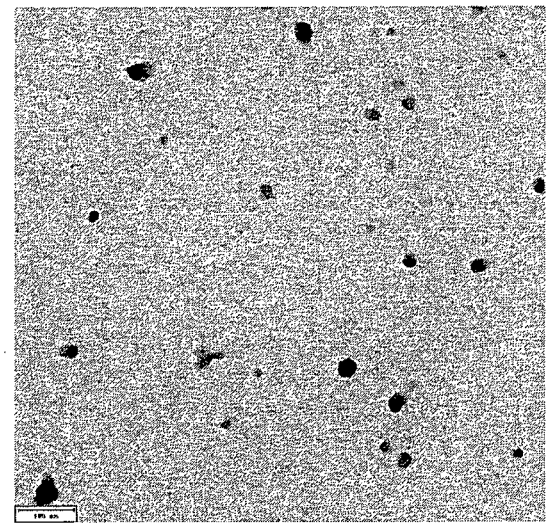
FIG. 9: Transmission electron microscopic picture of PAA20k-(2-3-2) and mRNA. Polyplexes were mixed at N/P 10 and analyzed via transmission electron microscopy. Scale bar: 100 nm. Used polymer: poly(acrylic acid), MW 20,000 Da.
Figure 10:
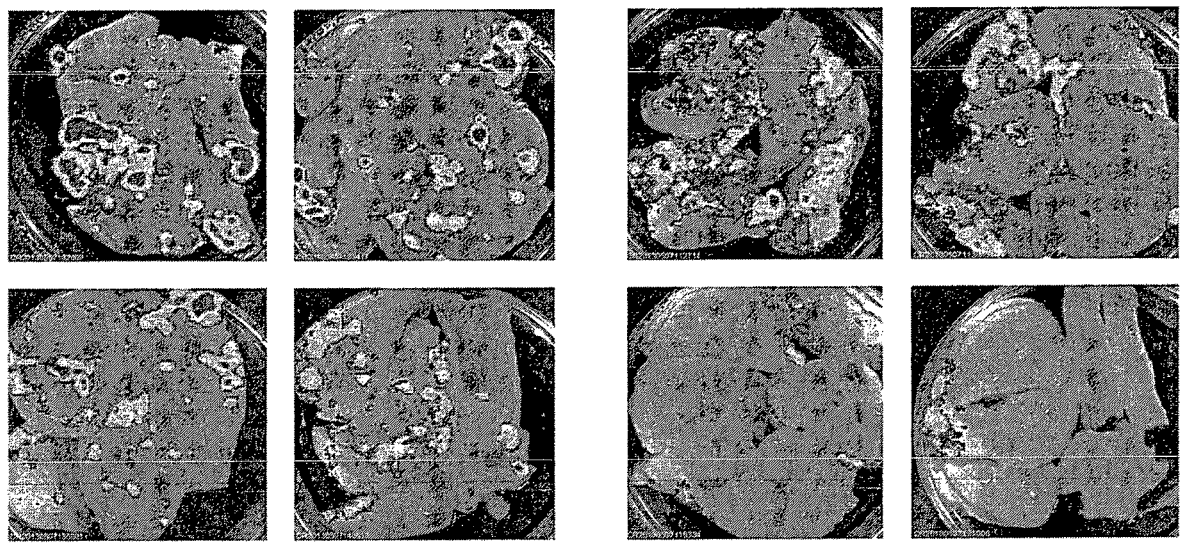
FIG. 10: Expression of firefly luciferase in porcine lung tissue after aerosol application of polyplex formulations. Left pictures brPEI N/P 10. Right pictures PAA20k-(2-3-2) N/P 10. Used polymer: poly(acrylic acid), MW 20,000 Da.

As shown in FIG. 8 PAA20k-(2-3-2) and mRNA at an N/P-ratio of 10 results in complexes with a hydrodynamic complex diameter below 100 nm and a surface charge (zeta potential) of 40 mV. Both parameters range in the same size as brPEI based complexes that have already shown to efficiently transport nucleic acids into cells in vivo. The particles show a round shape and a uniform size, when analyzed via TEM (FIG. 9). As shown in FIG. 10 these particles are able to efficiently deliver mRNA (coding for firefly luciferase) into lung tissue after aerosol application resulting in expression of the target protein. The expression levels were comparable to the nebulization of polyplexes formed with the gold standard brPEI.

EXAMPLE 7

Lyophilization Stability of Complexes

Materials and Methods

Preparation of Samples

PAA20k-(2-3-2)/mRNA (coding for metridia luciferase) complexes were formed as described in example 1 in 4 different vials at N/P 20 in a volume of 1 mL. One vial was used without further treatment for transfection, to the second vial 100 µL 11% trehalose solution was added to result in a final volume of 1% trehalose. The third vial was lyophilized and rehydrated in 1 mL water. The fourth vial was treated with 100 µl 11% trehalose prior to lyophilization and also rehydrated in 1 mL water.

Transfection:

24 h prior to transfection 5,000 NIH3T3 cells in 100 µL medium were seeded in a 96-well plate and incubated at 37° C. and 5% CO2. At day of transfection the medium was replaced against 100 µL fresh medium without FCS. 20, 10, 5 and 2.5 µL of every complex solution was added to the cells in triplicate resulting in transfection with 500, 250, 125 and 62.5 ng. 24 h after transfection the medium was removed, collected and replaced by fresh medium. This was repeated after 48 h and 72 h. The collected medium was analyzed for metridia luciferase activity. For that purpose, 50 µL medium was filled into a white 96-well plate, mixed with 20 µL coelenterazine solution (50 µM coelenterazine in 50 mM sodium phosphate-buffer) and the chemiluminescence signal measured using a Wallac Victor2 (Perkin Elmer).

Results

Figure 11:
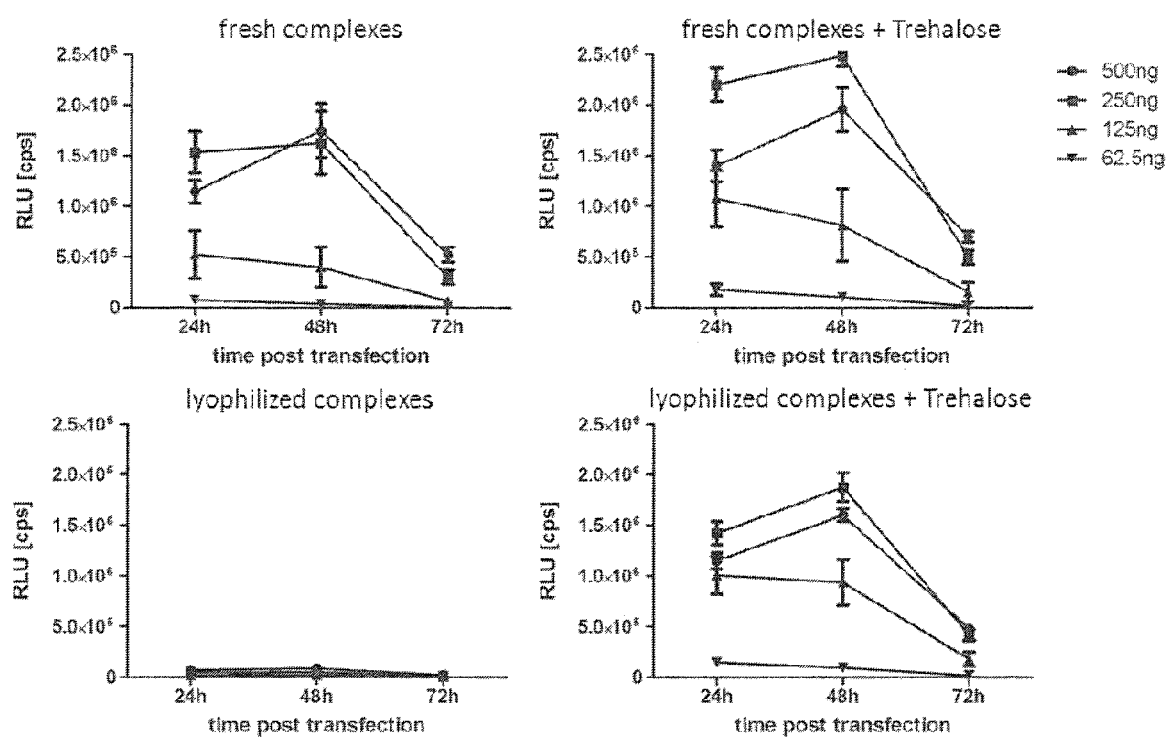
FIG. 11: Effect of trehalose on the ability to lyophilize PAA20k-(2-3-2) complexes. Complexes were formed as described and lyophilized in presents or absence of 1% trehalose. As demonstrated, trehalose is able to preserve mRNA transfection efficiency of these complexes after lyophilization and rehydration.

As shown in FIG. 11 fresh complexes lead to methridia luciferase expression after 24 h. The expression remains stable for further 24 h and then slowly decreases. This effect is not negatively influenced by the addition of trehalose but results in slightly increased expression levels. After lyophilization untreated complexes are not able to transfect cells resulting in absence of reporter protein expression. In contrast the addition of trehalose preserves the complex and the resulting transfection efficiency.

EXAMPLE 8

Usage of PAA8k-(2-3-2) and PAA8k-(3-2-3) as Transport System for Plasmid DNA.

Materials and Methods

Polyplex Formation:

Polyplexes were formed as described in example 1 using plasmid DNA (pCMVLuc, Plasmid Factory) coding for firefly luciferase instead of mRNA.

In Vitro Transfection Using Polyplexes:

Transfection experiments were performed as described in example 3.

Results

Figure 12:
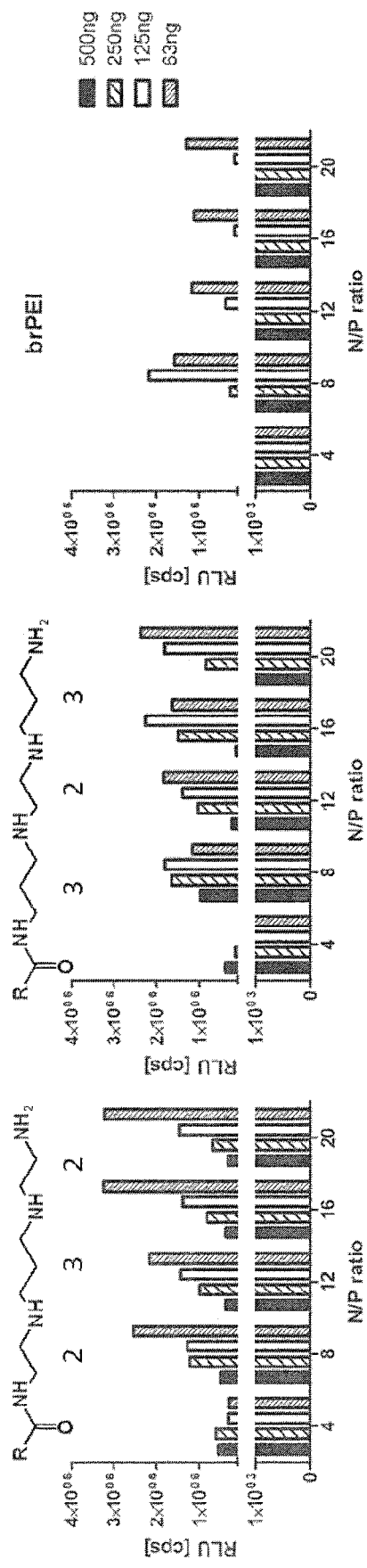
FIG. 12: Effect of (2-3-2) and (3-2-3) modified polymers on DNA transfection efficiency. Polyplexes were formed using poly(acrylic acid) (MW: 8,000 Da) with indicated side chain modifications and pDNA coding for firefly luciferase (pCMVLuc) at N/P ratios between 4 and 20. After 24 h cells transfected with different amounts of DNA (500, 250, 125 or 62.5 ng) were lysed and analyzed for luciferase activity. As control branched PEI (brPEI) 25 kDa was used as transfection reagent.

In this experiment the efficiency of N,N'-Bis(2-aminoethyl)-1,3-propanediamine (2-3-2) modified polymers (poly (acrylic acid) in DNA transport and resulting protein expression, was analyzed in comparison to the gold standard branched PEI (brPEI, FIG. 12). The results show clearly that the transfection of NIH3T3 cells with complexes composed of pDNA and oligo(alkylene amine) (2-3-2) and (3-2-3) modified polymers leads to a significant increase in reporter protein expression. The expression level is even higher as of the gold standard.

EXAMPLE 9

Usage of PAA20k-(2-3-2) as Transport System for siRNA to Induce RNA Interference.

Materials and Methods

Complexes were formed as described in example 1 using GL3-Luc siRNA (Qiagen). For titration of the siRNA amount the complexes were step wise diluted after 30 min incubation at RT. For that purpose 22 µL of complex solution was mixed with 22 µl medium without FCS. 22 µL of this dilution was again mixed with 22 µL medium without FCS. This dilution series was repeated until a siRNA concentration of 7.8 ng per 20 µL was achieved. 201 µL of every dilution step was used for transfection as described under example 1 using HeLa cells stably expressing firefly luciferase (HeLa-Luc). As control for the specificity of an RNA interference based down regulation of luciferase expression a control siRNA, not influencing cellular expression (GFP22-siRNA; Qiagen) was used for transfection under same conditions. Results are shown as relative luciferase expression compared to non-treated control cells.

Results

Figure 13:
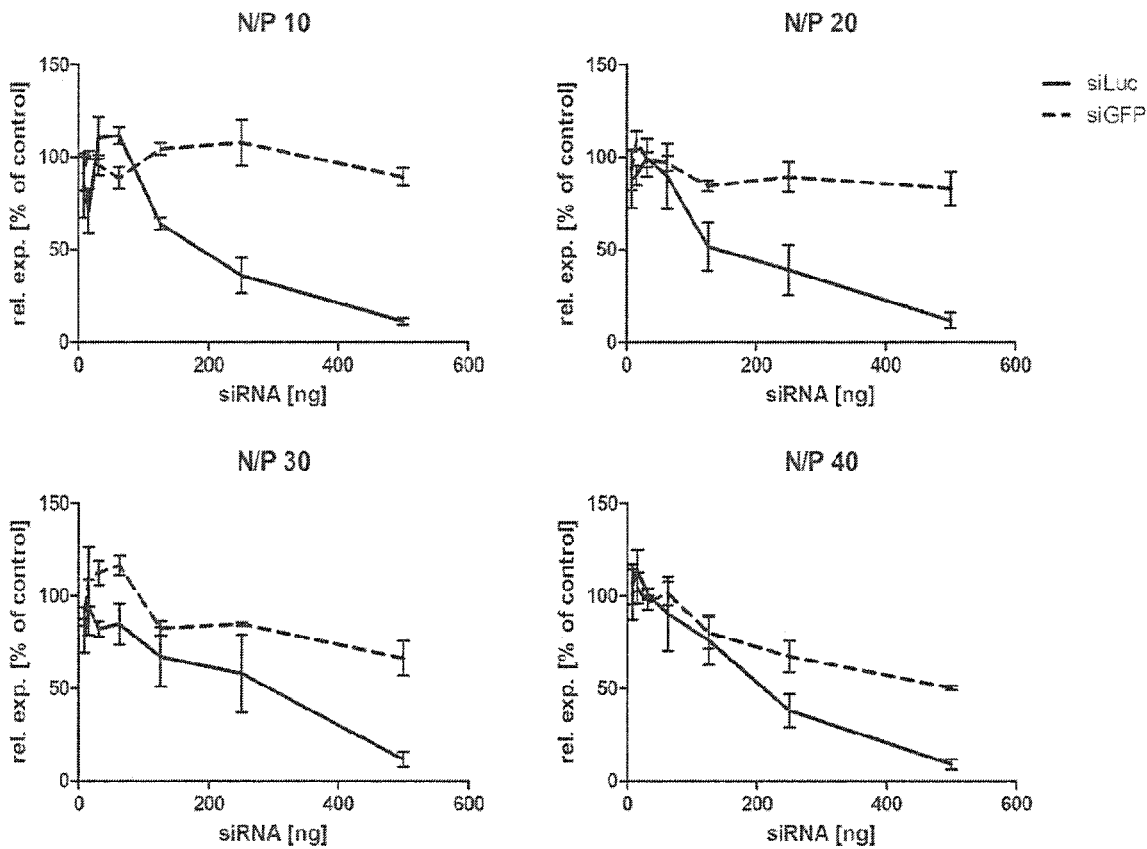
FIG. 13: RNAi induced gene silencing using complexes of GL3-Luc-siRNA and N,N'-Bis(2-aminoethyl)-1,3-propanediamine (2-3-2) modified poly(acrylic acid). HeLa cells stably expressing firefly luciferase were transfected using complexes of siRNA against firefly luciferase siRNA (siLuc) or control siRNA (siGFP) and PAA20k-(2-3-2) at indicated N/P ratios and different siRNA amounts. Luciferase expression was analyzed after 24 h and is shown as relative expression compared to untreated cells.

As shown in FIG. 13 the complex of GL3-Luc-siRNA (siLuc) and PAA20k-(2-3-2) leads to the down regulation of luciferase expression. This effect is dose dependent (reduced effect at lower siRNA amounts) and specific (no effect on unspecific siRNA (siGFP)). At higher N/P ratios an additional unspecific effect could be observed as indicated by the decreased signal of siGFP treated cells.

EXAMPLE 10

Beneficial mRNA Transport Efficiency of Lipidoid Structures Based on Oligo(Alkylene Amine) (2-3-2)

Material and Methods

Lipidoid/mRNA Complex Formation

Lipidoids were synthesized and diluted as described in production example IV. For transfection 250 ng mRNA coding for firefly luciferase in 50 µL water was mixed under optimized conditions with 4,000 ng of lipidoid in 50 µL water resulting in a w/w ratio (weight lipidoid/weight mRNA) of 16. After 30 min incubation at RT the samples were used for transfection.

In Vitro Transfection Using Lipidoid/mRNA Complexes 24 h prior to treatment 5,000 NIH3T3 cells in 100 µL medium were seeded into a well of a 96-well plate. At day of transfection polyplexes were formed as described. To test different mRNA amounts a dilution series was performed mixing 50% of the complex solution with the same amount of medium (without FCS), taking this solution to perform a similar additional dilution step, etc. until a final concentration of 15.6 ng/50 µL was reached. Prior to transfection the medium was removed from the cells and replaced by 1001 µL medium without FCS. 50 µL of every dilution step was added to the cells and incubated for 4 h at 37° C. and 5% CO2. After that the medium is replaced again by fresh medium containing 10% FCS. 24 h after transfection the medium was removed. Cells were lysed and lysates analyzed for reporter protein activity as described in example 1.

Results

Figure 14:
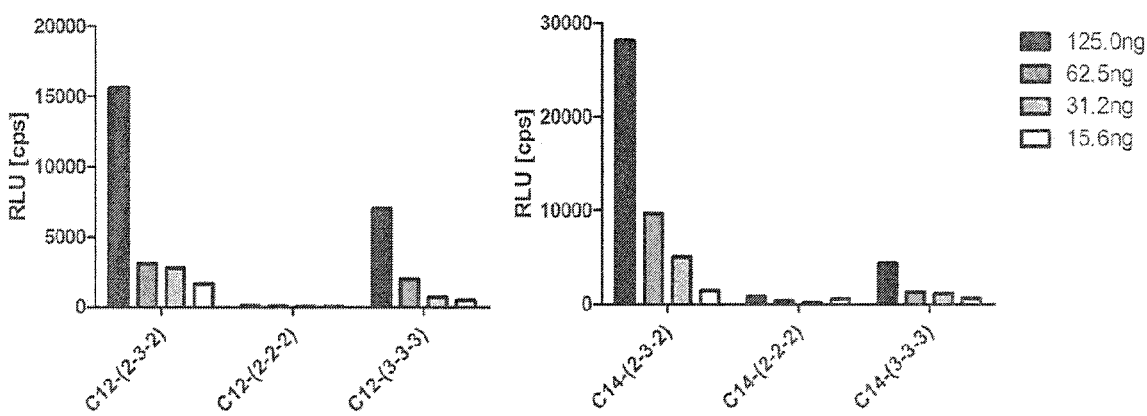
FIG. 14: Firefly luciferase activity after transfection of NIH3T3 cells with different lipidoid/mRNA complexes. Complexes were formed between mRNA and lipidoids based on (2-3-2) or the control oligo(alkylene amine)s (2-2-2) and (3-3-3) at a w/w-ratios (weight lipidoid/weight mRNA) of 16.
Figure 15:
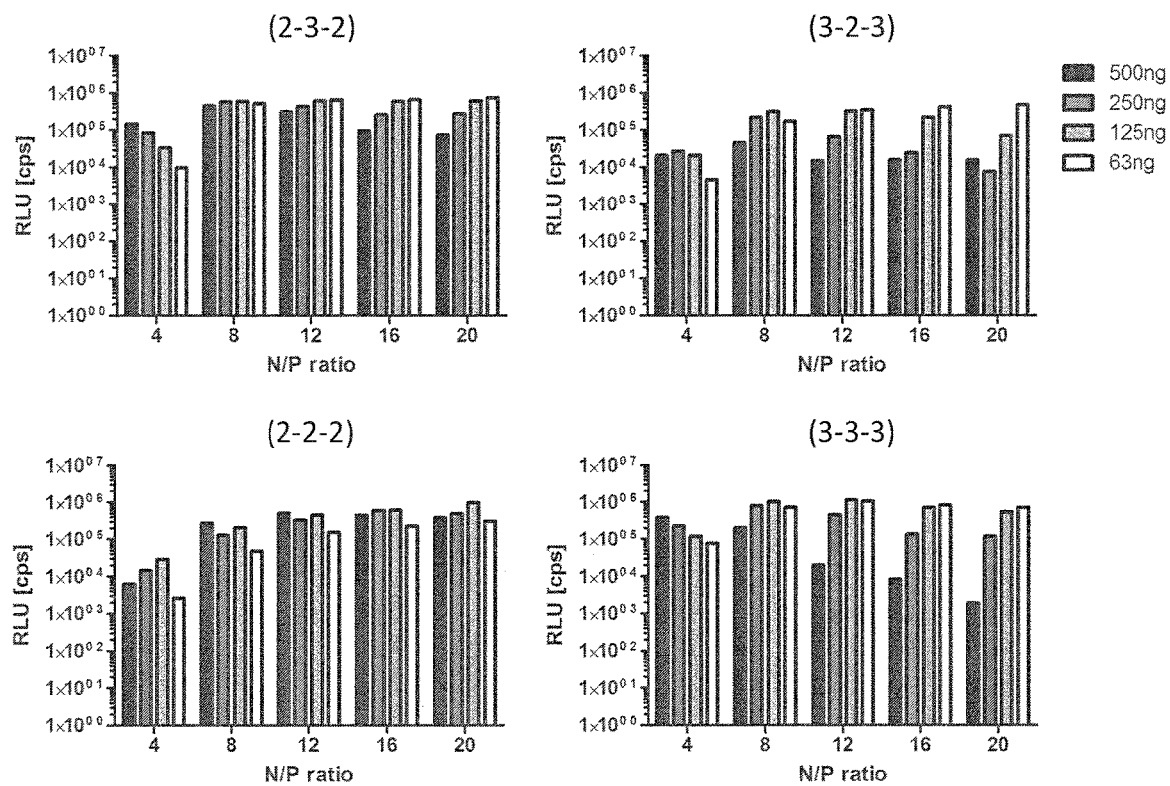
FIG. 15: Effect of oligo(alkylene amine) side chain modification of poly(acrylic acid) on DNA transfection efficiency. Polyplexes were formed using poly(acrylic acid) (MW: 8,000 Da) with indicated side chain modifications and pDNA coding for firefly luciferase (pCMVLuc) at indicated N/P ratios. After 24 h cells transfected with different amounts of DNA (500, 250, 125 or 62.5 ng) were lysed and analyzed for luciferase activity. In contrast to mRNA transfection (see FIG. 1) oligo(alkylene amine) side chain modification does not markedly affect transfection efficiency.

As shown in FIG. 14 lipidoids based on structure (2-3-2) lead to higher expression level of firefly luciferase then similar structures based on (2-2-2) or (3-3-3). This effect could be demonstrated independently of the attached alkyl chain (C12 or C14). As the activity of firefly luciferase correlates to its expression level in the cell in therefor to the efficiency of mRNA transport into the cell, these results show that (2-3-2) based lipidoids transport mRNA more efficient into cells in vitro.

EXAMPLE 11

Messenger RNA Transport Efficiency of Lipidoid Formulations in Mice after Intravenous Administration Materials and Methods Animals:

Six to eight week-old female BALB/c mice were obtained from Janvier, Route Des Chênes SecsBP5, F-53940 Le Genest St. Isle, France, and maintained under specific pathogen-free conditions. Mice were acclimatized to the environment of the animal facility for at least seven days prior to the experiments. All animal procedures were approved and controlled by the local ethics committee and carried out according to the guidelines of the German law of protection of animal life.

Lipidoid Formulations:

Lipidoids were formulated with mRNA as follows: C12-(2-3-2), DOPE, Chol and DSPE-PEG2k (3.6:0.18:0.76:1 weight ratio) were dissolved in ethanol and rapidly injected into a citrate-buffered solution (10 mM citric acid, 150 mM NaCl, pH=4.5) comprising chemically modified mRNA encoding firefly luciferase at an lipid/mRNA weight ratio of 10.5 to yield a final ethanol concentration of 20% and dialized against water. The resulting lipidoid/mRNA complexes resulted in positively charged nanoparticles (92.6±0.7 nm; 21.0±0.2 mV) and were injected intravenously into the tail vein of restrained mice. In a second experiment, the lipidoid/mRNA complexes were adjusted to PBS before intravenous injection which resulted in nearly uncharged nanoparticles (91.5±0.6 nm; −0.7±0.2 mV).

Measurement of Luc Activity in Mice Using In Vivo Bioluminescent Imaging:

Twenty-four hours post administration mice were anaesthetized by intraperitoneal injection of medetomidine (11.5 µg/kg BW), midazolame (115 µg/kg BW) and fentanyl (1.15 µg/kg BW). D-luciferin substrate (3 mg/100 µl PBS per mouse) was applied via intraperitoneal injection. Bioluminescence was measured 10 minutes later, using an IVIS 100 Imaging System (Xenogen, Alameda, USA) and the camera settings: Bin(HS), field of view 10, f1 f-stop, high-resolution binning and exposure-time of 5 min. The signal was quantified and analyzed using the Living Image Software version 2.50 (Xenogen, Alameda, USA).

Results

Figure 16:
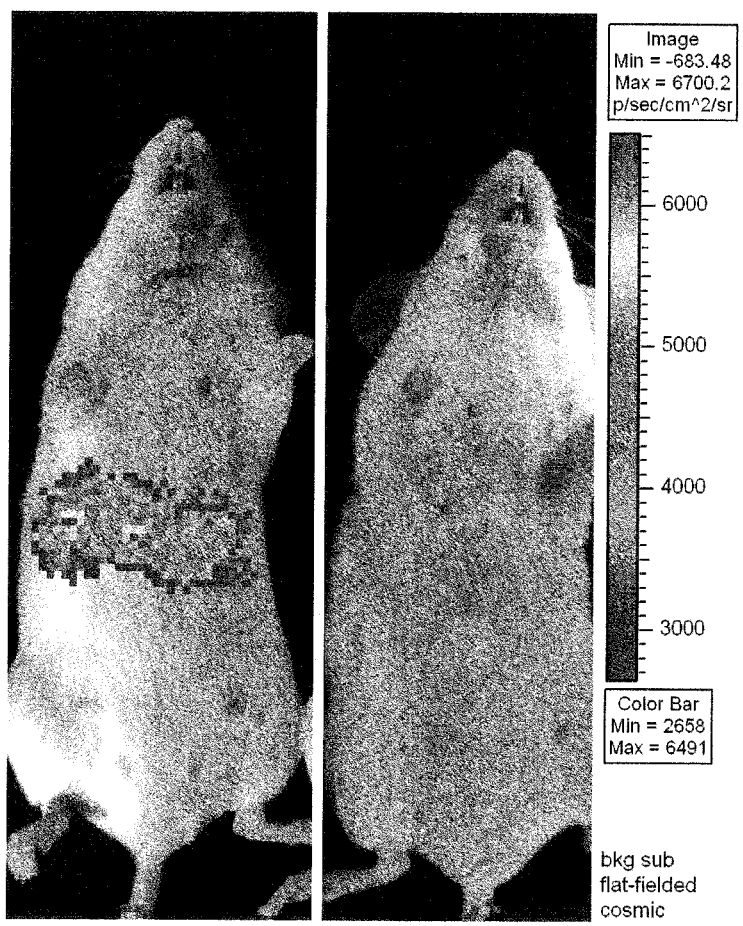
FIG. 16: Expression of firefly luciferase in murine liver and spleen after intravenous injection of lipidoid formulations. Left: mRNA encoding firefly luciferase formulated with lipidoid C12-(2-3-2) (C12-(2-3-2):DOPE:Cholesterol: DSPE-PEG2k; 3.6:0.18:0.76:1 weight ratio) in PBS for injection; Right: mRNA encoding firefly luciferase formulated with lipidoid C12-(2-3-2) (C12-(2-3-2):DOPE:Cholesterol:DSPE-PEG2k; 3.6:0.18:0.76:1 weight ratio) in water for injection. Only formulations ins PBS lead to expression in liver and spleen (PBS: 1.6404×10^5 photons/s; water: non detectable).

The experiment shows that mRNA is effectively expressed in the abdominal region of the mice only when lipidoid/mRNA complexes were formulated in PBS carrying a nearly neutral charge but not when formulated in water (cf. FIG. 16).

EXAMPLE 12

Messenger RNA Transport Efficiency of Lipidoid Formulations in Mice to Different Organs after Intravenous Administration Materials and Methods Animals:

Six to eight week-old female BALB/c mice were obtained from Janvier, Route Des Chênes SecsBP5, F-53940 Le Genest St. Isle, France, and maintained under specific pathogen-free conditions. Mice were acclimatized to the environment of the animal facility for at least seven days prior to the experiments. All animal procedures were approved and controlled by the local ethics committee and carried out according to the guidelines of the German law of protection of animal life.

Lipidoid Formulations:

Lipidoids were formulated with mRNA as follows: Lipidoid, DOPE, Chol and DMPE-PEG2k (8:6:5:1 molar ratio) were dissolved in ethanol and rapidly injected into a citrate-buffered (10 mM citric acid, 150 mM NaCl, pH=4.5) solution comprising chemically modified mRNA encoding firefly luciferase at an N/P ratio of 15 to yield a final ethanol concentration of 20% and dialized against water. The resulting lipidoid/mRNA complexes resulted in positively charged nanoparticles. The lipidoid/mRNA complexes were adjusted to PBS before intravenous injection which resulted in nearly uncharged nanoparticles (see Table 5).

TABLE 5

| | C12-(2-3-2) | | C14-(2-3-2) | | C16-(2-3-2) | |
|---|---|---|---|---|---|---|
| | water | PBS | water | PBS | water | PBS |
| size (nm) | 84.3 ± 0.7 | 84.9 ± 0.7 | 85.3 ± 0.6 | 86.6 ± 0.5 | 125.7 ± 0.2 | 120.6 ± 1.2 |
| zeta (mV) | 11.1 ± 0.1 | −0.9 ± 0.3 | 9.2 ± 0.2 | −0.7 ± 0.2 | 8.6 ± 0.2 | 1.0 ± 0.2 |

Measurement of Luc Activity in Mice Using In Vivo Bioluminescent Imaging:

Twenty-four hours post administration mice were anaesthetized by intraperitoneal injection of medetomidine (11.5 µg/kg BW), midazolame (115 µg/kg BW) and fentanyl (1.15 µg/kg BW). D-luciferin substrate (3 mg/100 µl PBS per mouse) was applied via intraperitoneal injection. Bioluminescence was measured 10 minutes later, using an IVIS 100 Imaging System (Xenogen, Alameda, USA) and the camera settings: Bin(HR), field of view 10, f1 f-stop, high-resolution binning and exposure-time of 30 s. The signal was quantified and analyzed using the Living Image Software version 2.50 (Xenogen, Alameda, USA). Subsequently, organs were dissected and imaged separately again.

Results

Figure 18:
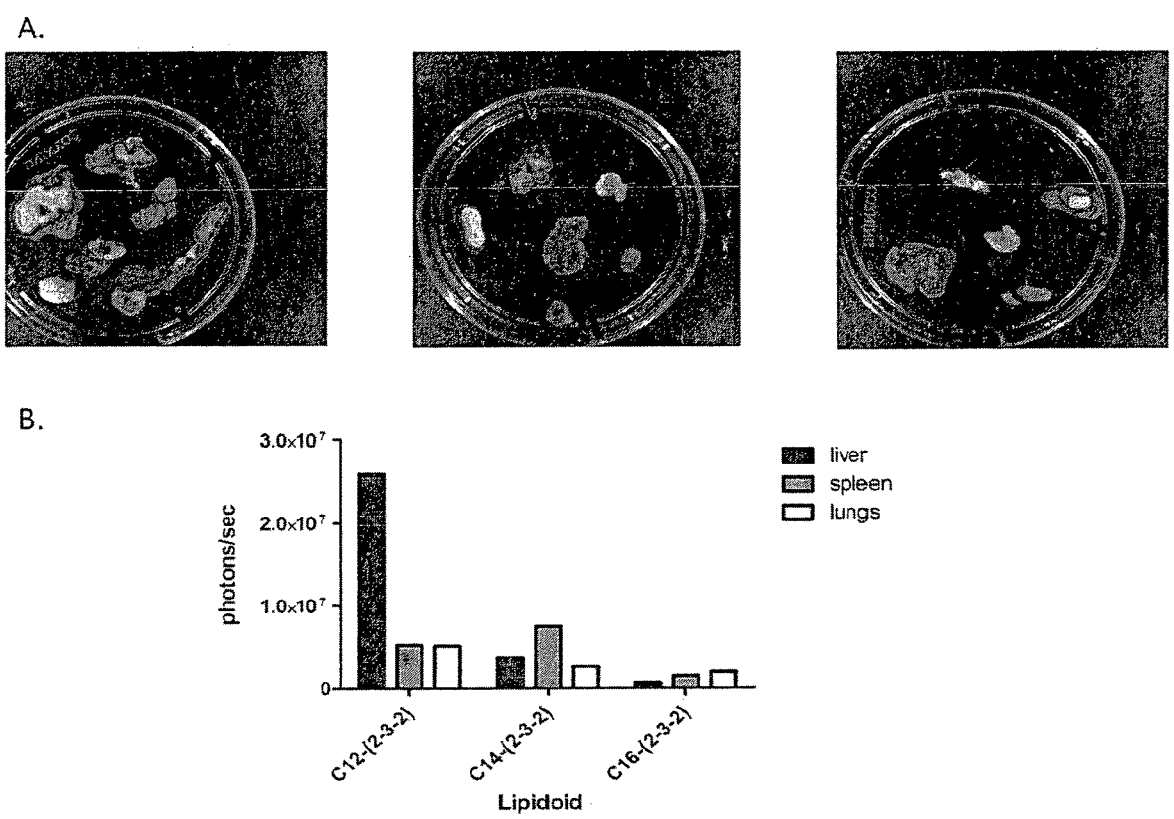
FIG. 18: Expression of firefly luciferase in murine liver and spleen after intravenous injection of lipidoid formulations. Liver, spleen, kidney, stomach, heart, lungs and brain were excised from treated mice shown in FIG. 17 and imaged for luciferase expression. A. bioluminescence image: Left: mRNA encoding firefly luciferase formulated with lipidoid C12-(2-3-2) (C12-(2-3-2):DOPE:Cholesterol: DSPE-PEG2k; 8:6:5:1) in PBS for injection; Middle: mRNA encoding firefly luciferase formulated with lipidoid C14-(2-3-2) (C14-(2-3-2):DOPE:Cholesterol:DSPE-PEG2k; 8:6:5:1) in PBS for injection; Right: mRNA encoding firefly luciferase formulated with lipidoid C16-(2-3-3) (C16-(2-3-2):DOPE:Cholesterol:DSPE-PEG2k; 8:6:5:1) in PBS for injection. Luciferase expression in liver decreased with increasing alkane chain length of lipidoids (C16<C14<C12) and was hardly detectable for C16. Luciferase expression in spleen was highest for C14. Some luciferase expression was observed in lungs but none was observed in heart, kidney, stomach or brain. B. Quantification of bioluminescence signal from A.

The experiment shows that mRNA is effectively expressed in the abdominal region of the mice and increased with decreasing alkane chain length (cf. FIG. 17 A, B). Furthermore, the experiment showed that mRNA delivery to the liver decreased with increasing alkane chain length of lipidoids (C16<C14<C12) and was hardly detectable for C16. Luciferase expression in spleen was highest for C14. Some luciferase expression was observed in lungs but none was observed in heart, kidney, stomach or brain (cf. FIG. 18 A, B).

EXAMPLE 13

Comparison of the Efficiency of Different Transfection Reagents on their Ability to Deliver pDNA and mRNA.

Materials and Methods

Polyplex Formation:

Polyplexes were formed as described in example 1 using plasmid DNA (pCMVLuc, Plasmid Factory) coding for firefly luciferase or mRNA coding for firefly luciferase.

In Vitro Transfection Using Polyplexes:

Transfection experiments were performed as described in example 3

Results

Figure 19:
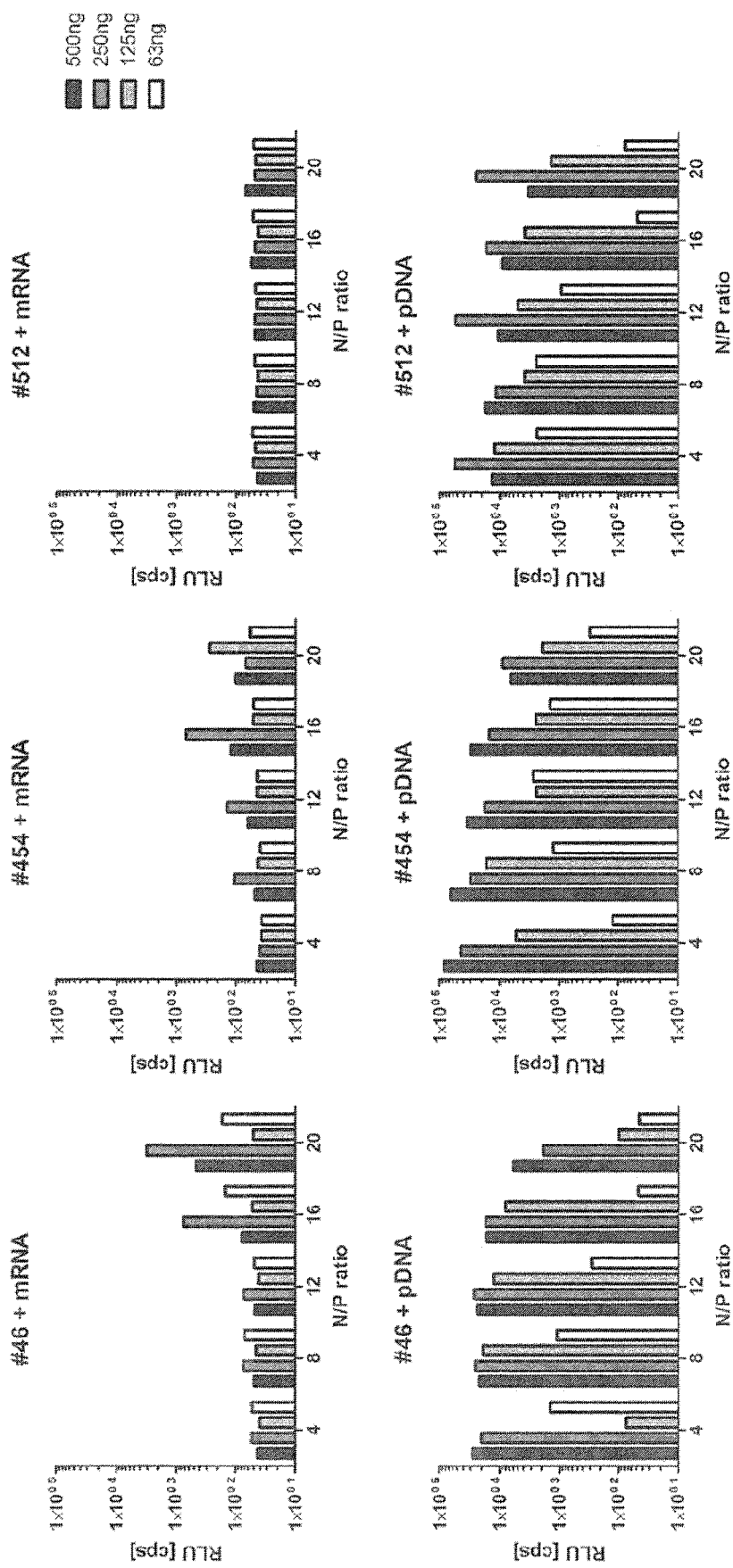
FIG. 19: Comparison of the efficiency of different transfection reagents on their ability to deliver pDNA and mRNA. Polyplexes were formed using indicated transfection reagents (Structures according to nomenclature of corresponding patent WO 2011/154331: #46 C-Stp3-C—K-OleA2; #454: C-Y3-Stp2-K(K-OleA2)-Stp2-Y3-C; #512: C-Sph3-K(Sph3-C)2). As nucleic acid payload either mRNA or pDNA (pCMVLuc) coding for firefly luciferase was used at indicated N/P ratios. After 24 h NIH3T3 cells transfected with different amounts of mRNA (500, 250, 125 or 63 ng) were lysed and analyzed for luciferase activity.

The experiment was performed to demonstrate, if the transfection efficiency is exclusively related to the transfection medium (polymer/lipidoid) or also to the type of nucleic acid. The results (FIG. 19) show clearly that transfection reagents that transport pDNA efficiently, are not necessarily efficient vehicles for mRNA transport. Thus a carrier system with a high transfection efficiency for pDNA does not allow an efficiency prediction mRNA.

EXAMPLE 14

Comparison of the Transfection Efficiency of PAA8k, modified with N,N'Bis(2-aminoethyl)-1,3-propanediamine (2-3-2) or N,N'Bis(2-aminoethyl)-1,3-butanediamine (2-4-2)

Materials and Methods

Figure 20:
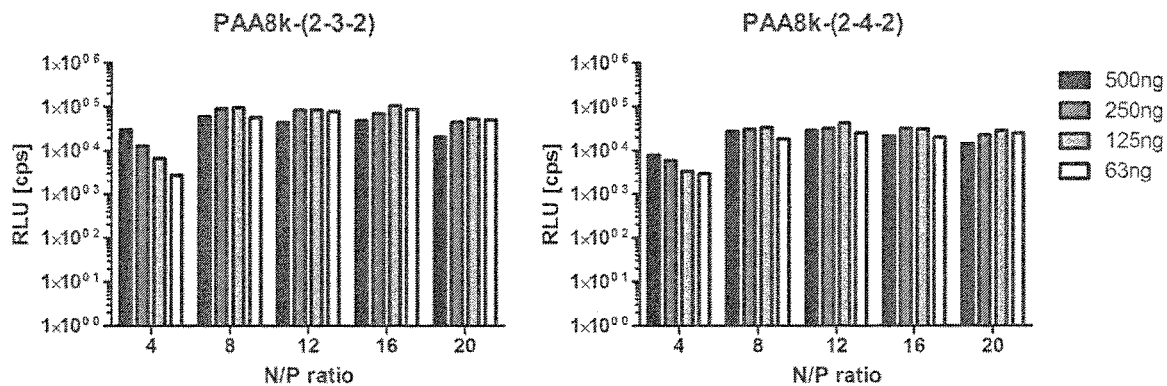
FIG. 20: Comparison of the transfection efficiency of PAA8k, modified with N,N'-Bis(2-aminoethyl)-1,3-propanediamine (2-3-2) or N,N'-Bis(2-aminoethyl)-1,3-butanediamine (2-4-2). Polyplexes were formed using PAA8k either modified N,N'-Bis(2-aminoethyl)-1,3-propanediamine (2-3-2) or N,N'-Bis(2-aminoethyl)-1,3-butanediamine (2-4-2) and mRNA coding for firefly luciferase at indicated N/P ratios. After 24 h NIH3T3 cells transfected with different amounts of mRNA (500, 250, 125 or 63 ng) were lysed and analyzed for luciferase activity.

Polyplex Formation:
Polyplexes were formed as described in Example 1.
In Vitro Transfection Using Polyplexes:
Transfection experiments were performed as described in Example 3
Results To further investigate if the efficiency of the polymers modified with (2-3-2) is strongly related to the structure (2-3-2) or shows similar efficiency for any other structure 2-X-2 with X>2, PAA8k was modified with N,N'-Bis(2-aminoethyl)-1,3-butanediamine (2-4-2). The comparison with PAA8k-(2-3-2) with PAA8k-(2-4-2) (FIG. 20) shows that both polymers result in almost identical high luciferase expression levels after transfection of mRNA coding for firefly luciferase. This demonstrates that a polymer modified with structure (2-X-2) with X>2 in general results in a transfection reagent with an improved mRNA transport efficiency compared to the modification with other oligo (alkyl amine)s.

EXAMPLE 15

Transmission Electron Microscopy of Lipidoid Formulations

Materials and Methods

Lipidoid Formulation:

Lipidoids were formulated with mRNA as follows: C10-(2-3-2), 1,2-Dioleoyl-sn-glycero-3-phosphoethanolamine (DOPE) or 1,2-Dipalmitoyl-sn-glycero-3-phosphocholine (DPPC), cholesterol and 1,2-distearoyl-sn-glycero-3-phosphoethanolamine-N-[methoxy(polyethylene glycol)-2000] (DSPE-PEG2k) or 1,2-dipalmitoyl-sn-glycerol, methoxypolyethylene Glycol (DPG-PEG2k) (9:6:5:1 molar ratio) were dissolved in ethanol and rapidly injected into a citrate-buffered solution (10 mM citric acid, 150 mM NaCl, pH 4.5) comprising chemically modified mRNA encoding firefly luciferase at an molar lipid-nitrogen/mRNA-phosphate ratio of 17 to yield a final ethanol concentration of 20% and dialyzed against water for 24 h.

Transmission Electron Microscopy:

For size analysis, TEM (Transmission Electron Microscopy) was used with magnifications of 10,000 and 60,000. As a first step, copper-based plates (Plano GmbH; S162-3) were plasma cleaned. After this treatment 8 µl of lipidoid formulation were brought in contact with a copper plate for 3 min. After removing the lipidoid formulation droplet the sample was stain by bringing the lipidoid loaded copper plate in contact with one drop of 8 µl uranyl acetate solution twice for 30 s. After every step the liquids were removed by withdrawing with a blotting paper. Finally the carrier plates are dried at room temperature for further 30 min and analyzed via a Jem1011 (Jeol).

Results

Figure 21:
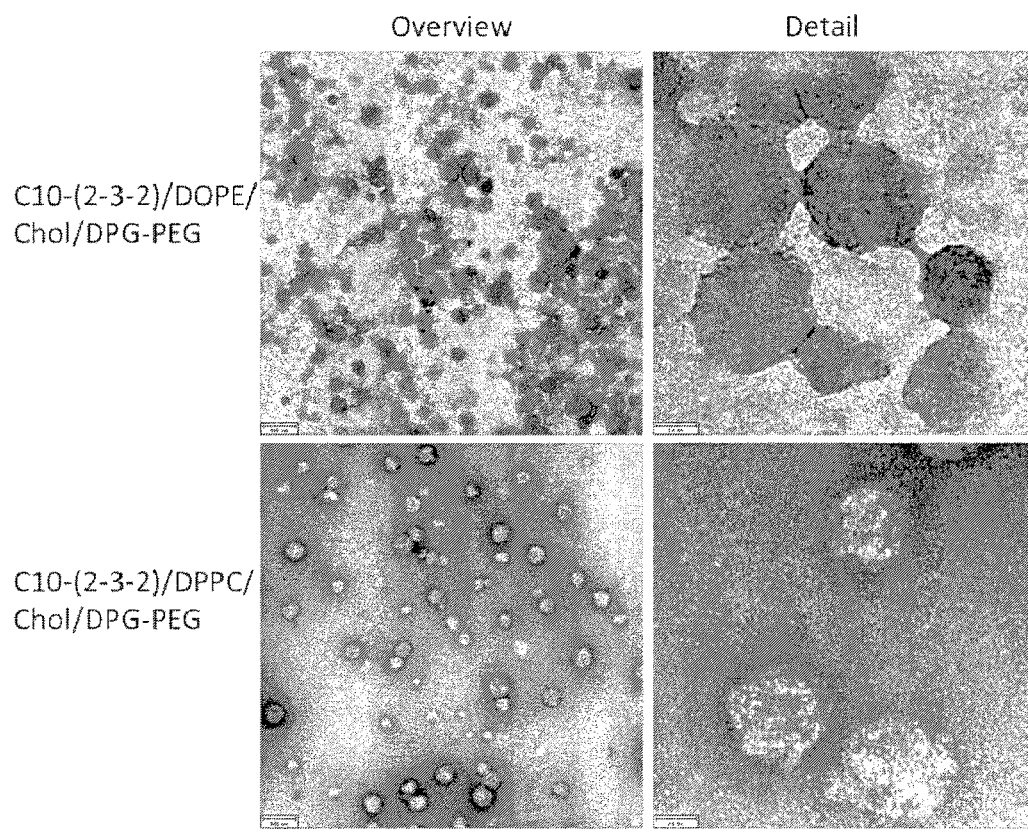
FIG. 21: Transmission electron microscopy pictures of lipoplexes Lipidoid/mRNA complexes were formed as described and analyzed via transmission electron microscopy. Upper lane: C10-(2-3-2)/DOPE/Chol/DPG-PEG, lower lane: C10-(2-3-2)/DPPC/Chol/DPG-PEG; left pictures overview scale: 100 nm; right pictures: detailed zoom scale 20 nm.

The TEM pictures (FIG. 21) show that the formed lipidoid formulations are spherical particles with a homogenous size distribution (overview). In the zoomed picture the size of these particles can be estimated to 60-80 nm.

EXAMPLE 16 mRNA Transport Efficiency of C10-(2-3-2) Synthesized Via an Alcylhalide.

Materials and Methods

Synthesis:
Synthesis of C10-(2-3-2) was performed as described under production example VII.

Lipidoid Formulation:
Lipidoid/mRNA complexes were formed as described in example 15 using C10-(2-3-2), 1,2-distearoyl-sn-glycero-3-phosphocholine (DSPC), cholesterol, 1,2-Dipalmitoyl-snglycerol-methoxypolyethylene Glycol (DPG-PEG2k) in a molar ratio of 9:6:5:1 and mRNA encoding for firefly luciferase at N/P 17.

In Vitro Transfection:

24 h prior to treatment 5,000 NIH3T3 cells in 100 µL medium were seeded into a well of a 96-well plate. At day of transfection lipidoid formulations were formed as described and adjusted to 1×PBS with a 10×PBS solution. The lipidoid formulations were diluted to result in 500 ng, 250 ng or 125 ng in 50 µL, added to the cells and incubated for 24 h at 37° C. and 5% $CO_2$. 24 h after transfection the medium was removed. Cells were lysed and lysates analyzed for reporter protein activity as described in example 1.

Results

Figure 22:
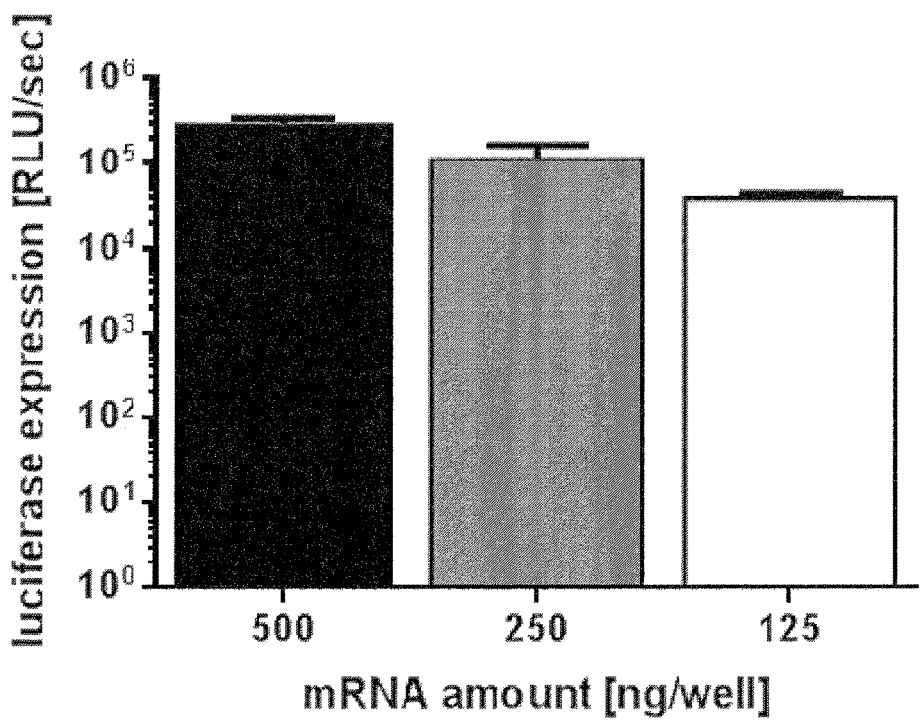
FIG. 22: Transfection efficiency of C10-(2-3-2) synthesized from 1-bromodecane C10-(2-3-2) was synthesized as described under production example VII using 1-bromodecane. Transfection efficiency was tested on NIH3T3 cells using doses of 500 ng, 250 ng and 125 ng per well.

As shown in FIG. 22 C10-(2-3-2) synthesized via an alcylhalide is able to transport mRNA into a cell leading to expression of the reporter protein luciferase.

EXAMPLE 17 mRNA Transport Efficiency of C12-(2-3-2) Synthesized Via N-Dodecylacrylamide.

Materials and Methods

Synthesis:

Synthesis of C12-(2-3-2) was performed as described under production example VIII.

Lipidoid Formulation:

Lipidoid/mRNA complexes were formed as described in example 15 using C12-(2-3-2), 1,2-distearoyl-sn-glycero-3-phosphocholine (DSPC), cholesterol, 1,2-Dipalmitoyl-sn-glycerol-methoxypolyethylene Glycol (DPG-PEG2k) in a molar ratio of 9:6:5:1 and mRNA encoding for firefly luciferase at N/P 17.

In Vitro Transfection:

Transfection experiments were performed as described in example 16 using an mRNA dose of 500, 250 or 125 ng per well.

Results

Figure 23:
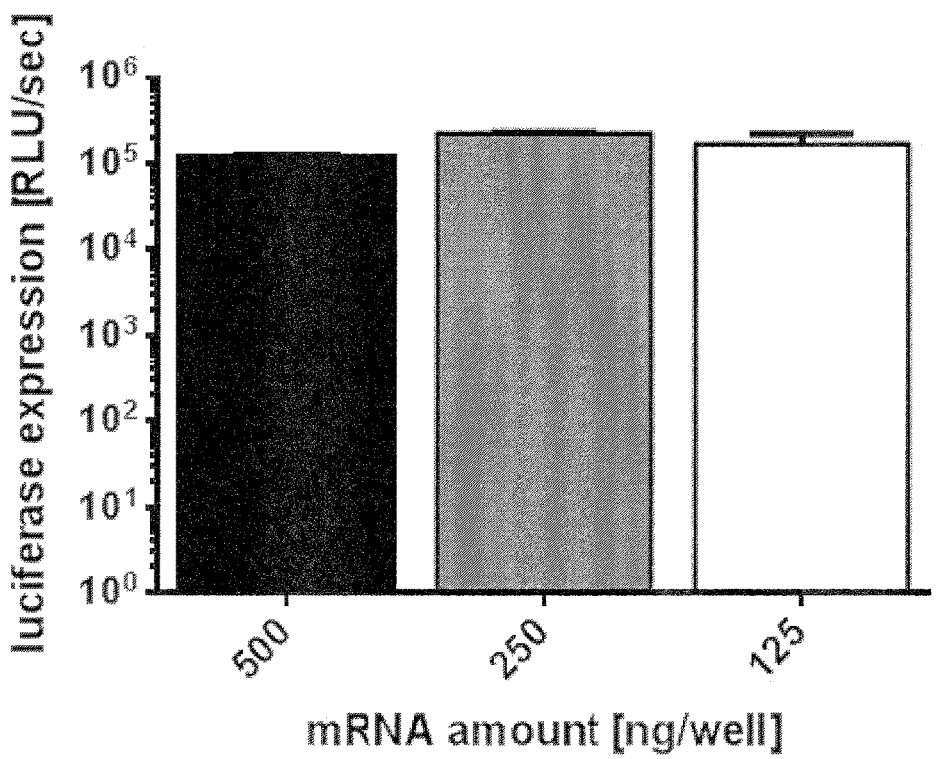
FIG. 23: Transfection efficiency of C12-(2-3-2) synthesized from N-dodecyl acrylamide C12(2-3-2) was synthesized as described under production example VIII using N-dodecyl acrylamide. Transfection efficiency was tested on NIH3T3 cells using doses of 500 ng, 250 ng and 125 ng per well.

As shown in FIG. 23 C12-(2-3-2) synthesized via N-dodecyl acrylamide is able to transport mRNA into a cell leading to reporter gene expression of luciferase.

EXAMPLE 18 mRNA Transport Efficiency of C12-(2-3-2) Synthesized Via Dodecyl-Acrylate.

Materials and Methods

Synthesis of C12-(2-3-2) was performed as described under production example IX.

Lipidoid Formulation:

Lipidoid/mRNA complexes were formed as described in example 15 using C12-(2-3-2), 1,2-distearoyl-sn-glycero-3-phosphocholine (DSPC), cholesterol, 1,2-Dipalmitoyl-sn-glycerol-methoxypolyethylene Glycol (DPG-PEG2k) in a molar ratio of 9:6:5:1 and mRNA encoding for firefly luciferase at N/P 17.

In Vitro Transfection:

Transfection experiments were performed as described in example 16 using an mRNA dose of 500, 250 or 125 ng per well.

Results

Figure 24:
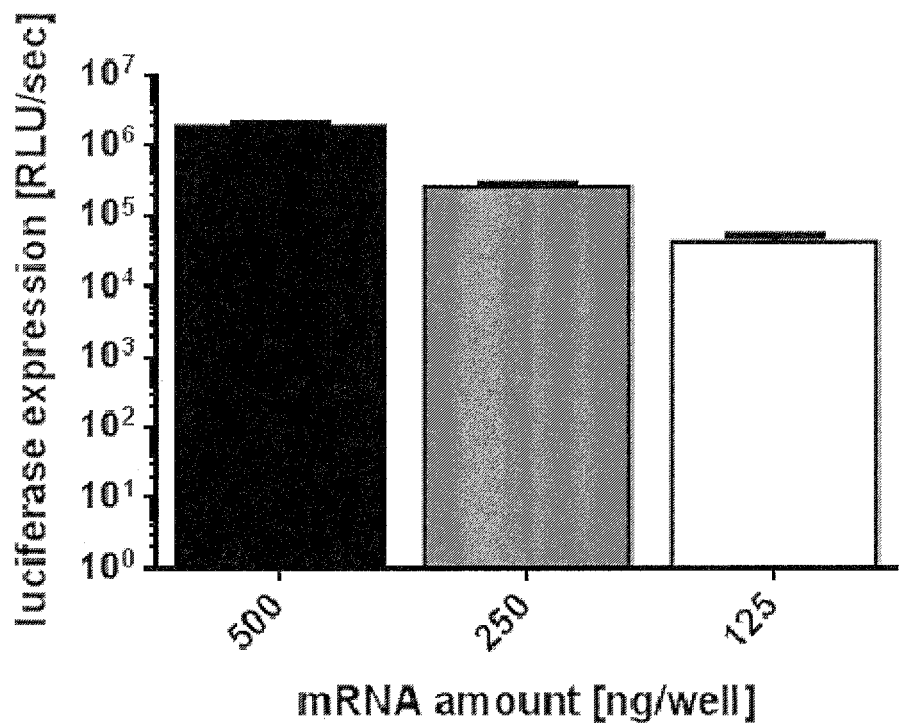
FIG. 24: Transfection efficiency of C12-(2-3-2) synthesized from dodecyl-acrylate C12-(2-3-2) was synthesized as described under production example IX using dodecyl-acrylate. Transfection efficiency was tested on NIH3T3 cells using doses of 500 ng, 250 ng and 125 ng per well.

As shown in FIG. 24 C12-(2-3-2) synthesized via dodecyl acrylate is able to transport mRNA into a cell leading to expression of the reporter protein luciferase.

EXAMPLE 19 mRNA Transport Efficiency of C12-(2-3-2) Formulated Using Different Helper Lipids and Different Lipidoid to mRNA (N/P) Ratios.

Materials and Methods

Lipidoid Formulation:

Lipidoid/mRNA complexes were formed as described in example 15 using C12-(2-3-2) in combination with 1,2-dimyristoyl-sn-glycerol-methoxypolyethylene Glycol (DMG-PEG2k) as PEG-lipid, DOPE or DSPC as helper lipids and N/P ratio 17 or 8.

In Vitro Transfection:

Transfection experiments were performed as described in example 16 using an mRNA dose of 250 ng per well.

Results

Figure 25:
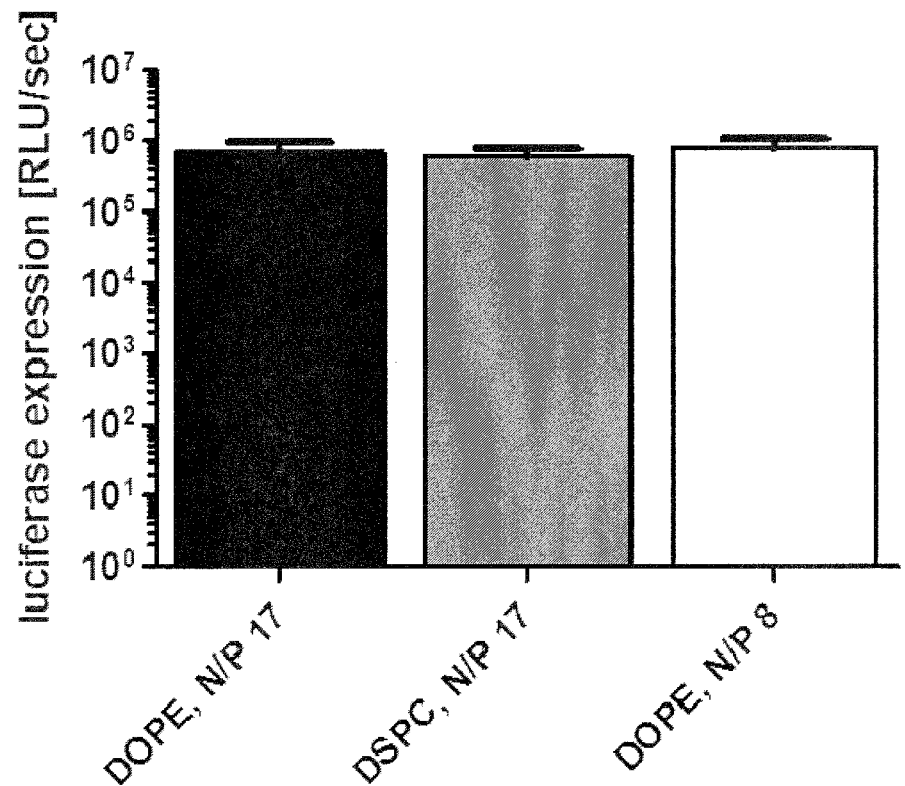
FIG. 25: Transfection efficiency of C12-(2-3-2) based lipidoid formulation. Lipidoid formulations were generated using C12-(2-3-2) and DMG-PEG2k in combination with DOPE or DSPC with mRNA coding for firefly luciferase at N/P 17 or 8

As shown in FIG. 25 C12-(2-3-2) is able to transport mRNA into a cell leading to reporter gene expression of luciferase in combination with different helper lipids (DOPE, DSPC) and at different N/P ratios (17 or 8). Thus C12-(2-3-2) efficiently transports RNA into cells independent of helper lipid and N/P ratio.

EXAMPLE 20

Improved mRNA Transport Efficiency in Mice after Intra Venous Administration of the Lipidoid Formulation with C12-(2-3-2) Compared to C12-(2-2-2) and C12-(3-3-3)

Materials and Methods

Animals:

As described in example 11

Lipidoid Formulations:

As described in example 15 using C12-(2-3-2), 1,2-dioleoyl-sn-glycero-3-phosphoethanolamine (DOPE), cholesterol, 1,2-dimyristoyl-sn-glycerol-methoxypolyethylene Glycol (DMG-PEG2k) and mRNA encoding for firefly luciferase at N/P 17.

Measurement of Luc Activity in Mice Using In Vivo Bioluminescent Imaging:

As described in example 11, anaesthetizing the animals 6 h after administration.

Results

As shown in FIG. 26 the lipidoid formulation where C12-(2-3-2) is included leads to significantly increased reportergen expression in mice compared to C12-(3-3-3) and C12-(2-2-2). This demonstrates the beneficial mRNA transport ability of C12-(2-3-2).

EXAMPLE 21

Comparison of mRNA Transport Efficiency of Oligo(Alkylene Amine) (2-3-2) Saturated with Different Amounts of Alkyl Chain C12.

Materials and Methods

Figure 27:
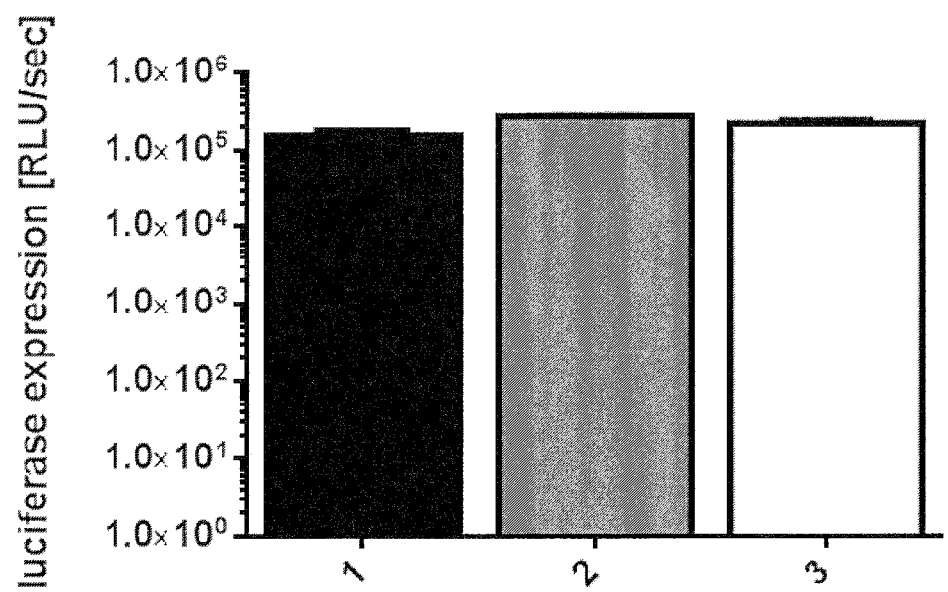
FIG. 27: Comparison of transfection efficiency of C12-(2-3-2) version with an altered C12-alkyl chain saturation and positioning. A: chemical structure of different C12-(2-3-2) versions; B: Reporter protein (firefly luciferase) expression level after transfection of NIH3T3 cells with formulations comprising the different lipids.

Lipidoid Formulation:
As described in example 15 without dialysis using olgio (alkyl amine) (2-3-2) with different modification degrees and positions (see FIG. 27 A, SynCom).
In Vitro Transfection:
Transfection experiments were performed as described in example 16 using an mRNA dose of 250 ng per well.
Results
As shown in FIG. 27 A three different versions of C12-(2-3-2) were synthesized to evaluate the influence of amount and position of alkyl chains per oligo(alkylene amine) on the mRNA transport ability. The transfection efficiency (FIG. 27 B) shows no differences in reporter protein expression proving that no differences in mRNA transport efficiency can be observed. Thus different type of C12-(2-3-2) lipidoid formulations transport mRNA with same efficiency.

EXAMPLE 22

Lyophilization of Lipidoid Formulations.

Materials and Methods

Figure 28:
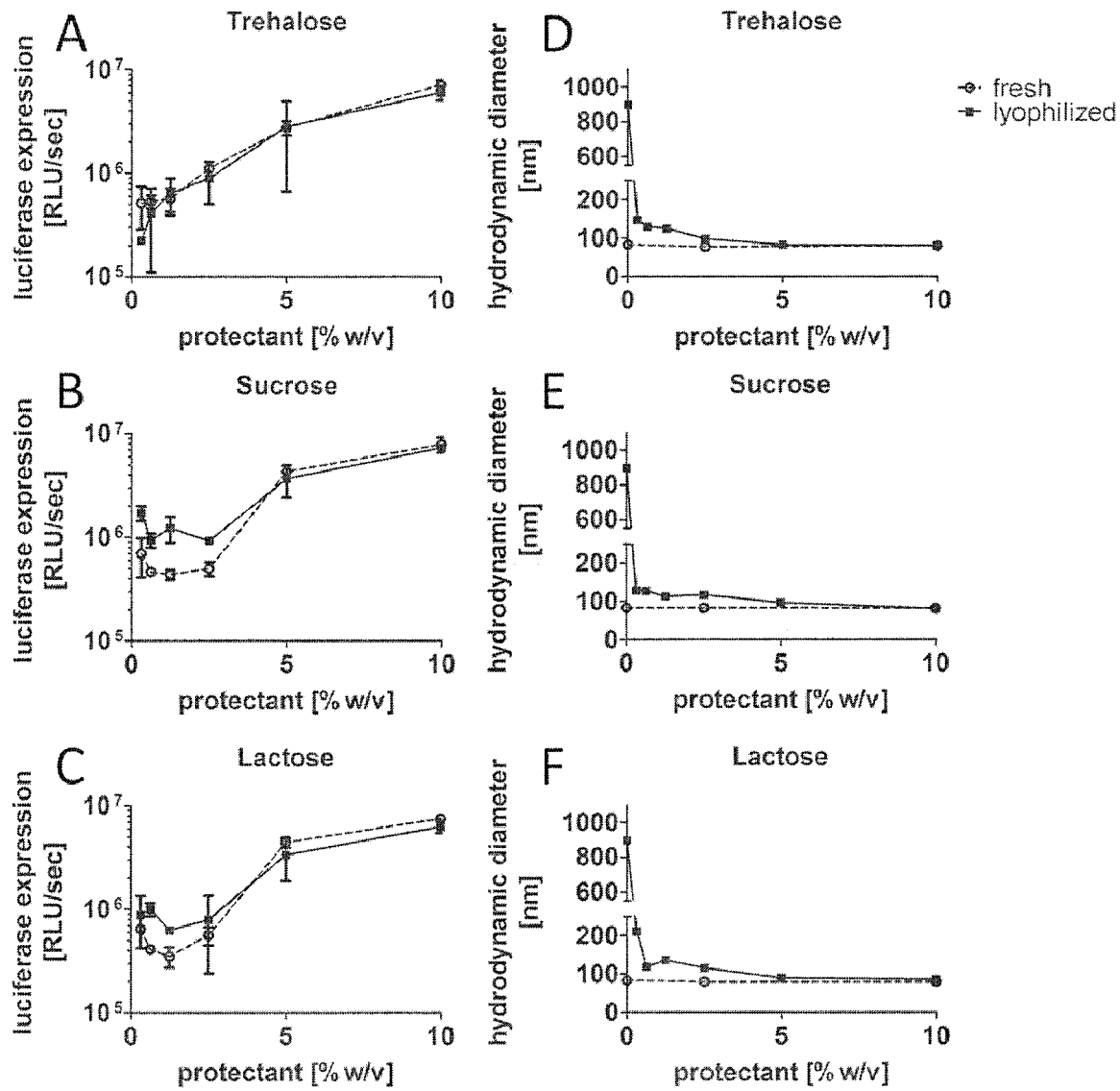
FIG. 28: Lyophilization stability of lipoplexes Lipidoid formulations were formed as described, dialyzed against water and mixed with different concentrations of lyoprotectants (trehalose (A, D), sucrose (B, E) and lactose (C, F)). After freezing, lyophilization and resuspension, transfection efficiency on NIH3T3 cells (A-C) and the hydrodynamic diameter (D-F) was measured and compared to freshly prepared lipoplexes under same conditions.

Lipidoid Formulation:
As described in example 15.
Lyophilization Process:
Protectant solutions of trehalose, sucrose and lactose were prepared in water (c: 20% w/v). Serial dilutions with a factor of 2 were prepared resulting in protectant solutions form 20% until 0.625% (w/v). To these solutions the same volume of lipidoid formulation was added and mixed by pipetting. The solutions were frozen in liquid nitrogen and lyophilized using a sigma alpha 1-4 (Martin Christ). After lyophilization the particles were resuspended in the same volume of water and used for analysis. As control lipoplexes were mixed with protectant solutions at the same concentrations without freezing and lyophilization.
In Vitro Transfection:
As described in example 15 using 233 ng of mRNA per well.
Size Measurement:
The hydrodynamic diameter of the particles was measured using a ZetaSier Nano ZS (Malvern).
Results
As shown in FIG. 28 all tested sugars were able to maintain particle size and transfection efficiency at different concentrations. In comparison particles without protectant (0%) become less efficient and strongly increase in size due to aggregation processes.

EXAMPLE 23

Transport of RNA into Mammalian Tissue Ex Vivo
Material and Methods
Lipidoid Formulation:
As described in example 15 using C12-(2-3-2), DOPE, Cholesterol, DPG-PEG2k and mRNA encoding for firefly luciferase at an N/P ratio of 17 without dialysis.
Treatment of Tissue Samples:
Tissue pieces (muscle, fat, artery or lung; see table) of approx. 1 cm$^3$ were taken from a freshly killed animal (pig or sheep; see table) and washed in PBS. Into every tissue piece 100 µL lipidoid formulation containing 10 µg RNA or 200 µL lipidoid formulation containing 20 µg RNA were injected (see table). In case of the treatment of the sheep artery, lipidoid formulations were injected into the lumen of the vessel that was closed on both ends via yarn. The tissue was cultured for 24 h in cell culture medium (DMEM) containing 10% FCS.
Analysis of Luciferase Expression:
After 24 h samples were incubated in PBS containing luciferin (100 µg/mL) for 30 min. Luciferase activity was measured using an in vivo imaging system (IVIS, Perkin Elmer).
Results
As shown in FIG. 29 C12-(2-3-2) enabled the transport of mRNA encoding for firefly luciferase into cells of a variety of different tissues of different species resulting in the expression of luciferase. In contrast non treated samples (D, E, lower tissue piece) do not show an imaging signal.

EXAMPLE 24

Expression of Angiotensin I Converting Enzyme 2 (ACE-2) In Vitro
Lipidoid Formulation:
As described in example 15 using C12-(2-3-2), DOPE, cholesterol, DPG-PEG2k without the addition of mRNA, which results in empty lipoplexes. Formulation of lipidoid mRNA complexes was performed via post loading. For this purpose 1 µL of mRNA encoding for ACE-2 (1 mg/ml) was mixed with 4 µL of the lipoplex containing solution and incubated for 10 min at room temperature.
In Vitro Transfection of Cells:
For in vitro transfection 300,000 HepG2 cells were seeded into a well of a 6 well plate 24 h prior to treatment in 2 mL medium containing 10% FCS. At day of transfection the medium was exchanged against 2 mL fresh medium. Lipidoid formulations were prepared as described and 2.5 µL containing 500 ng mRNA was added to each well. In control wells the same amount of lipidoid formulation was injected without the addition of mRNA during formulation.
Detection of ACE-2 Expression by Western Blot:
24 h after transfection medium was removed and cells washed with 1 mL PBS. Cells were lysed for 10 min on ice using 250 µl lysis buffer (25 mM Tris-HCl, 0.1% TritonX, pH 7.4). After scraping of the lysates debris was removed by centrifugation for 10 min at 14,000 rpm.
After protein estimation (BCA-Assay, Thermo-Fisher scientific) 10 µg per lane were loaded onto a 10% SDS-PAGE Gel (Thermo-Fisher scientific). After electrophoresis at 100 V for 1.5 h the gel was blotted onto a PVDF membrane (TransBlot Turbo, Biorad).
After blotting the membrane was blocked using 5% milk powder in TBS-T (20 mM Tris-HCl, 500 mM NaCl, pH 7.5, 0.1% Tween20) for 30 min. After blocking the membrane was probed with an anti-ACE2 antibody (R&D systems) in a dilution of 1:10,000 at 4° C. over night. After three washing steps (10 min, TBS-T each) the membrane was probed using an anti-goat-HRP antibody (SCBT) in a dilution of 1:10,000 for 1 h at room temperature, followed by three washing steps (10 min, TBS-T each). Signals were developed using a luminescent HRP-substrate (GE healthcare) and the signals analyzed using a camera (ChemiDoc XRS+, Bio-Rad). After detection of ACE2 signals equal loading was analyzed using an anti-GAPDH antibody (NEB) in a dilution 1:1,000 for 4 h at room temperature.
Results
In FIG. 30 the western blot result of the transfection are shown. The left two lanes show the lysates of treated cells, the right to lanes the lysate of non-treated cells. As demonstrated clearly, ACE-2 expression can only be observed in samples that were treated with lipidoid formulations post loaded with RNA coding for ACE-2. This experiment shows that ACE-2 mRNA can also be transported via C12-(2-3-2) containing Lipidoid formulation. It also demonstrates that the method of post loading of empty lipoplexes also results in efficient mRNA transport into the cell.

EXAMPLE 25

Expression of Murine Erythropoietin (mEPO) in Balb/c Mice

Materials and Methods

Lipidoid Formulation:
As described in example 15 using C12-(2-3-2), DOPE, Cholesterol, DMPE-PEG2k and mRNA encoding for murine erythropoietin (mEPO) at an N/P ratio of 15.
Animals:
As described in example 11
Treatment of Animals:
The lipidoid formulation was adjusted to 1×PBS and diluted to result in 5, 10 and 20 µg mRNA in 130 µL each. Per dose three mice were treated by intravenous injection. As control mice were treated with PBS. 6 h post treatment blood was taken and analyzed for murine EPO levels.
Quantification of Murine EPO:
The quantification auf murine erythropoietin was performed via a mouse EPO ELISA (Quantikine ELISA, R&D Systems Inc.) according to the manufacturer's protocol.
Results
In this experiment the expression of murine erythropoietin in mice after treatment with murine EPO mRNA formulated in a C12-(2-3-2) containing lipidoid formulation. As demonstrated in FIG. 31 murine EPO could be detected after 6 h in all groups in concentrations significantly higher than the PBS treated control group. Thus murine EPO mRNA was efficiently transported into cells leading to the expression of the protein.

EXAMPLE 26

Messenger RNA Transport Efficiency of Oligo(Alkylene Amine) (2-3-2) Modified Linear Polymer Poly(Allylamine)

Materials and Methods

Figure 32:
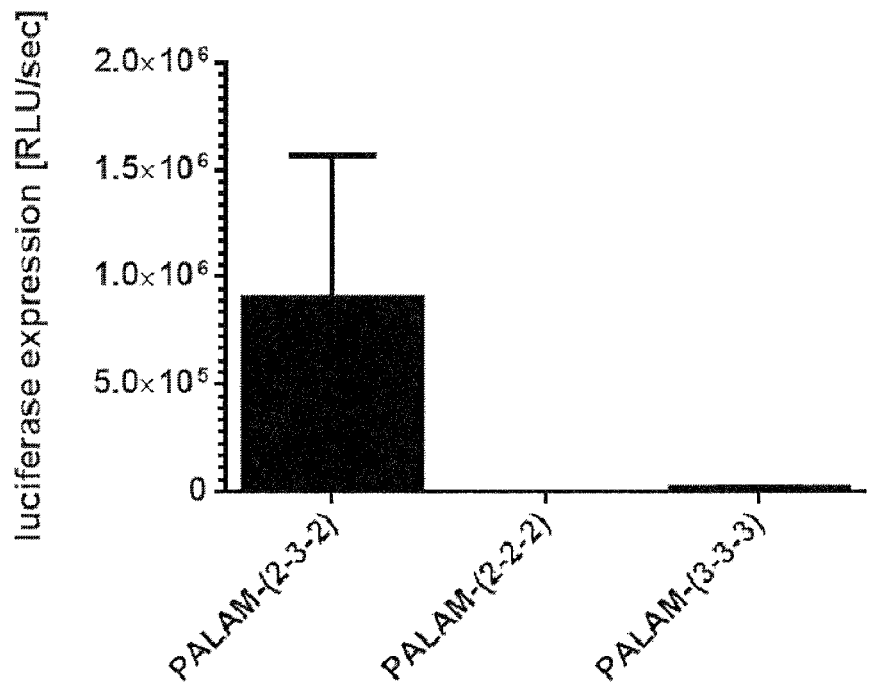
FIG. 32: Comparison of transfection efficiency of differently modified poly(allylamine) (PALAM). NIH3T3 cells were transfected using polyplexes composed of mRNA coding for luciferase complexed with PALAM-(2-3-2), PALAM-(2-2-2) or PALAM-(3-3-3).

Polyplex Formation:
As described in example 1 using poly(allylamine) (PALAM) modified with oligo(alkylene amine) (2-3-2), (2-2-2) or (3-3-3). Synthesis see production example V.
In Vitro Transfection of Polyplexes:
As described in example 1, transfecting NIH3T3 cells, using 500 ng of mRNA and N/P 12.
Results
As shown in FIG. 32 after transfection with polyplexes of mRNA and PALAM-(2-3-2) cells show a significantly higher luciferase expression than after transfection with PALAM-(2-2-2)/mRNA or PALAM-(3-3-3)/mRNA complexes. Thus these results demonstrate that the modification of a linear, amine terminated polymer with an oligo(alkylene amine) with alternating alkyl chains leads to the same beneficial effect as on a linear, carboxyl terminated polymer backbone.

EXAMPLE 27

Figure 33:
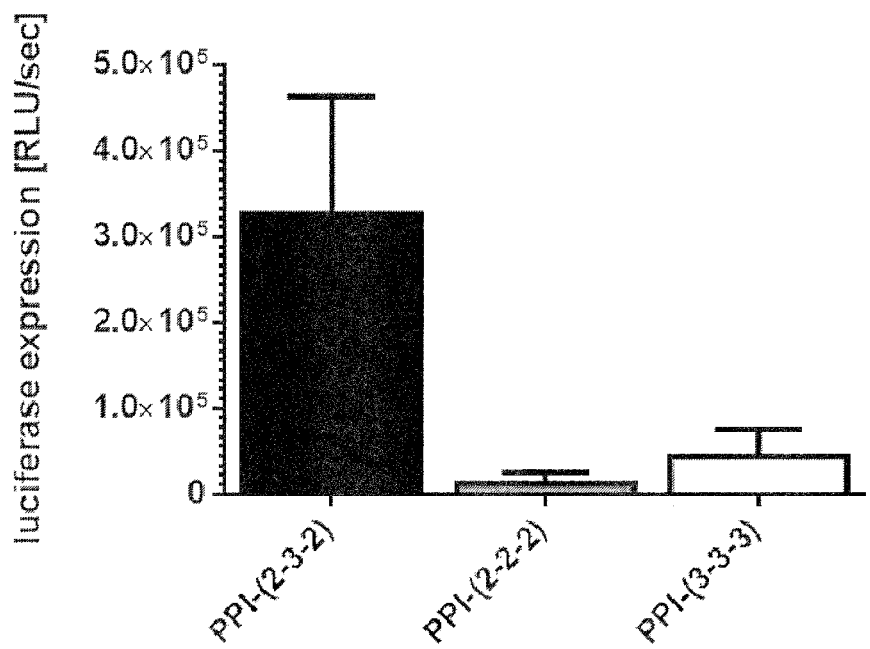
FIG. 33: Comparison of transfection efficiency of differently modified polypropylenimine (PPI). NIH3T3 cells were transfected using polyplexes composed of mRNA coding for luciferase complexed with PPI-(2-3-2), PPI-(2-2-2) or PPI-(3-3-3).

Messenger RNA Transport Efficiency of Oligo(Alkylene Amine) (2-3-2) Modified Dendritic Polymer Polypropylenimine Materials and Methods Polyplex Formation:
As described in example 1 using polypropylenimine (PPI) modified with oligo(alkylene amine) (2-3-2), (2-2-2) or (3-3-3). Synthesis see production example VI.
In Vitro Transfection of Polyplexes:
As described in example 1, transfecting NIH3T3 cells, using 500 ng of mRNA and N/P 32.
Results
As shown in FIG. 33 after transfection with polyplexes of mRNA and PPI-(2-3-2) cells show a significantly higher luciferase expression than after transfection with PPI-(2-2-2)/mRNA or PPI-(3-3-3)/mRNA complexes. Thus these results demonstrate that the modification of a dendritic polymer with an oligo(alkylene amine) with alternating alkyl chains leads to the same beneficial effect as on a linear polymer backbone.

EXAMPLE 28

Figure 34:
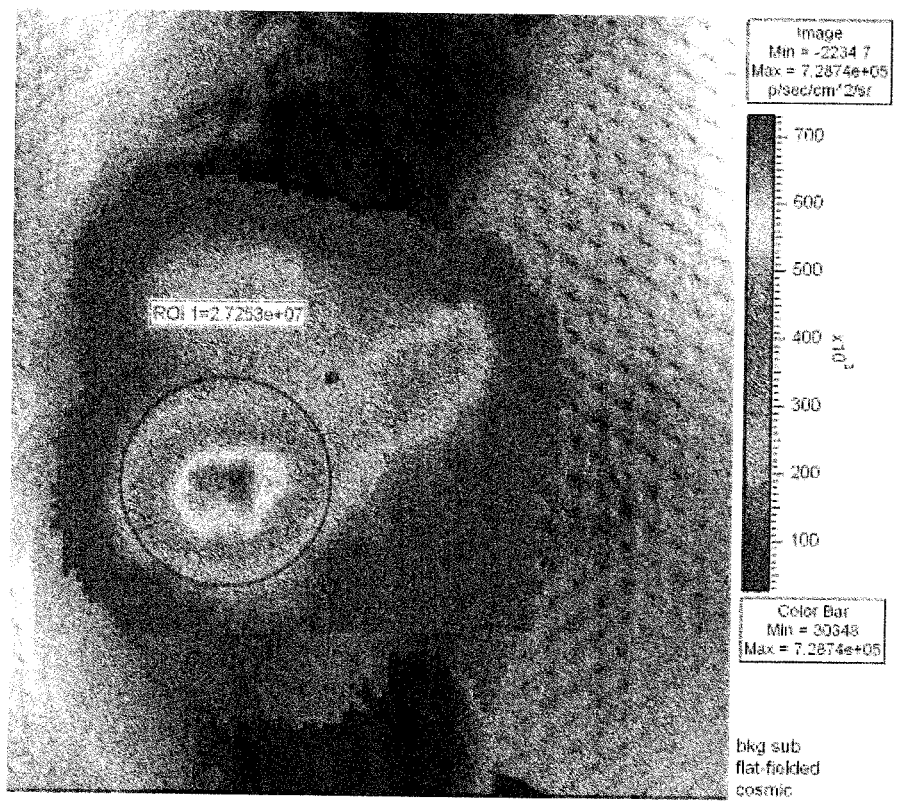
FIG. 34: Expression of luciferase after subcutaneous injection of a C12-(2-3-2) formulation. C12-(2-3-2)/DOPE/Cholesterol/DMG-PEG2k containing mRNA coding for firefly luciferase The following Examples serve to illustrate the invention.

Intra Cellular RNA Transport Efficiency of C12-(2-3-2) Formulation after Subcutaneous Injection in Rats Materials and Methods Lipidoid Formulation:
As described in example 15 using C12-(2-3-2), DOPE, Cholesterol, DMG-PEG2k and mRNA encoding for firefly luciferase at an N/P ratio of 17.
Treatment of Animals:
The lipidoid formulation was adjusted to 1×PBS. 500 µL of the formulation containing 63 µg RNA were injected subcutaneous into female Buffalo rats 6 h after administration the rat was anaesthetized by intraperitoneal injection of medetomidine (11.5 µg/kg BW), midazolame (115 µg/kg BW) and fentanyl (1.15 µg/kg BW). D-luciferin substrate (30 mg in PBS per mouse) was applied via intraperitoneal injection. Bioluminescence was measured 10 minutes later, using an IVIS 100 Imaging System (Xenogen, Alameda, USA).
Results
As demonstrated in FIG. 34 the rat shows a bright luminescent signal at the side of injection demonstrating that the transport of the RNA into the surrounding tissue was very efficient. It also show that the functionality of RNA remains intact as the encoding protein can be produced.

The invention claimed is:
1. A composition comprising a single stranded mRNA and a
a lipidoid having the structure of formula (IV):

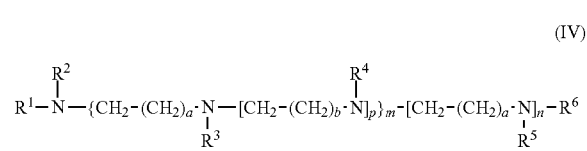

(IV)

wherein the variables a, b, p, m, n and $R^1$ to $R^6$ are defined as follows:

a is 1 and b is an integer of 2 to 4, or a is an integer of 2 to 4 and b is 1;

p is 1 or 2;

m is 1 and n is 1, m is 2 and n is 0, or m is 2 and n is 1; and $R^1$ to $R^6$ are independently of each other selected from: hydrogen; —$CH_2$—CH(OH)—$R^7$, —CH($R^7$)—$CH_2$—OH, —$CH_2$—$CH_2$—(C=O)—NH—$R^7$ and —$CH_2$—$R^7$, wherein $R^7$ is selected from C3-C18 alkyl and C3-C18 alkenyl having one C—C double bond; a protecting group for an amino group; —C(NH)—$NH_2$; a poly(ethylene glycol) chain; and a receptor ligand; provided that at least two of $R^1$ to $R^6$ are —$CH_2$—CH(OH)—$R^7$, —CH($R^7$)—$CH_2$—OH, —$CH_2$—$CH_2$—(C=O)—NH—$R^7$ or —$CH_2$—$R^7$ and one of $R^1$, $R^2$, $R^5$, and $R^6$ is hydrogen, wherein $R^7$ is selected from C3-C18 alkyl and C3-C18 alkenyl having one C—C double bond; and wherein one or more nitrogen atoms may be protonated.

2. The composition of claim 1, comprising the single stranded mRNA and the lipidoid having the structure of formula (IVa):

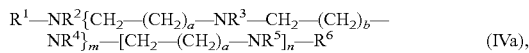

$$R^1\text{—}NR^2\{CH_2\text{—}(CH_2)_a\text{—}NR^3\text{—}CH_2\text{—}(CH_2)_b\text{—}NR^4\}_m\text{—}[CH_2\text{—}(CH_2)_a\text{—}NR^5]_n\text{—}R^6 \quad (IVa),$$

wherein a, b, m, n, and $R^1$ to $R^6$ are defined as in claim 1.

3. The composition of claim 1, wherein n is 1.

4. The composition of claim 1, wherein m is 1 and n is 1.

5. The composition of claim 1, wherein a is 1 and b is 2 or a is 2 and b is 1.

6. The composition of claim 1, which is in lyophilized form.

7. The composition of claim 6, which further comprises a lyoprotectant.

8. The composition of claim 7, wherein the lyoprotectant is at least one of trehalose, sucrose and lactose.

9. A pharmaceutical composition comprising the composition of claim 1.

10. A method for delivering single stranded mRNA to a target cell or tissue comprising the step of bringing the composition of claim 1 into contact with the target cell or tissue.

11. The composition of claim 1, wherein the lipidoid forms a complex with the single stranded mRNA.

12. The composition of claim 1, wherein a is 1 and b is 2 or 3, or a is 2 and b is 1;

p is 1; and m is 1 and n is 1.

13. The composition of claim 1, wherein the composition has a positive zeta potential.

14. The composition of claim 13, wherein the composition has an N/P ratio of 3 to 60.

15. The composition of claim 13, wherein the composition has an N/P ratio of 4 to 44.

16. The composition of claim 13, wherein the composition has an N/P ratio of 2 to 10.

17. The composition of claim 1, wherein the composition does not comprise siRNA.

18. The composition of claim 7, wherein the lyoprotectant is lactose.

19. A particle comprising the composition of claim 1, wherein the particle diameter ranges from 10 to 500 nm.

20. A particle comprising the composition of claim 1, wherein the particle diameter ranges from 20 to 150 nm.

21. The composition of claim 1, wherein at least two of the $R^1$ to $R^6$ are —$CH_2$—CH(OH)—$R^7$ or —CH($R^7$)—$CH_2$—OH.

22. The composition of claim 13, wherein the composition has an N/P ratio of 8 to 20.

23. The composition of claim 7, wherein five of $R^1$ to $R^6$ are —$CH_2$—CH(OH)—$R^7$ or —CH($R^7$)—$CH_2$—OH, wherein $R^7$ is C8-C16 alkyl or C8-C16 alkenyl having one C—C double bond.

* * * * *